US010010585B2

(12) United States Patent
Stankovic et al.

(10) Patent No.: US 10,010,585 B2
(45) Date of Patent: Jul. 3, 2018

(54) METHODS OF TREATING VESTIBULAR SCHWANNOMA AND REDUCING HEARING OR NEURITE LOSS CAUSED BY VESTIBULAR SCHWANNOMA

(71) Applicant: Massachusetts Eye and Ear Infirmary, Boston, MA (US)

(72) Inventors: Konstantina Stankovic, Boston, MA (US); Sonam Dilwali, Dallas, TX (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 14/741,332

(22) Filed: Jun. 16, 2015

(65) Prior Publication Data
US 2015/0359851 A1 Dec. 17, 2015

Related U.S. Application Data

(60) Provisional application No. 62/012,957, filed on Jun. 16, 2014.

(51) Int. Cl.
C07K 16/24 (2006.01)
A61K 39/395 (2006.01)
G01N 33/574 (2006.01)
A61K 38/18 (2006.01)
C07K 16/40 (2006.01)
A61K 39/00 (2006.01)

(52) U.S. Cl.
CPC ........ *A61K 38/1825* (2013.01); *C07K 16/241* (2013.01); *C07K 16/40* (2013.01); *A61K 2039/505* (2013.01); *C07K 2317/76* (2013.01)

(58) Field of Classification Search
None
See application file for complete search history.

(56) References Cited

U.S. PATENT DOCUMENTS

2009/0306225 A1* 12/2009 Lichter ................ A61K 9/0046
514/772.1
2015/0093399 A1* 4/2015 Jefferies ........... A61K 47/48246
424/178.1

OTHER PUBLICATIONS

Gentry et al. (Journal of Biological Chemistry, 2000, 275:7558-7565).*
Yue et al. (Cancer Research, AACR 102 Annual Meeting, 2011, Abstract 1036).*
Ahmad et al., "Merlin knockdown in human schwann cells: Clues to vestibular schwannoma tumorigenesis," Otology & Neurotology. Apr. 2010;31(3):460-6.
Ammoun et al., "Axl/Gas6/NFkB signalling in schwannoma pathological proliferation, adhesion and survival," Oncogene. 2013, 1-11.
Ammoun et al., "ErbB/HER receptor activation and preclinical efficacy of lapatinib in vestibular schwannoma," Neuro Oncol. Aug. 2010;12(8):834-43.

Aminpour et al., "Role of tumor necrosis factor-alpha in sensorineural hearing loss after bacterial meningitis," Otol Neurotol. Jul. 2005;26(4):602-9.
Balkwill, "Tumour necrosis factor and cancer," Nat Rev Cancer. May 2009;9(5):361-71.
Beg et al., "Tumor necrosis factor and interleukin-1 lead to phosphorylation and loss of I kappa B alpha: a mechanism for NF-kappa B activation," Mol Cell Biol. Jun. 1993;13(6):3301-3310.
Cayé-Thomasen et al., "VEGF and VEGF receptor-1 concentration in vestibular schwannomas homogenates correlates to tumor growth rate," Otol Neurotol. Jan. 2005;26(1):98-101.
Cutro et al., "Contact-dependent inhibition of EGFR signaling by Nf2/Merlin," J Cell Biol. Jun. 4, 2007;177(5):893-90.
Doherty et al., "ErbB and Nrg: potential molecular targets for vestibular schwannoma pharmacotherapy," Otol Neurotol. Jan. 2008;29(1):50-7.
Gilmore, "NF-kB Transcription Factors". Boston University. website: www.nf-kb.org, May 22, 2014, 7 pages.
Haake et al., "Dexamethasone protects auditory hair cells against TNFalpha-initiated apoptosis via activation of PI3K/Akt and NFkappaB signaling," Hear Res. Sep. 2009;255(1-2):22-32.
Hoesel and Schmid, "The complexity of NF-κB signaling in inflammation and cancer," Mol Cancer. Aug. 2, 2013;12:86.
Hong et al., "Cyclooxygenase-2 Supports Tumor Proliferation in Vestibular Schwannomas," Neurosurgery. Apr. 2011;68:1112-1117.
Jacob et al., "Phosphatidylinositol 3-kinase/AKT pathway activation in human vestibular schwannoma," Otol Neurotol.Jan. 2008;29(1):58-68.
Kandathil et al., "Aspirin intake correlates with halted growth of sporadic vestibular schwannoma in vivo," Otol Neurotol. Feb. 2014;35(2):353-7.
Karajannis et al., "Phase II trial of lapatinib in adult and pediatric patients with neurofibromatosis type 2 and progressive vestibular schwannomas," Neuro Oncol. Sep. 2012;14 (9):1163-70.
Kikkawa et al., "Hepatocyte growth factor protects auditory hair cells from aminoglycosides," Laryngoscope. Oct. 2009;119(10):2027-31.
Lallemand et al., "Merlin regulates transmembrane receptor accumulation and signaling at the plasma membrane in primary mouse Schwann cells and in human schwannomas," Oncogene. Feb. 12, 2009;28(6):854-65.
Lassaletta et al., "cDNA microarray expression profile in vestibular schwannoma: correlation with clinical and radiological features," Cancer Genet Cytogenet Oct. 15, 2009;194:125-7.
Lobo et al., "Review of the biologic agents used for immune-mediated inner ear disease," Acta Otorrinolaringol Esp. May-Jun. 2013;64(3):223-9.
Low et al., "Basic fibroblast growth factor (FGF-2) protects rat cochlear hair cells in organotypical culture from aminoglycoside injury," J Cell Physiol. Jun. 1996;167(3):443-450.
Lysaght et al, "Proteome of human perilymph," J Proteome Res. Sep. 2, 2011;10(9):3845-51.
Marín et al., "Curcumin downregulates the constitutive activity of NF-kB and induces apoptosis in novel mouse melanoma cells," Melanoma Res. Oct. 2007;17(5):274-83.
Miller et al., "Molecular pathogenesis of vestibular schwannomas: Insights for the development of novel medical therapies," Otolaryngologia Polska. Mar.-Apr. 2012;66(2):84-95.

(Continued)

Primary Examiner — Julie Wu
(74) Attorney, Agent, or Firm — Fish & Richardson P.C.

(57) ABSTRACT

Methods to reduce the proliferation of vestibular schwannoma (VS) cells and/or provide neuroprotection to reduce the risk of sensorineural hearing loss (SNHL), vestibular dysfunction and facial nerve paralysis in subjects with VS. The methods can include one or more of decreasing TNF-α activity or expression; decreasing NF-κB expression or activity; decreasing COX-2 expression or activity; administering FGF2; decreasing HGF expression or activity; or decreasing c-Met expression or activity.

5 Claims, 27 Drawing Sheets

(56) References Cited

OTHER PUBLICATIONS

Olson et al., "p38 mitogen-activated protein kinase controls NF-kB transcriptional activation and tumor necrosis factor alpha production through RelA phosphorylation mediated by mitogen- and stress-activated protein kinase 1 in response to Borrelia burgdorferi antigens," Infect Immun. Jan. 2007;75(1):270-7.

Picciotti et al., "Age-dependent modifications of expression level of VEGF and its receptors in the inner ear," Exp Gerontol. Aug. 2004;39(8):1253-8.

Plotkin et al., "Bevacizumab for progressive vestibular schwannoma in neurofibromatosis type 2: a retrospective review of 31 patients," Otol Neurotol. Aug. 2012;33(6):1046-52.

Plotkin et al., "Hearing improvement after bevacizumab in patients with neurofibromatosis type 2," N Engl J Med. Jul. 23, 2009;361(4):358-67.

Roosli et al., "Dysfunction of the cochlea contributing to hearing loss in acoustic neuromas: an underappreciated entity," Otol Neurotol. Apr. 2012;33(3):473-80.

Roosli et al., "What is the site of origin of cochleovestibular schwannomas?" Audiol Neurootol. 2012;17(2):121-5.

Schultz et al., "Noncoding mutations of HGF are associated with nonsyndromic hearing loss, DFNB39," Am J Hum Genet. Jul. 2009;85(1):25-39.

Sobolewski et al., "The role of cyclooxygenase-2 in cell proliferation and cell death in human malignancies," Int J Cell Biol. 2010;2010:215158, 21 pages.

Sørensen et al., "Functional diversity of FGF-2 isoforms by intracellular sorting," Bioessays. May 2006;28(5):504-14.

Stankovic et al., "Genetic determinants of hearing loss associated with vestibular schwannomas," Otol Neurotol Aug. 2009; 30(5):661-667.

Thakur et al., "An update on unilateral sporadic small vestibular schwannoma," Neurosurg Focus. Sep. 2012;33(3):E1.

Zhai et al., "Basic fibroblast growth factor protects auditory neurons and hair cells from glutamate neurotoxicity and noise exposure," Acta Otolaryngol. Mar. 2004;124(2):124-9.

Zhai et al., "Protective effect of basic fibroblast growth factor on auditory hair cells after noise exposure," Acta Otolaryngol. Jun. 2002;122(4):370-3.

\* cited by examiner

METHODS OF TREATING VESTIBULAR SCHWANNOMA AND REDUCING HEARING OR NEURITE LOSS CAUSED BY VESTIBULAR SCHWANNOMA

CLAIM OF PRIORITY

This application claims the benefit of U.S. Provisional Application Ser. No. 62/012,957, filed on Jun. 16, 2014. The entire contents of the foregoing are incorporated herein by reference.

FEDERALLY SPONSORED RESEARCH OR DEVELOPMENT

This invention was made with Government support under Grant No. T32DC00038 and K08DC010419 awarded by the National Institute on Deafness and Other Communication Disorders of the National Institutes of Health and Grant No. W81XWH-14-1-0091 awarded by the United States Department of Defense. The Government has certain rights in the invention.

TECHNICAL FIELD

The present invention relates to methods to reduce the proliferation of vestibular schwannoma cells and/or provides neuroprotection to reduce the risk of sensorineural hearing loss (SNHL), vestibular dysfunction and facial nerve paralysis. The methods can include one or more of decreasing Tumor Necrosis Factor alpha (TNF-α) activity or expression; decreasing Nuclear Factor kappa B (NF-κB) expression or activity decreasing cyclooxygenase-2 (COX-2) expression or activity; administering FGF2; decreasing hepatocyte growth factor (HGF) expression or activity; or decreasing c-Met expression or activity.

BACKGROUND

Vestibular schwannomas (VSs) are the most common tumors of the cerebellopontine angle. Due to their location within the internal auditory canal and the cerebellopontine angle, VSs can lead to substantial morbidity, including sensorineural hearing loss (SNHL), vestibular dysfunction and facial nerve paralysis (Mahaley et al., 1990). Currently, patients with symptomatic or growing VSs can undergo surgical resection or radiotherapy, both procedures that can result in serious complications. Well-tolerated pharmacotherapies against VS are needed to augment the current treatment options.

SUMMARY

The present invention is based, at least in part, on the discovery that decreasing TNF-α activity or expression reduces the proliferation of vestibular schwannoma cells and also provides neuroprotection, decreasing NF-κB expression or activity reduces the proliferation of vestibular schwannoma cells and induces cell death of vestibular schwannoma cells, decreasing COX-2 expression or activity reduces the proliferation of vestibular schwannoma cells, administration of FGF2 provides neuroprotection, and decreasing HGF expression or activity or decreasing c-Met expression or activity reduces the proliferation of vestibular schwannoma cells. In view of these discoveries, provided herein are methods of reducing the proliferation of a vestibular schwannoma cell (e.g., in vivo (e.g., in a human subject), in vitro, and/or ex vivo) that include contacting the vestibular schwannoma cell with an effective concentration of one or more of: a TNF-α inhibitor (e.g., any of the exemplary TNFα inhibitors described herein or known in the art), an NF-κκB inhibitor (e.g., any of the exemplary NF-κB inhibitors described herein or known in the art), an inhibitor of downstream effector of NF-κB (e.g., any of the downstream effectors of NF-κB described herein or known in the art), a COX-2 inhibitor (e.g., any of the exemplary COX-2 inhibitors described herein or known in the art), a HGF inhibitor (e.g., any of the HGF inhibitors described herein or known in the art), and an c-Met inhibitor (e.g., any of the c-Met inhibitors described herein or known in the art). Also provided herein are methods of treating a subject (e.g., a human) having vestibular schwannoma and methods of reducing the rate of vestibular schwannoma tumor growth in a subject (e.g., a human diagnosed as having vestibular schwannoma) that include administering to the subject a therapeutically effective amount of one or more of: a TNFα inhibitor (e.g., any of the exemplary TNFα inhibitors described herein or known in the art), an NF-κB inhibitor (e.g., any of the exemplary NF-κB inhibitors described herein or known in the art), an inhibitor of downstream effector of NF-κB (e.g., any of the downstream effectors of NF-κB described herein or known in the art), a COX-2 inhibitor (e.g., any of the exemplary COX-2 inhibitors described herein or known in the art), a HGF inhibitor (e.g., any of the HGF inhibitors described herein or known in the art), and an c-Met inhibitor (e.g., any of the c-Met inhibitors described herein or known in the art). Also provided are methods of inducing or increasing vestibular schwannoma cell death in a subject in need thereof (e.g., a subject having vestibular schwannoma) (e.g., as compared to the level of vestibular schwannoma cell death in a control subject not receiving therapeutic treatment or receiving a different therapeutic treatment) that include administering to a subject a therapeutically effective amount of an NF-κB inhibitor (e.g., any of the exemplary NF-κB inhibitors described herein or known in the art). Also provided are methods of reducing neurotoxic (e.g., ototoxic) damage to an auditory nerve, a cochlea, or a vestibular system in a subject (e.g., a subject having vestibular schwannoma) that include administering to the subject a therapeutically effective amount of one or more of: a TNFα inhibitor (e.g., any of the exemplary TNF-α inhibitors described herein or known in the art), a human FGF protein, or a nucleic acid containing a sequence that encodes a FGF protein (e.g., a human FGF protein) (e.g., a vector including a heterologous promoter operably linked to a sequence encoding a human FGF protein).

Thus, provided herein are methods for reducing the proliferation of a vestibular schwannoma cell, wherein the method comprises contacting the vestibular schwannoma cell with an effective concentration of one or more of: a TNF-α inhibitor, an NF-kB inhibitor, an inhibitor of downstream effector of NF-kB, a COX-2 inhibitor, a HGF inhibitor, and an c-Met inhibitor. In some embodiments, the vestibular schwannoma cell is ex vivo; in some embodiments, the vestibular schwannoma cell is in a subject, e.g., a mammal, e.g., a human.

In some embodiments, the subject is or has been diagnosed as having vestibular schwannoma, e.g., using methods known in the art.

Also provided herein are methods for treating a subject having vestibular schwannoma. The methods include administering to the subject a therapeutically effective amount of one or more of: a TNFα inhibitor, an NF-kB inhibitor, an inhibitor of downstream effector of NF-kB, a COX-2 inhibitor, a HGF inhibitor, and an c-Met inhibitor.

Further provided herein are methods for reducing the rate of vestibular schwannoma tumor growth in a subject that include administering to the subject a therapeutically effective amount of one or more of: a TNFα inhibitor, an NF-kB inhibitor, an inhibitor of downstream effector of NF-kB, a COX-2 inhibitor, a HGF inhibitor, and an c-Met inhibitor.

In some embodiments, the subject is administered a TNFα inhibitor, e.g., a TNFα inhibitor selected from the group consisting of: adalimumab, infliximab, golimumab, etanercept, and certolizumab.

In addition, provided herein are methods for inducing or increasing vestibular schwannoma cell death in a subject in need thereof that include administering to a subject a therapeutically effective amount of an NF-kB inhibitor.

Further, provided herein are methods for treating, reducing the risk of, or reducing neurotoxic (e.g., ototoxic) damage to an auditory nerve, a cochlea, or a vestibular system in a subject (e.g., a subject with VS) that include administering to the subject a therapeutically effective amount of one or more of: a TNFα inhibitor, a human FGF protein, and a nucleic acid containing a sequence that encodes a FGF protein.

In some embodiments of the methods described herein, the administration is local administration, e.g., by injection through the ear drum, or direct delivery into the inner ear.

In some embodiments of the methods described herein, the administration is systemic administration.

In some embodiments of the methods described herein, the systemic administration is oral, intravenous, intraarterial, nasal, intramuscular, subcutaneous, or intraperitoneal administration.

In some embodiments of the methods described herein, the subject has been diagnosed as having vestibular schwannoma.

In some embodiments of the methods described herein, the methods include a step of identifying or diagnosing a subject as having vestibular schwannoma.

As used herein, the word "a" before a noun represents one or more of the particular noun. For example, the phrase "a vestibular schwannoma cell" represents "one or more vestibular schwannoma cells."

The term "subject" means a vertebrate, including any member of the class mammalia, including humans, rats, mice, rabbits, sports or pet animals, such as horse (e.g., race horse) or dog (e.g., race dogs), and higher primates. In preferred embodiments, the subject is a human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 6 is representing that NF-κB is aberrantly activated in derived primary VS cultures and its knockdown leads to decreased proliferation. A. NF-κB expression in cultured human VS (n≥6) normalized to expression in SC cultures (n≥6) as quantified through western blot analysis. P− means phosphorylated protein. Error bars represent SD. B. Representative image of effective transfection of a fluorescently-labeled oligonucleotide (oligo) in primary VS cells. Scale bar=50 μm. C. Representative proliferation images are shown for vehicle only (a) or siRNA (b) treated primary VS cells. BrdU in nuclei (dark grey) marks proliferating cells, nuclei are labeled with DAPI, Scale bar=100 μm; D. Quantification of proliferation changes after siRNA treatment in primary VS cells normalized to proliferation in control non-treated cells (n=4), E. Representative cell death images are shown for vehicle only (a) and siRNA (b) treated primary VS cells. TUNEL (white) in nuclei marks dying cells, nuclei are labeled with DAPI, Scale bar=100 µm; F. Quantification of cell death rate changes after siRNA treatment of primary VS cells as measured by TUNEL staining (n=3). Error bars represent SEM for panels D and F. *p<0.05, re=in comparison to.

FIG. 11 is a series of graphs and western blots demonstrating that HGF and VEGF-A pathways are aberrantly expressed and activated in VS. A. Gene expression of VEGFA and its receptor KDR, and HGF and its receptor MET, in human VS (n=8 different tumors) normalized to great auricular nerves (GAN, n=7 different nerves) as measured through qPCR. *p<0.05, **p<0.01. Error bars represent range. B. VEGF and HGF protein levels in secretions from human VS (n=21) and GAN (n=8). *p<0.05. C. Representative image of cMET expression and phosphorylation (Try 1234, P-Met) in VS, as detected by western blot (n=5). re=in comparison to.

DETAILED DESCRIPTION

Figure 1:
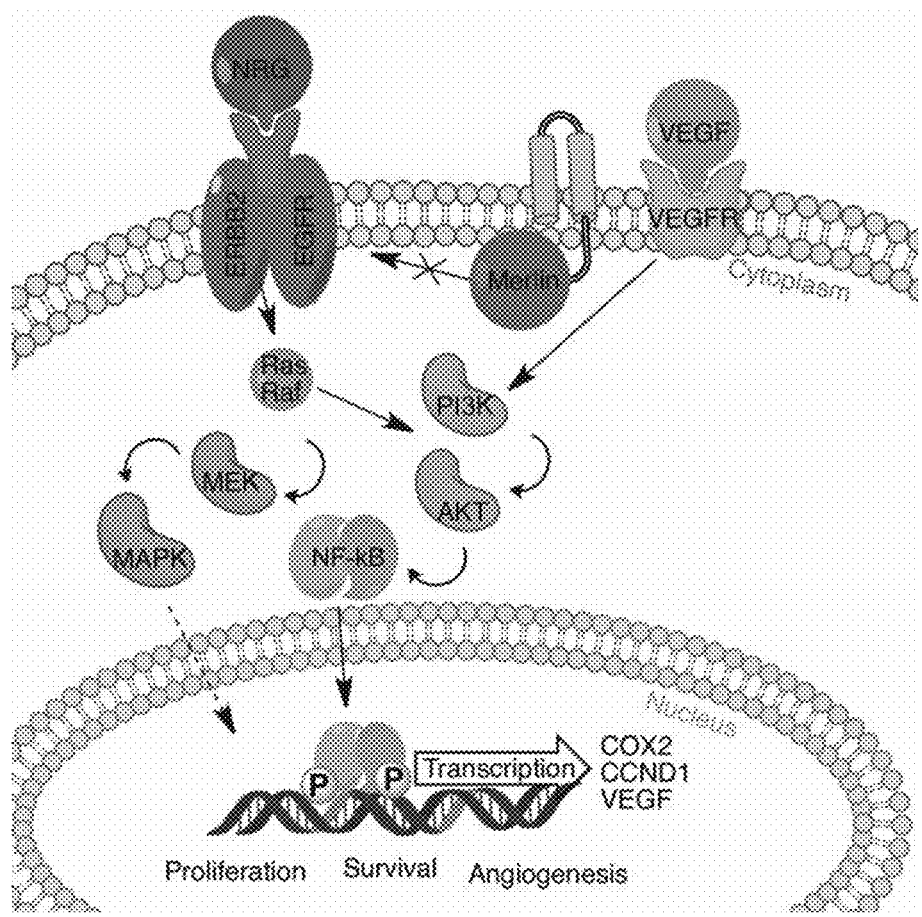
FIG. 1 is a schematic of select biological pathways important in neoplastic VS growth based on published literature (Ahmad et al., 2010; Ammoun et al., 2010; Ammoun et al., 2013; Doherty et al., 2008; Hong et al., 2011; Plotkin et al., 2009)

VSs, the most common tumors of the cerebellopontine angle, can cause substantial morbidity. There is a clinical need to develop pharmacotherapies against VS as current treatments carry significant risks. Described herein are specific pathways involved in the pathobiology of neoplastic VS growth and VS-associated SNHL and therapeutic targets that regulate neoplastic VS growth and VS-induced SNHL.

Clinical Features and Incidence of Vestibular Schwannomas (VSs)

Neoplastic Schwann cells (SCs) of the vestibular nerve lead to VSs, the fourth most common intracranial tumors. VSs, although benign in nature, can lead to various symptoms due to their crucial location within the internal auditory canal that houses the vestibulocochlear and facial nerves (Tew & McMohan, 2013). Ninety-five percent of VS patients suffer from sensorineural hearing loss (SNHL), with a smaller percentage suffering from vestibular dysfunction and facial nerve paralysis (Matthies & Samii, 1997). Further, due to their expansion into the cerebellopontine angle, VSs can lead to brainstem compression and death as the tumors grow larger (Charabi et al., 2000).

To alleviate this tumor burden, patients can undergo surgical resection or stereotactic radiotherapy. Surgical resection entails full or partial removal of the tumor via craniotomy and carries substantial risks, including SNHL, vestibular dysfunction, facial nerve paralysis, cerebrospinal fluid leaks and meningitis (Sughrue et al., 2011a; Mahboubi et al., 2014). Stereotactic radiotherapy entails delivering a radiation dose to the tumor and also carries substantial risks such as further exacerbation of the SNHL, vestibular dysfunction and malignant transformation of the tumor (Demetriades et al., 2010; Collens et al., 2011). Patients with non-growing or asymptomatic VSs can undergo conservative management and follow the tumor's progression through serial magnetic resonance imaging (MRI), but due to the lack of biomarkers for VS growth and associated symptoms, it can be a risky approach (Thakur et al., 2012). Reliable biomarkers and effective drug therapies would greatly advance health care for VS patients. In this disclosure, with an eye towards identifying effective biomarkers and pharmacotherapies, several pathobiological pathways in VS growth and VS associated SNHL were investigated.

Clinical incidence of VS has been approximately 19 per million per year (Stangerup & Cayé-Thomasen, 2012). The first VS and associated SNHL were described in 1830 by Sir Charles Bell and incidence rates have increased considerably over time, partially attributed to the advent of imaging. Although cell phone radiation-induced neoplastic transformation has been postulated, most studies investigating correlation of cell phone use with VS incidence show negative findings (Pettersson et al., 2014). Interestingly, histologic incidence for VS is approximately 1 per 500, as assessed through MRIs conducted on a group of 2000 subjects from the general population (Vernooij et al., 2007). Further, the vestibular nerve serves as a predilection site for schwannomas, with 57% of schwannomas occurring on this nerve (Propp et al., 2006). These unusually high incidence rates suggest an intriguing biology of the vestibular nerve and VS.

Within VS, there are two main classifications: VS associated with neurofibromatosis type 2 (NF2) and sporadic VS. NF2 is an autosomal dominant genetic disorder with patients developing bilateral VSs along with schwannomas, meningiomas and ependymomas at other sites (Sughrue et al., 2011b). Much more common than NF2-associated VSs, sporadic VSs make up 96% of all VSs (Neff et al., 2006). The NF2 tumor suppressor gene is mutated in all NF2 VSs (Evans et al., 2011) and in approximately 66% of sporadic VSs (Gutmann et al., 1997), although a recent study found that only one-third of the mutations were loss-of-function mutations in sporadic VSs (Lee et al., 2012). Even though a few pharmacotherapies such as bevacizumab have been clinically tested against NF2 VSs, none have been tested against sporadic VSs (Plotkin et al., 2012; Karajannis et al., 2011). This is partially because of the greater severity of the NF2 disease, with an earlier onset and a more aggressive and symptomatic multi-tumor development and progression (Evans, 2009). Due to the less aggressive nature of sporadic VS, more so well-tolerated pharmacotherapy options are needed for the benefits to outweigh the risk of side effects. For instance, bevacizumab may carry too many potential side effects such as increased risks of congestive heart failure, hypertension and arterial thromboembolic events to be relevant for patients with sporadic VSs (Choueiri et al., 2011). Therefore, it is crucial to identify additional well-tolerated pharmacotherapies against sporadic VSs.

Nonetheless, VSs, arising sporadically or in the context of NF2, have overlapping genetics, histology and clinical features (Kaye, Briggs & Morokoff, 2001; Jacoby et al., 1996), and therefore can be studied together to pre-clinically establish the most promising pharmacologic targets against sporadic and NF2-associated VSs. Pathobiological pathways were investigated in both sporadic and NF2 VSs through utilization of primary sporadic VS cultures and a NF2 VS cell line.

Pathobiology Implicated with Neoplastic Vestibular Schwannoma Growth

Considerable work has been done to understand the biological mechanisms of VS tumorigenesis and many of the prominent biological pathways and their connections are outlined in FIG. 1 (Ahmad et al., 2010; Ammoun et al., 2010; Ammoun et al., 2013; Doherty et al., 2008; Hong et al., 2011; Plotkin et al., 2009). Merlin, a membrane-bound structural protein encoded by the NF2 tumor suppressor gene, mediates contact-dependent inhibition of proliferation (Ahmad et al., 2010). Merlin can regulate several downstream biological targets associated with VS pathobiology. For example, merlin captures Na(+)/H(+) exchange regulatory cofactor (NHERF-1) associated epidermal growth factor receptor (EGFR), disabling it from receiving signals from growth factors present in the microenvironment (Lallemand et al., 2009, Cutro et al., 2011, FIG. 1).

Neuregulin (NRG), a substrate for EGFR that signals SC growth and myelinogenesis, is also upregulated in the majority of VS along with EGFR (Doherty et al., 2008). After preclinical validation through in vitro studies and in vivo work on human VS xenografts in severely compromised immuno-deficient (SCID) mice (Clark et al., 2008; Ammoun et al., 2010), researchers tested an EGFR/ErbB2 inhibitor, lapatinib, in adult and pediatric NF2 patients with progressive VSs in a phase II clinical trial (Karajannis et al., 2012). Lapatinib led to a significant decrease in tumor size and improvement in hearing in approximately 24% and 31% of the subjects, respectively. Although this was not a high response rate, the authors suggest potential improvement of the drug's access to the VS and combination therapy for higher efficacy in future studies.

Another prominent growth factor signaling pathway in VS is modulated through vascular endothelial growth factor-A (VEGF-A, FIG. 1). VEGF-A and its receptor VEGFR-1 levels correlate with growth rate in sporadic VS (Cayé-Thomasen et al., 2005). Additionally, VEGF mice harboring cranial NF2 cell line xenografts demonstrated decreased angiogenesis and tumor shrinkage with bevacizumab treatment (Wong et al., 2010). Treating NF2 VS patients with bevacizumab on a compassionate use basis led to a decrease in tumor volume and significant hearing improvement in 55% and 57% of patients, respectively (Plotkin et al., 2009; 2012).

VEGFR and EGFR receptor tyrosine kinases trigger the mitogen-activated protein kinase kinase (MEK)/mitogen-activated protein kinase (MAPK) signaling cascade, which transduces a variety of intracellular signaling to regulate proliferation, differentiation, survival and motility (Miller et al., 2012, FIG. 1). These receptor tyrosine kinases can also modulate the Phosphotidanoyisitol-3-kinase (PI3K)/Protein Kinase B (AKT) pathway that plays a role in processes such as cell survival and migration (Jacob et al., 2011, FIG. 1). Jacob et al. demonstrated that targeting the AKT pathway through a histone deactylase inhibitor in VS xenografts in SCID mice resulted in significantly reduced tumor growth.

AKT can then activate transcription factors such as nuclear factor kappa B (NF-κB) (Bai, Ueno & Vogt, 2009), leading to uncontrolled cell proliferation and survival. NF-κB has been implicated in VS previously, with its role in modulating pro-proliferative and anti-apoptotic genes (Ammoun et al., 2013). NF-κB regulates transcription of over 300 genes, including cyclooxygenase 2 (COX-2), an enzyme catalyzing prostaglandin synthesis (Gilmore, 2014; FIG. 1). COX-2 expression has been shown to positively correlate with VS growth rate (Hong et al., 2011).

Described herein is the role of several of these pathways in promoting neoplastic VS growth.

Mechanisms of Vestibular Schwannoma-Associated Sensorineural Hearing Loss

Hearing occurs when sound, traveling as air pressure waves, is mechanically transduced via the ossicles in the middle ear to a fluid pressure wave in the cochlea. The inner hair cells within the cochlea then convert the mechanical wave to neural impulses that travel along the auditory nerve to the brain. Outer hair cells amplify this signal, providing a boost in hearing of relatively softer sounds. Intact hair cells and spiral ganglion neurons are required for normal hearing. Biochemical balance in the inner ear fluids, comprised of the endolymph and perilymph in different regions of the cochlea, is required for optimal hearing.

Figure 2:
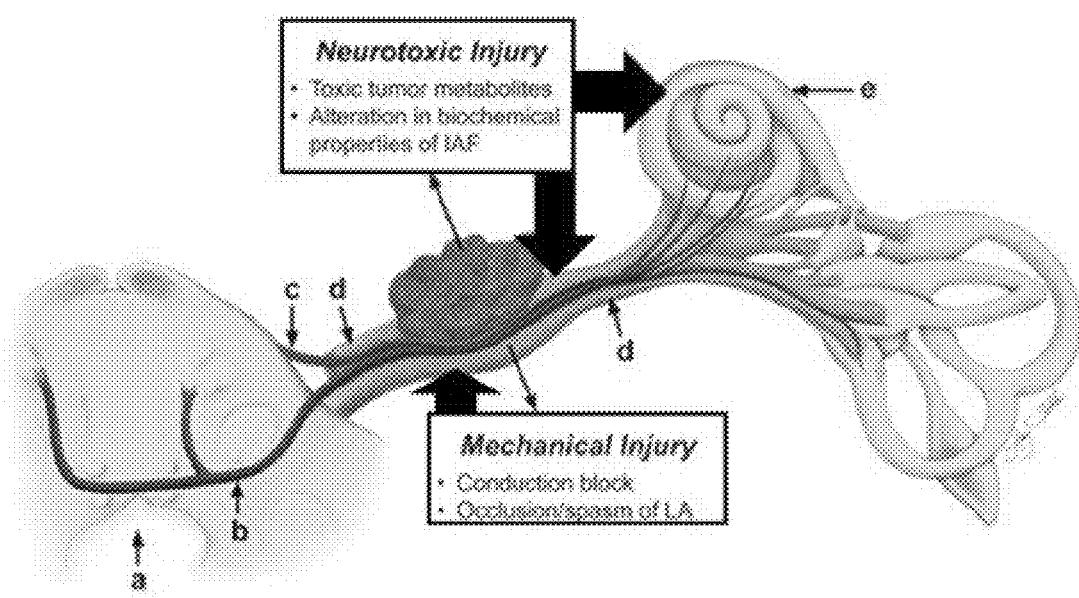
FIG. 2 is a schematic of possible mechanisms of VS associated SNHL. a=fourth ventricle; b=efferent olivocochlear tract; c=labyrinthine artery (LA); d=vestibulocochlear nerve; e=proteinaceous deposits in the inner ear fluid due to tumor metabolism; IAF=inner ear fluid. Schematic simplified from Thakur et al., 2012.

SNHL, characterized by inner ear dysfunction, is the presenting symptom for most VSs and burdens 95% of VS patients (Matthies & Samii, 1997). The mechanism behind the SNHL due to VS is currently unknown and most likely multi-factorial (Thakur et al., 2012). Most patients have cochlear dysfunction as suggested by decreased amplitudes in distortion-product otoacoustic emissions (DPOAEs), along with retrocochlear dysfunction as inferred from audiometric tests (Gouveris et al., 2007). Tumor presence does lead to ipsilateral cochlear degeneration in VS patients. Temporal bones of patients with untreated VS showed significant ipsilateral cochlear atrophy, including degeneration of organ of Corti, spiral ganglion neurons and stria vascularis (Roosli et al., 2013). It is not clear whether the cochlear or retrocochlear dysfunction precede the other. Patients with early, mild SNHL due to VS have decreased amplitude shifts in DPOAEs, indicating OHC dysfunction from the beginning of the onset of SNHL (Gouveris et al., 2007). Considering the location of VSs, the most apparent hypotheses are either SNHL due to mechanical insult from the tumor or due to ototoxic or neurotoxic biological secretions from the tumor (FIG. 2).

The mechanical effect is thought to involve either compression of the auditory nerve leading to a direct conduction block or compromise of the vascular supply to the cochlea because of an occlusion or spasm of the labyrinthine artery. The mechanical effect does not seem to explain, at least entirely, SNHL due to sporadic VSs as Nadol et al. (1996) demonstrated that the radiological dimensions of VS do not correlate with the level of SNHL in patients. Disconnect between SNHL and auditory nerve compression has been reinforced by others studies. For instance, Cayé-Thomasen et al. (2007) found the tumor's intracanalicular extent is not correlated with the degree of SNHL. A sub-set of patients develop SNHL despite the lack of VS growth. In these patients, it is most likely that oto- or neurotoxic molecules secreted from the tumor could be altering the biochemical properties of the inner ear fluid or leading to accumulation of ototoxic metabolites. The perilymphatic and endolymphatic spaces of the cochlea ipsilateral to the VS often stain positive for eosinophilic proteinaceous materials (Thakur et al., 2012).

Further, the perilymphatic protein levels are reported to be 5-15 times higher than levels in healthy individuals, a difference that was used to diagnose VS prior to the advent of MRI (Silverstein, 1972; 1973). Recent studies have found that the differential intensity of signal on varied types of MRI from the cochlea, most likely representing the protein density in the cochlea, correlates with the degree of SNHL due to NF2-related and sporadic VS (van de Langenberg et al., 2007; Asthagiri et al., 2012; Miller et al., 2014). It is important to note that NF2 VS tumor size correlates with the degree of SNHL, suggesting that mechanical compression may be an important factor in SNHL due for NF2 VSs (Asthagiri et al., 2012). Due to potential contrasting mechanisms of SNHL by NF2 and sporadic VSs, this work focused on sporadic VS associated SNHL.

A few studies have been published that suggest potential biological molecules implicated in VS. Stankovic et al. (2009) demonstrated that VS stratified by hearing have substantially different gene expression profiles, suggesting that differential expression of potentially ototoxic or otoprotective molecules may contribute to the degree of SNHL seen in VS patients. The authors found genes associated with peroxisomal dysfunction, hair cell function and others. Lassaletta et al. (2009) found that PDGF-A gene expression levels inversely correlated with SNHL in VS patients. Stankovic et al. and Lassaletta et al. explored the genetic differences leading to SNHL, and now this work explores the potential of VS secretome leading to SNHL. This is because the perilymph proteome contains differences in patients with and without VS (Lysaght et al., 2011), suggesting a role of VS-secreted molecules in modulation of cochlear cell health. No published work thus far has shown a direct effect of VS associated molecules in causing cochlear degeneration.

Plotkin et al. (2009, 2012) found that bevacizumab leads to restoration of hearing in a sub-set of NF2 VS patients, independent of its decrease in tumor size. It is intriguing because this type of hearing improvement has also been noted when using other therapies such as lapatinib, although in a smaller percentage of patients (Karajannis et al., 2012). The effect was similar, in that the hearing improvement was disconnected from reduction in VS size. A remarkable aspect of these studies is the hearing improvement (rather than prevention of further SNHL) since the major cell types required for hearing, i.e. hair cells or spiral ganglion neurons, do not regenerate. It may be that these therapies are alleviating edema-induced interference of cochlear nerve function or rescuing function of slowly degenerating cochlear and neural structures.

Described herein is the role of VS-secreted factors in SNHL. Using specific factors causatively shown to be involved in VS associated SNHL, clinicians could predict the likelihood of the SNHL for a given patient and prescribe therapies that modulate those factors.

Figure 26:
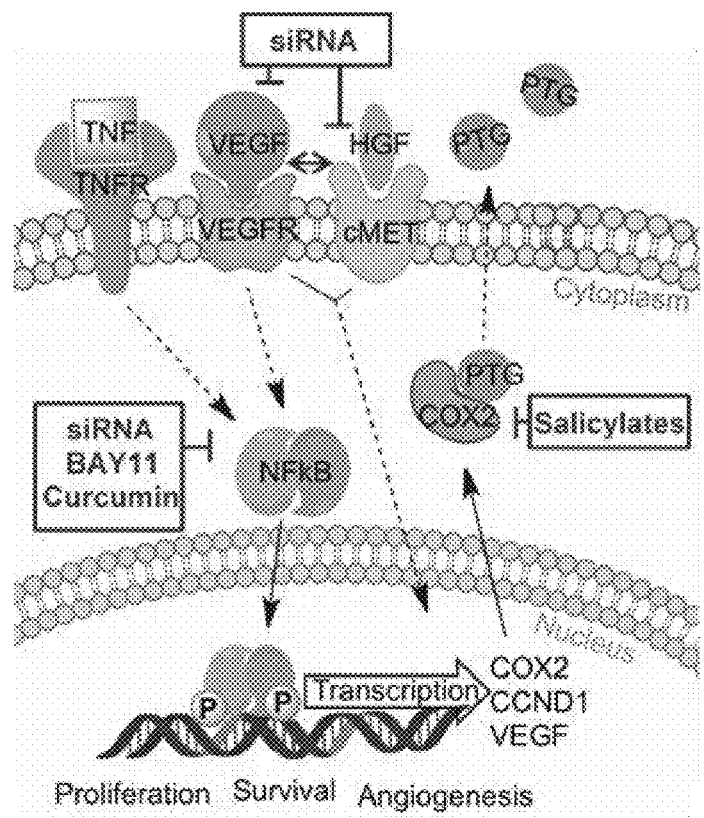
FIG. 26 is a schematic of VS pathobiological pathways studied, with potential connections. All molecules' aberrant expression was established or validated and therapeutic inhibition (boxes) of specific pathways was assessed in this work. Dashed lines indicate intermediate interactions.

Without wishing to be bound by theory, an exemplary summary of biological pathways investigated herein is shown in FIG. 26. We have explored the role of two major inflammatory regulators in VS growth using primary human VS cultures. We investigated the role of NF-κB, a pro-inflammatory transcription factor, in promoting growth and survival and have identified a few experimental and clinical inhibitors that show efficacy specifically against VS cells. Additionally, we have established the aberrant expression of COX-2 in VS and demonstrated efficacy of salicylates in inhibiting VS cell proliferation. We have also identified cross-talk between angiogenic molecules VEGF-A and cMET in VS and SCs, providing insight into how VEGF-A interacts with other molecules and potentially the mechanism behind therapeutic efficacy of its blockade in VS patients.

Investigating the potential biochemical mechanism of SNHL due to VS, we have identified ototoxic TNFα and otoprotective FGF2 secreted from VS. We have also demonstrated, using a cochlear explant model, that VS secreted factors can cause damage to the cochlear cells; different VSs lead to differential degree and type of damage. Further, this degeneration can be partially rescued by neutralizing TNFα.

Use of Fresh VS and GAN Specimens and Primary Cultures to Study VS Pathobiology Associated with Tumor's Growth and SNHL A strength of the present disclosure is the utilization of fresh human surgical specimens. Advantages of fresh surgical VS specimens over transformed cell lines are that signaling pathways are more representative of those in situ, and that heterogeneity among different tumors can be studied. Further, the specimens were used to develop primary cultures, using a method that avoids mitogens, cytotoxins and potentially transformative techniques. We noted a high degree of biological similarity between the parent VSs and the derived culture, affirming the culture model as representative of the parent tissue. Noting some biological differences between the parent tissue and derived cultures, we realize the important of confirming the aberrant expression of the biological pathway of interest in both fresh surgical specimens and derived cultures. This validation step was conducted for all pathways studied in this work.

We chose GANs as the control nerves because schwannomas are exceptionally rare on this sensory nerve, pathology-free GANs are readily available as they are commonly sacrificed during neck dissections, and GANs have been successfully utilized as negative controls in previous VS studies (Doherty et al., 2008). In order to translate our findings to NF2 VSs, we studied many of the pathways in the NF2 VS cell line as well. The cell line exhibited a different dosage response to many of the inhibitors, potentially due to the transformed nature of the cells or due to biological differences between sporadic and NF2 VSs.

When studying VS-associated SNHL, we also employed fresh VS specimens. This enabled us to collect secretions from VS that would closely resemble tumors' secretome in vivo and capture the intertumor heterogeneity. Using these samples, we could correlate the expression of different molecules and the extent of SNHL in VS patients. Further, we could apply these secretions onto cochlear explant cultures to develop the first model to causatively study SNHL due to VS.

Therapeutic Inhibition of Inflammatory Pathways in Neoplastic VS Growth

Several studies have identified the immunogenic potential of tumors (Hoesel & Schmid, 2013) and specifically that of VSs. Rossi et al. (1990) have described the presence of macrophages and CD8-positive and CD4-positive lymphocytes in VS. More recently, deVries et al. (2013) have observed the correlation of the degree of CD163-positive tumor associated macrophage infiltration with VS proliferation rate. The role of inflammation in neoplastic growth is complex, and much is still unknown. Typical physiological inflammatory responses and pathological responses exhibited by neoplasms can have many overlapping features (Hoesel & Schmid, 2013). Previous work has focused on specific molecular pathways in order to dissect the differences and identify the most promising therapeutic targets.

Although the presence of inflammatory cells and certain pro-inflammatory molecular pathways have been implicated in VS, these pathways have not been therapeutically explored. For example, NF-κB was found to be aberrantly activated via Axl/Gas6 signaling and siRNA-mediated NF-κB knockdown led to decreased VS cell proliferation, survival and cell matrix adhesion (Ammoun et al., 2013). Similar to the results by Ammoun et al., we found the siRNA-mediated knockdown of NF-κB led to decreased proliferation and a trend of decreased survival in primary VS cells and the NF2 cell line. We also discovered another inducer of NF-κB to be significantly upregulated in VS, namely TNFα (FIG. 26). TNFα has been implicated in many neoplasms previously, although it is novel in VS (Balkwill, 2009). Additionally, we found that NF-κB inhibition via an experimental inhibitor, BAY11, and clinically-relevant inhibitor curcumin, led to decreased VS growth and survival in primary VS cells and the NF2 VS cell line.

Figure 10:
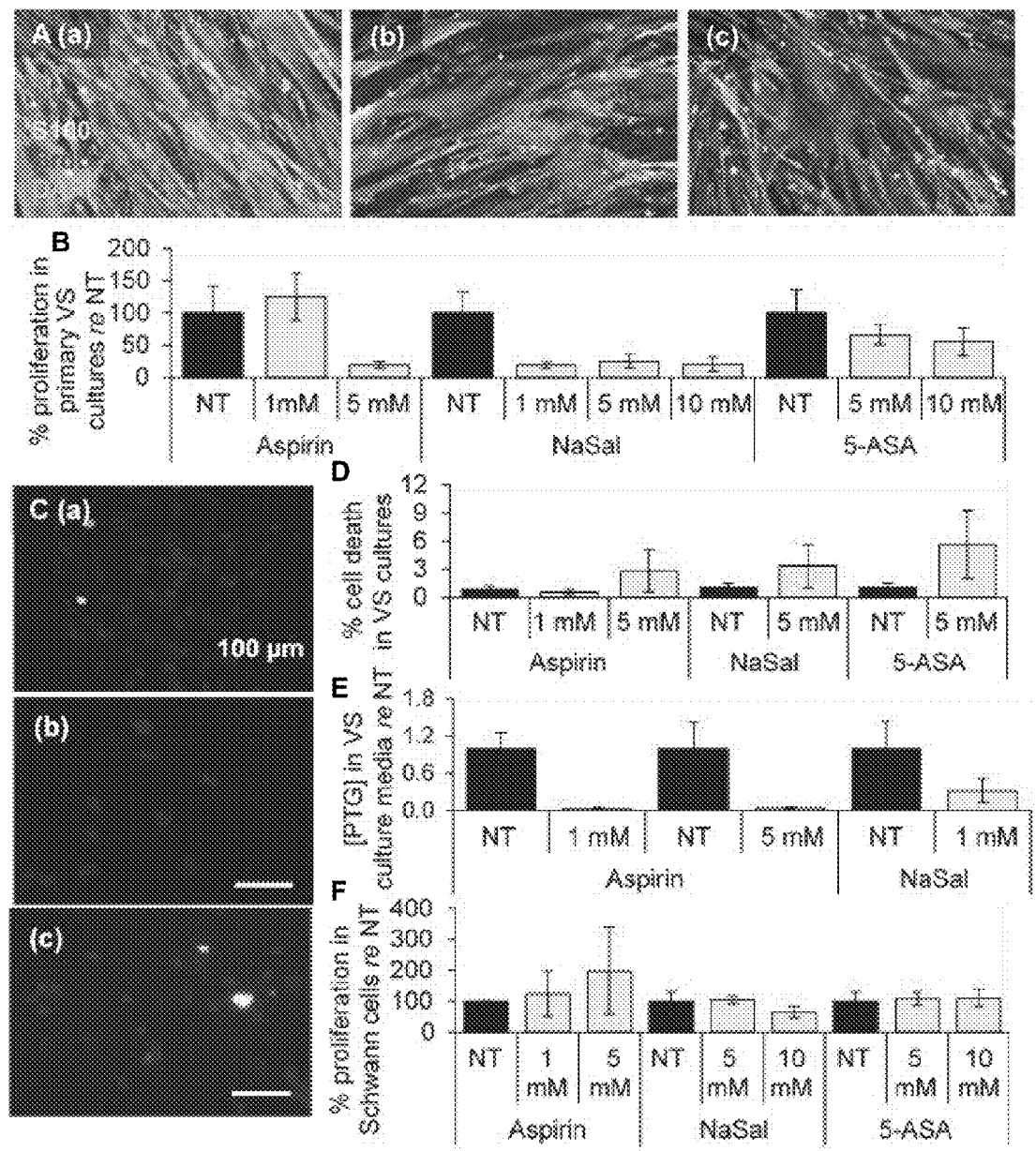
FIG. 10 is a collection of images and bar graphs indicating that salicylates lead to decreased proliferation selectively in VS cells. A. Representative VS culture proliferation images are shown after treatment for no treatment control (a, NT), 5 mM Aspirin (b), and 1 mM NaSal (c). S100 marks schwannoma cells, BrdU in nuclei marks proliferating cells. Nuclei are labeled with DAPI. Scale bar=100 µm for all images. B. Quantification of proliferation changes after treatment with Aspirin, NaSal and 5-ASA in primary VS cells normalized to proliferation in NT cells (n≥5), C. Representative VS culture cell death images are shown after treatment for NT (a), 5 mM aspirin (b), and 5 mM NaSal (c). TUNEL (light grey) marks dying cells. Nuclei are labeled with DAPI, Scale bar=100 µm for all images; D. Quantification of cell death rate changes after treatment with Aspirin, NaSal and 5-ASA in primary VS cells (n≥3 for each); E. Secreted PTG levels in VS culture media after treatment for NT, 5 mM aspirin, 1 mM and 5 mM NaSal (n≥3); Error bars represent SD. F. Quantification of proliferation changes after treatment with aspirin, NaSal and 5-ASA in primary SCs normalized to proliferation in NT cells (n≥3), *p<0.05. re=in comparison to. Error bars represent SEM.

The expression of COX-2, another inflammatory mediator, was also found to correlate with VS proliferation rate (Hong et al., 2011). We affirmed this aberrant expression of COX-2 expression in VS and further utilized clinically relevant COX-2 inhibiting salicylates in primary VS cells (FIG. 10.1). We found aspirin, sodium salicylate and 5-aminosalicylic acid to inhibit proliferation specifically in VS cells, sparing SCs. In a retrospective clinical study, we found that aspirin intake correlated with halted VS growth (see Kandathil et al., 2014, which is incorporated herein by reference in its entirety). Both studies found a cytostatic effect of aspirin against VS cells.

To expedite translation of the present treatment for VS patients, we used clinically-relevant NF-κB and COX-2 inhibitors. Curcumin and the salicylates have been effectively used clinically, with a minimal toxicity profile if used within the therapeutic range. Even though these inhibitors may have other targets in addition to NF-κB or COX-2, other targets such as TNFα in the case of curcumin or NF-κB in the case of salicylates are involved in pathological inflammation. These inhibitors are promising pharmacotherapies against VS as they show selective efficacy against VS cells. Further, targeting inflammation in VS more generally could be efficacious.

Studying Angiogenesis Pathways Regulating Neoplastic VS Growth

We also explored angiogenic pathways in VS growth. We focused on VEGF-A, a well-known angiogenic mediator in VS, and its relationship to another angiogenic pathway, HGF/cMET signaling. We discovered cross-talk between the VEGF-A and cMET pathways, with siRNA-mediated knockdown of either VEGF-A or cMET leading to decreased levels of the other in VS and SCs (FIG. 26). This was intriguing because it provides insight that molecules such as VEGF-A may not be acting alone in vivo, and their targeted inhibition could be leading to modulation of other biological pathways. It also provides insight into potential resistance mechanisms, in which initially dependent co-regulation of VEGF-A and cMET could become independent, providing tumors new ways to continue unregulated neoplastic growth. We also show, for the first time, therapeutic efficacy of cMET inhibition in sporadic VS cells. Intriguingly, these angiogenic pathways could be acting via the inflammatory pathways (FIG. 26).

Cumulative Role of Individual Pathways in the Pathobiological VS Interactome

Since many pathways have been proposed in VS pathobiology, it is important to build an interactome that could simplify the complex pathobiological picture in neoplastic growth. This disclosure interconnects pathways that may seem to be working independently in VS, exploring connections previously described in other cell types. This can enable us to identify pharmacotherapies capable of targeting several pathways, increasing efficacy and reducing long term drug resistance. Among the inflammatory pathways studied, a well-known connection between COX-2 and NF-κB exists as COX-2 has a κB binding site (FIG. 26). Previous studies have shown decreased PTG levels after BAY11 treatment (Lee et al., 2012), a trend we have also noted in our preliminary work. Further, VEGF-A expression can also be regulated by NF-κB (Leychenko et al., 2011) and VEGF-A can activate NF-κB (Marumo, Schini-Kerth & Busse, 1999) (FIG. 26). Interestingly, Bradbury et al. found that PTGs, the product of COX-2, increased VEGF-A levels in granulomas (Bradbury et al., 2005).

It was interesting to note that VS cells exhibited NF-κB activation without the need of a stimulus such as exogenous TNFα application. This was also the case for healthy SCs but to a significantly lesser extent, with the SCs most likely exhibiting basal, ubiquitous NF-κB activation that is not affected by NF-κB inhibitors such as BAY11 (Pierce et al., 1997). This autologous activation in VS cells suggests that they have the ability to activate NF-κB through cytokines or growth factors such as VEGF-A and TNFα, which is then sustained by NF-κB promoting transcription of such factors that will continue to keep it activated, sustaining independent neoplastic growth. Although we found TNFα to be highly expressed in VS, previous work suggests another regulatory pathway for NF-κB, namely Axl/Gas6 signaling (Ammoun et al., 2013). It may be that these two signaling molecules, along with potentially others, can lead to constitutive activation of NF-κB and therefore we note NF-κB activation in essentially all tumors studied. Rather than potentially targeting Axl or TNFα, it may be more therapeutic to target NF-κB directly.

Connecting different pathways provides a broader view of VS pathobiology and highlights the interconnectedness one should consider when exploring the most promising pharmacotherapies. Our work motivates exploration of interdependence of other pathways in VS.

With the hope of providing well-tolerated pharmacotherapies against VS, we utilized clinically-relevant inhibitors. We chose drugs that cross the blood-brain barrier, have shown efficacy against central nervous system diseases, and meet the therapeutic-toxic profile for sporadic VS patients. Our selection of drugs is further supported by our clinical retrospective study in which patients were safely taking aspirin at dosages that seem to be efficacious against VS (Kandathil et al., 2014). Our in vitro and clinical findings motivate future prospective randomized clinical trials for salicylates for sporadic VS patients.

Unraveling the major targets of these drugs can provide additional drugs that may have a higher effectiveness against VS, with even further decreased side effects. In the case of BAY11 or curcumin, it will be important to understand if NF-κB inhibition is the sole component leading to their efficacy. If other targets are discovered, BAY11 or curcumin's efficacy could be potentially increased by combination therapy with another NF-κB inhibitor. In the case of COX-2, it would also be important to try COX-2-selective inhibitors such as celecoxib as these compounds further curb the side effects of general COX inhibitors (Solobweski et al., 2010).

Tumor-Secreted Factors as Potential Source of SNHL Due to VS

We demonstrate, for the first time, that VS secreted factors can damage and destroy cochlear cells. Although the presence of VS-secreted ototoxic and neurotoxic substances has been postulated, we prove their existence using a cochlear culture model in our work.

Figure 27:
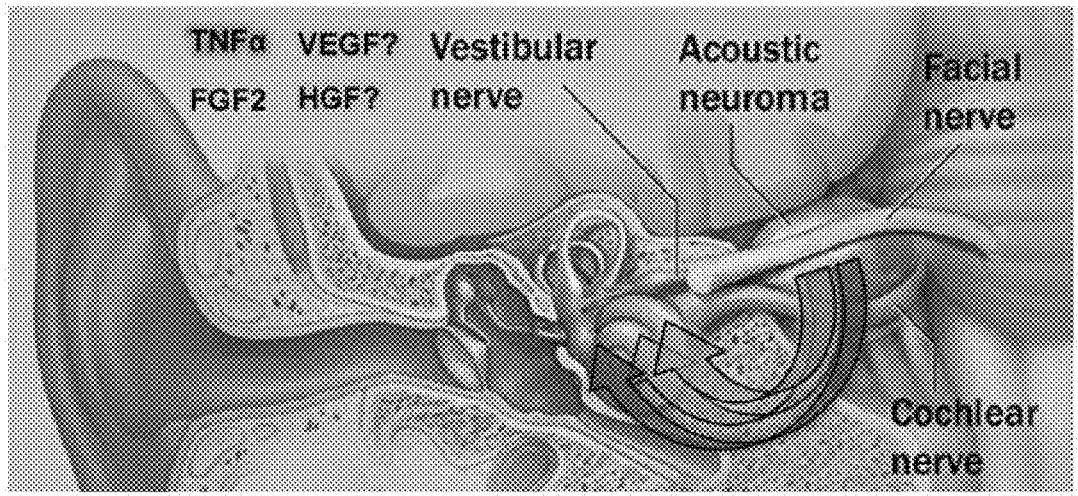
FIG. 27 is a schematic of VS secreted molecules modulating SNHL. Molecules with ototoxic or otoprotective potential reaching the nearby cochlea and auditory nerve is schematized using arrows. The effect of some molecules (HGF and VEGF) is not clear.

We focused on several different molecules to understand their role in VS associated SNHL, namely FGF2, TNFα, VEGF-A and HGF (FIG. 27). All these molecules are growth factors implicated in neoplastic growth. Based on previous work and our findings, they seem to play crucial roles in VS pathobiology. Each molecule had a unique expression profile in the different VS secretions analyzed.

These molecules, along with others, may have a linear or non-linear additive effect which may result in an overall environment with a certain degree of ototoxicity. For instance, VEGF-A neutralization in VS-C secretions led to partial rescue of neurite loss, albeit a small effect.

Contrastingly, FGF2, an oto- and neuroprotective molecule (Zhai et al., 2002; 2004) can rescue neurite loss from different insults, including in the context of gentamicin treatment as seen in our work. As VS-C secreted high levels of VEGF-A and FGF2, it could be possible that removal of VEGF-A enables FGF2 to exert its protective role in maintaining neurites. Further, it was interesting to note that VEGF-A and TNFα's ototoxic effects are more apparent at the apical and basal turns, respectively, suggesting that these molecules may be acting at different regions of the cochlea.

In addition to VEGF-A, TNFα and FGF2, there may be other molecules that are regulating different aspects of cochlear degeneration due to VS. For example, Stankovic et al. (2009) and Lassaletta et al. (2009) identified expression of genes such as PEX5L and PDGFA to be inversely correlated with SNHL due to VS, suggesting additional otoprotective factors. Additionally, we found that VEGF-A inversely modulates HGF levels in murine cochlear explants. HGF has a known otoprotective role (Kikkawa et al., 2009; Schultz et al., 2009). It could be possible that many ototoxic and otoprotective molecules are regulated by each other, as we have found for VEGF-A and HGF. This type of modulation has been noted in other systems such as the retina in zebrafish, where several secreted molecules are regulated by other secreted molecules to have an overall regenerative effect (Gorsuch & Hyde, 2013).

Divergent Biological Pathway Regulation in VS Cells Versus Cochlear Cells

It was interesting to note the apparently contrasting trends in the human primary VS cultures and in cochlear explant cultures, based on previous findings and our work. In the human model, VEGF-A knockdown led to decreased cMET. In the murine cochlear explant cultures, exogenous VEGF-A application led to decreased HGF, and VEGF-A inhibition in VS secretions led to further increased HGF. This variation may be attributable to the difference in cell types. This could also be due to interspecies differences or due to paracrine versus autocrine signaling. This opposing trend seems to be also present between TNFα and NF-κB. In some cell types, including certain stages of neoplastic growth, TNFα induces NF-κB activation, leading to increased proliferation and survival (Beg et al., 1993; Balkwill, 2009). In other cell types, including cochlear cells, TNFα application leads to apoptosis by inhibiting NF-κB activation. Haake et al. showed the dexamethasone counteracts TNFα-induced apoptosis in hair cells by activating NF-κB and increasing expression of downstream survival genes (Haake et al., 2009). This dual contrasting role of TNFα in VS cells versus cochlear cells makes it an ideal molecular target to alleviate tumor burden due to VS as it can be targeted to inhibit VS growth and minimize associated SNHL. Further, being a key inflammatory cytokine, TNFα highlights how inflammation regulated by the tumor could be enabling neoplastic VS growth and the associated SNHL independently.

Since there are no predictors of SNHL due to VS currently, FGF2 and TNFα could serve as biomarkers if their levels in serum or cerebrospinal fluid correlate with the degree of SNHL in VS patients. As the role of more proteins in SNHL due to VS is elucidated, it could be an array of biomarkers measured in the tumor microenvironment, such as by sampling blood serum or cerebrospinal fluid, which provides an accurate prognosis of the likelihood of SNHL in patients with VS, which would influence counseling and surgical decision making. For therapeutic translation, modulation of the molecules identified in our work will have to be assessed carefully due to their dual roles in hearing and VS growth. Our findings highlight anti-TNFα therapy due to TNFα's potential role in VS growth and SNHL and due to clinically established drugs targeting TNFα. Anti-TNFα therapy, namely infliximab, has been safe and effective when administered locally and systemically for SNHL due to autoimmune inner ear disease (Lobo et al., 2013). Along with being otoprotective and neuroprotective, FGF2 can promote VS growth. A possibility to utilize FGF2 against SNHL would be to modify FGF2's structure to solely retain its otoprotective properties while minimizing its proliferation properties.

For VEGF-A, although clinical results show hearing improvement after bevacizumab therapy for NF2 patients, the mechanism behind bevacizumab's efficacy in improving SNHL is not clear. Trends of neurite loss with VEGF-A independently and rescue with VEGF-A neutralization in VS secretions may explain the potential mechanism of anti-VEGF-A efficacy in VS patients, although these effects were small and insignificant. Experiments with more tumors and larger sample sizes will be necessary to confidently assess this trend. It could also be that VEGF-A inhibition relieve edema-associated interference of the auditory nerve.

Overall, several pathways in VS pathobiology that contribute to either VS growth or VS associated SNHL were identified or validated. Manipulation of these pathways through experimental and clinically relevant inhibitors identified promising biological targets to minimize tumor burden in VS patients.

Methods of Treatment

This invention discloses the role of and therapeutic inhibition of specific inflammatory and growth modulators in VS and the potential of VS-secreted growth factors in modulating SNHL, e.g., SNHL in VS. Thus, the methods described herein can be used to treat subjects with VS, including subjects with VS who have or are at risk of developing VS-associated SNHL. The methods include administering a therapeutically effective concentration of one or more of: a TNF-α inhibitor (e.g., any of the exemplary TNFα inhibitors described herein or known in the art), an NF-κκB inhibitor (e.g., any of the exemplary NF-κB inhibitors described herein or known in the art), an inhibitor of downstream effector of NF-κB (e.g., any of the downstream effectors of NF-κB described herein or known in the art), a COX-2 inhibitor (e.g., any of the exemplary COX-2 inhibitors described herein or known in the art), a HGF inhibitor (e.g., any of the HGF inhibitors described herein or known in the art), and an c-Met inhibitor (e.g., any of the c-Met inhibitors described herein or known in the art).

The term "TNFα inhibitor" is art known and means an agent that specifically decreases the levels of TNFα mRNA (e.g., human TNFα mRNA) and/or protein (e.g., human TNFα protein), and/or specifically decreases the activity of TNFα protein (e.g., human TNFα protein). Non-limiting examples of a TNFα inhibitor include inhibitory nucleic acids as described herein; adalimumab, infliximab, golimumab, etanercept, pentoxyfyllene, and certolizumab pegol. Additional examples of TNFα inhibitors are described in Jackson (Dermatol. Ther. 20:251-264, 2007), Dogra et al. (Indian J. Dermatol. Venereol. Leprol. 79:S35-S46, 2013), Nielsen et al. (N. Eng. J. Med. 369:754-762, 2013), Nielsen et al. (BMC Med. 11:174, 2013), He et al. (Science 310: 1022-1025, 2005), and Haraguchi et al. (AIDS Res. Ther. 3:8, 2006). Additional examples of TNFα inhibitors include small interfering RNAs (siRNAs), antisense molecules, and ribozymes designed to target and decrease the levels of TNFα mRNA (e.g., in a mammalian cell, e.g., a mammalian cell in a human subject). In some embodiments of any of the methods described herein, the TNFα inhibitor is not a naturally occurring molecule (e.g., not present naturally in a human or produced by a human body).

The term "NF-κB inhibitor" is art known and means an agent that specifically decreases the levels of an mRNA encoding one or the two protein subunits of NF-κB (e.g., human NF-κB) and/or NF-κB protein (e.g., human NF-κB) levels, and/or specifically decreases the activity of NF-κB activity (e.g., human NF-κB). Non-limiting examples of NF-κB inhibitors include inhibitory nucleic acids as described herein; BAY11-7082, curcumin, azithromycin, conophylline, MOL 294, pigment epithelium derived factor, perrilyl alcohol, MAST205, rhein, 15-deoxy-prostaglandin J(2), palmitoylethanolamide, NSC697923, Antrodia camphorata extract, apigenin, aresenic trioxide, chromian picolinate/histidinate, surfactant protein A, DQ 65-79, cysteamine, C5a, mycoepoxydiene, alphapinene, ometin, R-etodolac, SR141716, dioxin, alginic acid, allopurinol, apilimod, atorvastatin, azacitidine, N(1)-benzyl-4-methylbenzene-1,2-diamine, carbaryl, captopril, carnostic acid, celastrol, chiisanoside, corilagen, CP-1158, dehydroxymethaylepoxygionomicin, 15-deoxyspergualin, dipryidamole, disulfiram, diltiazem, ERB-041, eutigoside C, florfenicol, betafenaltrexamine, hirsutenone, indole-3-carbinol, JM34, JSH-23, KIOM-79, KL-1156, leptomycin B, levamisole, lidamycin, MEB, methimazole, montelukast, 2',8"-biapigenin, oregonin, pergoglide, phallacidin, pimecrolimus, piperine, pitavastatin, PN-50, POP2, pravastatin, propofol, rolipram, SC236, selenomethionine, sorafenib, cornuside, sopoongsan, sphondin, thymulin, violaxathin, clarithromycin, fluvastatin, leflunomide, AT514, azithromycin, canthaidin, neomycin, rapamycin, triflusal, verbascoside, zoledronic acid, 1'-acetoxychavicol acetate, 2-acetylaminofluorene, adiponectin, albaconol, amrinone, artesunate, arzanol, atrovastat, baicalein, campthothecin, candesartan, caprofen, capsiate, carbocisteine, flubiprofen, flutamide, folymycin, myricetin, moxifloxacin, rapomycin, raloxifene, raxofelast, rebamipide, ritonavir, rosiglitazone, roxithromycin, silibinin, sulfasalazine, temozolomide, mesalamine, tetrandrine, luteolin, telithromycin, trilinolein, troglitazone, wortmanin, rifampicin, sulindac, tomatidine, vernarinone, amentoflavone, glimepiride, midazolam, and NSAIDs. Additional examples of NF-κB inhibitors are known in the art. Additional examples of NF-κB inhibitors include small interfering RNAs (siRNAs), antisense molecules, and ribozymes designed to target and decrease the levels of TNFα mRNA (e.g., in a mammalian cell, e.g., a mammalian cell in a human subject). In some embodiments of any of the methods described herein, the NF-κB inhibitor is not a naturally occurring molecule (e.g., not present naturally in a human or produced by a human body). For example, in some embodiments an inhibitory nucleic acid targeting NF-κB can target any of the subunits of NF-kB, e.g., NFKB1/p105, RELA/p65, REL, NFKB2/p52, or RELB.

The term "COX-2 inhibitor" is art known and means an agent that specifically decreases the levels of a mRNA encoding of COX-2 (e.g., human COX-2 protein) and/or COX-2 protein levels (e.g., human COX-2 protein), and/or specifically decreases the activity of COX-2 activity (e.g., human COX-2 protein). Non-limiting examples of COX-2 inhibitors include inhibitory nucleic acids as described herein; aspirin, sodium salicylate, 5-amino salicylic acid, indomethacin, ibuprofen, naproxen, piroxicam, nabumetone, valdecoxib, rofecoxib, and celecoxib. Additional examples of COX-2 inhibitors are known in the art. Additional examples of COX-2 inhibitors include small interfering RNAs (siRNAs), antisense molecules, and ribozymes designed to target and decrease the levels of COX-2 mRNA (e.g., in a mammalian cell, e.g., a mammalian cell in a human subject). In some embodiments of any of the methods described herein, the COX-2 inhibitor is not a naturally occurring molecule (e.g., not present naturally in a human or produced by a human body).

The term "c-Met inhibitor" is art known and means an agent that specifically decreases the levels of a mRNA encoding c-Met protein (e.g., human c-Met) and/or c-Met protein (e.g., human c-Met) levels, and/or specifically decreases the activity of c-Met. Non-limiting examples of c-Met inhibitors include inhibitory nucleic acids as described herein; cabozantinib, foretinib, JNJ-38877605, PF-04217903, MK2461, GSK 1363089, AMG 458, tivantinib, INCB28060, PF-02341066, E7050, BMS-777607, ARQ197, GSK/1363089/XL880, and XL184. Additional examples of c-Met inhibitors are known in the art. Additional examples of c-Met inhibitors include small interfering RNAs (siRNAs), antisense molecules, and ribozymes designed to target and decrease the levels of c-Met mRNA (e.g., in a mammalian cell, e.g., a mammalian cell in a human subject). In some embodiments of any of the methods described herein, the c-Met inhibitor is not a naturally occurring molecule (e.g., not present naturally in a human or produced by a human body).

The term "HGF inhibitor" is art known and means an agent that specifically decreases the levels of a mRNA encoding HGF protein (e.g., human HGF protein) and/or HGF protein (e.g., human HGF protein) levels, and/or specifically decreases the activity of HGF (e.g., human HGF protein). Non-limiting examples of HGF inhibitors include inhibitory nucleic acids as described herein; truncated HGF proteins such as NK1 (N terminal domain plus kringle domain 1) (see, e.g., Lokker et al., J. Biol. Chem. 268:17145, 1993), NK2 (N terminal domain plus kringle domains 1 and 2) (see, e.g., Chan et al., Science 254:1382, 1991), and NK4 (N-terminal domain plus four kringle domains) (see, e.g., Kuba et al., 30 Cancer Res. 60:6737, 2000); an antibody that specifically binds to HGF protein (e.g., human HGF protein) (e.g., 5D5, a single domain form of 5D5 (see, e.g., Nguyen et al., Cancer Gene Ther. 10:840, 2003), L2G7, L2G7 (Kim et al., Clin. Cancer Res. 12:1292, 2006, and U.S. Pat. No. 7,220,410), HuL2G7 (see, e.g., WO 07115049 A2), the human mAbs described in WO 2005/017107 A2, and the HGF binding proteins described in WO 07143090 A2 or WO 07143098 A2). Additional examples of HGF inhibitors include small interfering RNAs (siRNAs), antisense molecules, and ribozymes designed to target and decrease the levels of HGF mRNA (e.g., in a mammalian cell, e.g., a mammalian cell in a human subject). In some embodiments of any of the methods described herein, the HGF inhibitor is not a naturally occurring molecule (e.g., not present naturally in a human or produced by a human body).

The term "inhibitor of downstream effector of NF-κB" means an agent that specifically decreases the levels of a mRNA encoding protein that acts downstream in a NF-κB signaling pathway (e.g., human cyclin D1, human Bcl2, or human REL protein) and/or the levels of a protein that acts downstream in a NF-κB signaling pathway (e.g., human cyclin D1, human Bcl2, or human REL protein), and/or specifically decreases the activity of a protein that acts downstream in a NF-κB signaling pathway (e.g., human cyclin D1, human Bcl2, or human REL protein). For example, a protein that acts downstream in a NF-κN signaling pathway include cyclin D1, Bcl2, and REL.

Any of the proteins or mRNAs described herein can be, e.g., the human protein or mRNA. Human TNFα protein is, e.g., Genbank No. ADV31546.2, and human TNFα cDNA is, e.g., Genbank No. HQ201306.2.

Inhibitory Nucleic Acids

In some embodiments, the methods and compositions described herein can include inhibitory nucleic acids targeting TNF-α, NF-κB, COX-2, HGF, or c-Met.

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), ribozymes, and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112; Burnett and Rossi (2012) Chem Biol. 19 (1):60-71.

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range there within.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 8,604,192; 8,697,663; 8,703,728; 8,796,437; 8,865,677; and 8,883,752 each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N (CH3)-CH2, CH2-N(CH3)-N(CH3)-CH2 and O—N(CH3)-CH2-CH2 backbones, wherein the native phosphodiester backbone is represented as O—P—O—CH); amide backbones (De Mesmaeker (1995) Ace. Chem. Res. 28:366-374); morpholino backbone structures (Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, Nielsen (1991) Science 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, phosphonoacetate phosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey (2002) Biochemistry 41(14), 4503-4510); Genesis, volume 30, issue 3, 2001; Heasman, (2002) Dev. Biol. 243, 209-214; Nasevicius (2000) Nat. Genet. 26, 216-220; Lacerra (2000) Proc. Natl. Acad. Sci. 97, 9591-9596; and U.S. Pat. No. 5,034,506, issued Jul. 23, 1991. Cyclohexenyl nucleic acid oligonucleotide mimetics are described in Wang (2000) Am. Chem. Soc. 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,677,439; and 8,927,513 each of which is herein incorporated by reference.

One or more substituted sugar moieties can also be included, e.g., one of the following at the 2' position: OH, SH, $SCH_3$, F, OCN, $OCH_3$, $OCH_3O(CH_2)nCH_3$, $O(CH_2)nNH_2$ or $O(CH_2)nCH_3$ where n is from 1 to about 10; C1 to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy[2'-0-$CH_2CH_2OCH_3$, also known as 2'-O-(2-methoxyethyl)] (Martin (1995) Helv. Chim. Acta 78, 486). Other preferred modifications include 2'-methoxy (2'-0-$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, 2,6-diaminopurine; 5-ribosyluracil (Carlile (2014) Nature 515(7525): 143-6). Kornberg, A., DNA Replication, W. H. Freeman & Co., San Francisco, 1980, pp 75-77; Gebeyehu (1987) Nucl. Acids Res. 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide. In some embodiments, both the nucleobase and backbone may be modified to enhance stability and activity (El-Sagheer (2014) Chem Sci 5:253-259)

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen (1991) Science 254, 1497-1500; and Shi (2015).

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat.

No. 3,687,808, as well as U.S. Pat. Nos. 4,845,205; 5,130,302; 5,134,066; 5,175, 273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger (1989) Proc. Natl. Acad. Sci. USA 86, 6553-6556), cholic acid (Manoharan (1994) Bioorg. Med. Chem. Let. 4, 1053-1060), a thioether, e.g., hexyl-S-tritylthiol (Manoharan (1992) Ann. N. Y. Acad. Sci. 660, 306-309; Manoharan (1993) Bioorg. Med. Chem. Let. 3, 2765-2770), a thiocholesterol (Oberhauser (1992) Nucl. Acids Res. 20, 533-538), an aliphatic chain, e.g., dodecandiol or undecyl residues (Kabanov (1990) FEBS Lett. 259, 327-330; Svinarchuk (1993) Biochimie 75, 49-54), a phospholipid, e.g., di-hexadecyl-rac-glycerol or triethylammonium 1,2-di-O-hexadecyl-rac-glycero-3-H-phosphonate (Manoharan (1995) Tetrahedron Lett. 36, 3651-3654; Shea (1990) Nucl. Acids Res. 18, 3777-3783), a polyamine or a polyethylene glycol chain (Mancharan (1995) Nucleosides & Nucleotides 14, 969-973), or adamantane acetic acid (Manoharan (1995) Tetrahedron Lett. 36, 3651-3654), a palmityl moiety (Mishra (1995) Biochim. Biophys. Acta 1264, 229-237), or an octadecylamine or hexylamino-carbonyl-t oxycholesterol moiety (Crooke (1996) J. Pharmacol. Exp. Ther. 277, 923-937). See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941, 8,865,677; 8,877,917 each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to the target lncRNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a lncRNA, then the bases are considered to be complementary to each other at that position. 100% complementarity is not required.

In some embodiments, the location on a target lncRNA to which an inhibitory nucleic acids hybridizes is defined as a target region to which a protein binding partner binds. Routine methods can be used to design an inhibitory nucleic acid that binds to this sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. Target segments 5-500 nucleotides in length comprising a stretch of at least five (5) consecutive nucleotides within the protein binding region, or immediately adjacent thereto, are considered to be suitable for targeting as well. Target segments can include sequences that comprise at least the 5 consecutive nucleotides from the 5'-terminus of one of the protein binding regions (the remaining nucleotides being a consecutive stretch of the same RNA beginning immediately upstream of the 5'-terminus of the binding segment and continuing until the inhibitory nucleic acid contains about 5 to about 100 nucleotides). Similarly preferred target segments are represented by RNA sequences that comprise at least the 5 consecutive nucleotides from the 3'-terminus of one of the illustrative preferred target segments (the remaining nucleotides being a consecutive stretch of the same lncRNA beginning immediately downstream of the 3'-terminus of the target segment and continuing until the inhibitory nucleic acid contains about 5 to about 100 nucleotides).

One having skill in the art armed with the sequences provided herein will be able, without undue experimentation, to identify further preferred protein binding regions to target.

Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target RNAs), to give the desired effect.

In preferred embodiments, the target RNA is selected from the following table:

| Gene | | Human RefSeq - Nucleic acid |
|---|---|---|
| TNF-α | | NM_000594.3 |
| NF-kB | NFKB1/p105 | NM_003998.3 |
| | RELA/p65 | NM_021975.3 |
| | REL | NM_002908.3 |
| | NFKB2/p52 | NM_001077494.3 |
| | RELB | NM_006509.3 |
| COX-2 | | NM_000963.3 |
| HGF | | NM_000601.4 |
| c-Met | | NM_001127500.1 |

Making and Using Inhibitory Nucleic Acids

The inhibitory nucleic acids used to practice the methods described herein, whether RNA, cDNA, genomic DNA, vectors, viruses or hybrids thereof, can be isolated from a variety of sources, genetically engineered, amplified, and/or expressed, generated recombinantly or synthetically by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; Maier (2000) Org Lett 2(13): 1819-1822; Egeland (2005) Nucleic Acids Res 33 (14):e125; Krotz (2005) Pharm Dev Technol 10(2):283-90 U.S. Pat. No. 4,458,066. Recombinant nucleic acid sequences can be individually isolated or cloned and tested for a desired activity. Any recombinant expression system can be used, including e.g. in vitro bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion or "seamless cloning", ligation, transformation, plasmid purification, and DNA sequencing, for example as described in Sambrook et al. "Molecular Cloning: A Laboratory Manual." (1989)), Coffin et al. (Retroviruses. (1997)) and "RNA Viruses: A Practical Approach" (Alan J. Cann, Ed., Oxford University Press, (2000)). "Seamless cloning" allows joining of multiple fragments of nucleic acids in a single, isothermal reaction (Gibson (2009) Nat Methods 6:343-345; Werner (2012) Bioeng Bugs 3:38-43; Sanjana (2012) Nat Protoc 7:171-192). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus (Warnock (2011) Methods in Molecular Biology 737:1-25). The recombinant vectors capable of expressing the nucleic acids of the invention can be delivered as described herein, and persist in target cells (e.g., stable transformants).

This can be achieved, for example, by administering an inhibitory nucleic acid, e.g., an antisense oligonucleotide that is complementary to a target sequence. Other inhibitory nucleic acids for use in practicing the methods described herein and that are complementary to a target sequence can be those which inhibit post-transcriptional processing of the target RNA such as inhibitors of mRNA translation (antisense), agents of RNA interference (RNAi), catalytically active RNA molecules (ribozymes), and RNAs that bind proteins and other molecular ligands (aptamers). Additional methods exist to inhibit endogenous microRNA (miRNA) activity through the use of antisense-miRNA oligonucleotides (antagomirs) and RNA competitive inhibitors or decoys (miRNA sponges).

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to a target sequence. Thus, oligonucleotides are chosen that are sufficiently complementary to the target, i.e., that hybridize sufficiently well and with sufficient specificity, to give the desired effect, while striving to avoid significant off-target effects i.e. must not directly bind to, or directly significantly affect expression levels of, transcripts other than the intended target. The optimal length of the antisense oligonucleotide may very but it should be as short as possible while ensuring that its target sequence is unique in the transcriptome i.e. antisense oligonucleotides may be as short as 12-mers (Seth (2009) J Med Chem 52:10-13) to 18-22 nucleotides in length.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target.

It is understood in the art that a complementary nucleic acid sequence need not be 100% complementary to that of its target nucleic acid to be specifically hybridisable. A complementary nucleic acid sequence of the invention is specifically hybridisable when binding of the sequence to the target DNA or RNA molecule interferes with the normal function of the target DNA or RNA to cause a loss of activity, and there is a sufficient degree of complementarity to avoid non-specific binding of the sequence to non-target sequences under conditions in which specific binding is desired, i.e., under physiological conditions in the case of in vivo assays or therapeutic treatment, and in the case of in vitro assays, under conditions in which the assays are performed under suitable conditions of stringency. The antisense oligonucleotides useful in the methods described herein have at least 80% sequence complementarity to a target region within the target nucleic acid, e.g., 90%, 95%, or 100% sequence complementarity to a target region. Percent complementarity of an antisense compound with a region of a target nucleic acid can be determined routinely using basic local alignment search tools (BLAST programs) (Altschul (1990) J. Mol. Biol. 215, 403-410; Zhang and Madden (1997) Genome Res. 7, 649-656). The specificity of an antisense oligonucleotide can also be determined routinely using BLAST program against the entire genome of a given species For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art. For most applications, washing steps that follow hybridization will also vary in stringency. Wash stringency conditions can be defined by salt concentration and by temperature. As above, wash stringency can be increased by decreasing salt concentration or by increasing temperature.

For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York, Hilario (2007) Methods Mol Biol 353:27-38.

Inhibitory nucleic acids for use in the methods described herein can include one or more modifications, e.g., be stabilized against nucleolytic degradation such as by the incorporation of a modification, e.g., a nucleotide modification. For example, inhibitory nucleic acids can include a phosphorothioate at least the first, second, or third internucleotide linkage at the 5' or 3' end of the nucleotide sequence. As another example, inhibitory nucleic acids can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the inhibitory nucleic acids can include at least one 2'-O-methyl-modified nucleotide, and in some embodiments, all of the nucleotides include a 2'-O-methyl modification.

Modifications

Chemical modifications, particularly the use of locked nucleic acids (LNAs) (Okiba (1997) Tetrahedron Lett 39:5401-5404; Singh (1998) Chem Commun 4:455-456), 2'-O-methoxyethyl (2'-O-MOE) (Martin (1995) Helv Chim Acta 78:486-504; You (2006) Nucleic Acids Res 34 (8):e60; Owczarzy (2011) Biochem 50(43):9352-9367), constrained ethyl BNA (cET) (Murray (2012) Nucleic Acids Res 40: 6135-6143), and gapmer oligonucleotides, which contain 2-5 chemically modified nucleotides (LNA, 2'-O-MOE RNA or cET) at each terminus flanking a central 5-10 base "gap" of DNA (Monia (1993) J Biol Chem 268:14514-14522; Wahlestedt (2000) PNAS 97:5633-5638), improve antisense oligonucleotide binding affinity for the target RNA, which increases the steric block efficiency.

Techniques for the manipulation of inhibitory nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Modified Bases/Locked Nucleic Acids (LNAs)—Abbreviation Version

In some embodiments, the inhibitory nucleic acids are "locked," i.e., comprise nucleic acid analogues in which the ribose ring is "locked" by a methylene bridge connecting the 2'-O atom and the 4'-C atom (see, e.g., Kaupinnen (2005) Drug Disc. Today 2 (3):287-290; Koshkin (1998) J. Am. Chem. Soc. 120(50):13252-13253). For additional modifications see US 20100004320, US 20090298916, and US 20090143326.

Modified Bases/Locked Nucleic Acids (LNAs)—Extended Version

In some embodiments, the inhibitory nucleic acids used in the methods described herein comprise one or more modified bonds or bases. Modified bases include phosphorothioate, methylphosphonate, peptide nucleic acids, or locked nucleic acid (LNA) molecules. Preferably, the modified nucleotides are locked nucleic acid molecules, including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen (2004) Oligonucleotides 14, 130-146). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., lncRNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the lncRNA. The LNA molecules can be chemically synthesized using methods known in the art.

The LNA molecules can be designed using any method known in the art; a number of algorithms are known, and are commercially available (e.g., exiqon.com). You (2006) Nuc. Acids. Res. 34:e60; McTigue (2004) Biochemistry 43:5388-405; and Levin (2006) Nuc. Acids. Res. 34:e142. For example, "gene walk" methods, similar to those used to design antisense oligos, can be used to optimize the inhibitory activity of the LNA; for example, a series of oligonucleotides of 10-30 nucleotides spanning the length of a target lncRNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

In some embodiments, the LNA molecules can be designed to target a specific region of the lncRNA. For example, a specific functional region can be targeted, e.g., a region comprising a known RNA localization motif (i.e., a region complementary to the target nucleic acid on which the lncRNA acts), or a region comprising a known protein binding region, e.g., a Polycomb (e.g., Polycomb Repressive Complex 2 (PRC2), comprised of H3K27 methylase EZH2, SUZ12, and EED)) or LSD1/CoREST/REST complex binding region (Tsai (2010) Science 329(5992):689-93; and Zhao (2008) Science 322(5902):750-6; Sarma (2010) PNAS 107 (51): 22196-201). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul (1990) J. Mol. Biol. 215, 403-410; Zhang and Madden (1997) Genome Res. 7, 649-656), e.g., using the default parameters.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin (1998) Tetrahedron 54, 3607-3630; Obika (1998) Tetrahedron Lett. 39, 5401-5404; Jepsen (2004) Oligonucleotides 14:130-146; Kauppinen (2005) Drug Disc. Today 2(3):287-290; and Ponting (2009) Cell 136(4):629-641, and references cited therein.

See also U.S. Ser. No. 61/412,862, which is incorporated by reference herein in its entirety.

siRNA/shRNA

In some embodiments, the nucleic acid sequence that is complementary to a target RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference. RNA interference may cause translational repression and degradation of target mRNAs with imperfect complementarity or sequence-specific cleavage of perfectly complementary mRNAs.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. After the siRNA has cleaved its target, it is released from that RNA to search for another target and can repeatedly bind and cleave new targets (Brummelkamp (2002) Science 296:550-553; Lee (2002) Nature Biotechnol., 20, 500-505; Miyagishi and Taira (2002) Nature Biotechnol 20:497-500; Paddison (2002) Genes & Dev. 16:948-958; Paul (2002) Nature Biotechnol 20, 505-508; Sui (2002) Proc. Natl. Acad. Sd. USA 99(6), 5515-5520; Yu (2002) Proc Natl Acad Sci USA 99:6047-6052; Peer and Lieberman (2011) Gen Ther 18, 1127-1133).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target. shRNAs that are constitutively expressed form promoters can ensure long-term gene silencing. Most methods commonly used for delivery of siRNAs rely on commonly used techniques for introducing an exogenous nucleic acid into a cell including calcium phosphate or calcium chloride precipitation, microinjection, DEAE-dextrin-mediated transfection, lipofection, commercially available cationic polymers and lipids and cell-penetrating peptides, electroporation or stable nucleic acid-lipid particles (SNALPs), all of which are routine in the art. siRNAs can also be conjugated to small molecules to direct binding to cell-surface receptors, such as cholesterol (Wolfrum (2007) Nat Biotechnol 25:1149-1157), alpha-tocopherol (Nishina (2008) Mol Ther 16:734-40), lithocholic acid or lauric acid (Lorenz (2004) Bioorg Med Chem Lett 14:4975-4977), polyconjugates (Rozema (2007) PNAS 104:12982-12987).

A variation of conjugated siRNAs are aptamer-siRNA chimeras (McNamara (2006) Nat Biotechnol 24:1005-1015; Dassie (2009) Nat Biotechnol 27:839-849) and siRNA-fusion protein complexes, which is composed of a targeting peptide, such as an antibody fragment that recognizes a cell-surface receptor or ligand, linked to an RNA-binding peptide that can be complexed to siRNAs for targeted systemic siRNA delivery (Yao (2011) Sci Transl Med 4(130):130ra48.

Ribozymes

Trans-cleaving enzymatic nucleic acid molecules can also be used; they have shown promise as therapeutic agents for human disease (Usman & McSwiggen, (1995) Ann. Rep. Med. Chem. 30, 285-294; Christoffersen and Marr (1995) J. Med. Chem. 38, 2023-2037; Weng (2005) Mol Cancer Ther 4, 948-955; Armado (2004) Hum Gene Ther 15, 251-262; Macpherson (2005) J Gene Med 7, 552-564; Muhlbacher (2010) Curr Opin Pharamacol 10(5):551-6). Enzymatic nucleic acid molecules can be designed to cleave specific targets within the background of cellular RNA. Such a cleavage event renders the target RNA non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel (1979) Proc. R. Soc. London B 205, 435) have been used to evolve new nucleic acid catalysts with improved properties, new functions and capable of catalyzing a variety of reactions, such as cleavage and ligation of phosphodiester linkages and amide linkages, (Joyce (1989) Gene 82, 83-87; Beaudry (1992) Science 257, 635-641; Joyce (1992) Scientific American 267, 90-97; Breaker (1994) TIBTECH 12, 268; Bartel (1993) Science 261:1411-1418; Szostak (1993) TIBS 17, 89-93; Kumar (1995) FASEB J. 9, 1183; Breaker (1996) Curr. Op. Biotech. 1, 442; Scherer (2003) Nat Biotechnol 21, 1457-1465; Berens (2015) Curr. Op. Biotech. 31, 10-15). Ribozymes can also be engineered to be allosterically activated by effector molecules (riboswitches, Liang (2011) Mol Cell 43, 915-926; Wieland (2010) Chem Biol 17, 236-242; U.S. Pat. No. 8,440,810). The development of ribozymes that are optimal for catalytic activity would contribute significantly to any strategy that employs RNA-cleaving ribozymes for the purpose of regulating gene expression. The most common ribozyme therapeutics are derived from either hammerhead or hairpin/paperclip motifs. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min−1. In addition, it is known that certain modified hammerhead ribozymes that have substrate binding arms made of DNA catalyze RNA cleavage with multiple turn-over rates that approach 100 min−1. Ribozymes can be delivered to target cells in RNA form or can be transcribed from vectors. Due to poor stability of fully-RNA ribozymes, ribozymes often require chemical modification, such as, 5'-PS backbone linkage, 2'-O-Me, 2'-deoxy-2'-C-allyluridine, and terminal inverted 3'-3' deoxyabasic nucleotides (Kobayashi (2005) Cancer Chemother Pharmacol 56, 329-336).

Antagomirs

In some embodiments, the antisense is an antagomir. Antagomirs are chemically modified antisense oligonucleotides that target an lncRNA or miRNA (U.S. Pat. No. 8,937,217). For example, an antagomir for use in the methods described herein can include a nucleotide sequence sufficiently complementary to hybridize to a target sequence of about 12 to 25 nucleotides, preferably about 15 to 23 nucleotides.

In general, antagomirs include a cholesterol moiety, e.g., at the 3'-end. In some embodiments, antagomirs have various modifications for RNase protection and pharmacologic properties such as enhanced tissue and cellular uptake. For example, In addition to the modifications discussed above for antisense oligonucleotides, an antagomir can have one or more of complete or partial 2'-O-methylation of sugar and/or a phosphorothioate backbone. Phosphorothioate modifications provide protection against RNase activity and their lipophilicity contributes to enhanced tissue uptake. In some embodiments, the antagomir cam include six phosphorothioate backbone modifications; two phosphorothioates are located at the 5'-end and four at the 3'-end. See, e.g., Krutzfeldt (2005) Nature 438, 685-689; Czech (2006) N Engl J Med, 354:1194-1195; Robertson (2010) Silence. 1:10; Marquez and McCaffrey (2008) Hum Gene Ther., 19(1):27-38; van Rooij (2008) Circ Res. 103(9):919-928; and Liu (2008) Int. J. Mol. Sci. 9:978-999; (Ebert (2010) RNA 16, 2043-2050). Antagomirs useful in the present methods can also be modified with respect to their length or otherwise the number of nucleotides making up the antagomir. The antagomirs must retain specificity for their target, i.e., must not directly bind to, or directly significantly affect expression levels of, transcripts other than the intended target.

In some embodiments, the inhibitory nucleic acid is locked and includes a cholesterol moiety (e.g., a locked antagomir; Krutzfeldt (2005) Nature 438, 685-689).

In some embodiments, the antisense is a miRNA sponge or a variation of miRNA sponge, such as target mimics (Franco-Zorrilla (2007) Nat Genet 39:1033-1037), decoys (Care (2007) Nat Med 13:613-618, miRNA target sequences (Gentner (2009) Nat Methods 6:63-66), miRNA erasers (Sayed (2008) Mol Biol Cell 19:3272-3282), and lentivirus-mediated antagomirs (Scherr (2007) Nucleic Acid Res 35:e149). Sponge constructs typically contain 4-10 binding sites separated by a few nucleotides each. The efficacy of miRNA sponges depends on affinity and avidity of binding sites, as well as the concentration of sponge RNAs relative to the concentration of the miRNA.

Pharmaceutical Compositions

The methods described herein can include administration of an active agent as described herein in a pharmaceutical composition. Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

The present pharmaceutical compositions are formulated to be compatible with the intended route of administration.

In some embodiments, the compositions are delivered systemically, e.g., by parenteral, e.g., intravenous, intradermal, or subcutaneous administration.

In some embodiments, the compositions are administered by application of a liquid, foam, or gel formulation to the round window membrane. Application to the round window membrane can be accomplished using methods known in the art, e.g., intra-tympanic injection of a liquid, foam, or gel formulation or by direct delivery into the inner ear fluids, e.g., using a microfluidic device such as an implantable pump.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In some embodiments, the therapeutic compounds are prepared with carriers that will protect the therapeutic compounds against rapid elimination from the body, such as a controlled release formulation, including implants and microencapsulated delivery systems. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811. Nanoparticles, e.g., poly lactic/glycolic acid (PLGA) nanoparticles (see Tamura et al., Laryngoscope. 2005 November; 115(11):2000-5; Ge et al., Otolaryngol Head Neck Surg. 2007 October; 137(4):619-23; Horie et al., Laryngoscope. 2010 February; 120(2):377-83; Sakamoto et al., Acta Otolaryngol Suppl. 2010 November; (563):101-4) can also be used.

In some embodiments, the carrier comprises a polymer, e.g., a hydrogel, that increases retention of the compound on the round window and provides local and sustained release of the active ingredient. Such polymers and hydrogels are known in the art, see, e.g., Paulson et al., Laryngoscope. 2008 April; 118(4):706-11 (describing a chitosan-glycero-phosphate (CGP)-hydrogel based drug delivery system); other carriers can include thermo-reversible triblock copolymer poloxamer 407 (see, e.g., Wang et al., Audiol Neurootol. 2009; 14(6):393-401. Epub 2009 Nov. 16, and Wang et al., Laryngoscope. 2011 February; 121(2):385-91); poloxamer-based hydrogels such as the one used in OTO-104 (see, e.g., GB2459910; Wang et al., Audiol Neurotol 2009; 14:393-401; and Piu et al., Otol Neurotol. 2011 January; 32(1):171-9); Pluronic F-127 (see, e.g., Escobar-Chavez et al., J Pharm Pharm Sci. 2006; 9(3):339-5); Pluronic F68, F88, or F108; polyoxyethylene-polyoxypropylene triblock copolymer (e.g., a polymer composed of polyoxypropylene and polyoxyethylene, of general formula E106 P70 E106; see GB2459910, US20110319377 and US20100273864); MPEG-PCL diblock copolymers (Hyun et al., Biomacromolecules. 2007 April; 8(4):1093-100. Epub 2007 Feb. 28); hyaluronic acid hydrogels (Borden et al., Audiol Neurootol. 2011; 16(1):1-11); foams, e.g., as described in WO2009132050A9, WO2011049958A2, WO2015031393A1, or WO2010048095A2; gelfoam cubes (see, e.g., Havenith et al., Hearing Research, February 2011; 272 (1-2):168-177); and gelatin hydrogels (see, e.g., Inaoka et al., Acta Otolaryngol. 2009 April; 129(4):453-7); other biodegradable, biocompatible polymers can be used, such as ethylene vinyl acetate, polyanhydrides, polyglycolic acid, collagen, polyorthoesters, and polylactic acid. Tunable self-assembling hydrogels made from natural amino acids L and D can also be used, e.g., as described in Hauser et al e.g. Ac-LD6-COOH (L) e.g. Biotechnol Adv. 2012 May-June; 30(3):593-603. Such formulations can be prepared using standard techniques, or obtained commercially, e.g., from Alza Corporation and Nova Pharmaceuticals, Inc. In some embodiments, the composition (e.g., in foam or gel form) is applied to the tympanic membrane, e.g., as described in WO2009132050A9, WO2011049958A2, WO2015031393A1, or WO2010048095A2.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

The pharmaceutical compositions can be included in a container, pack, or dispenser together with instructions for administration.

Dosage

An "effective amount" is an amount sufficient to effect beneficial or desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. In some embodiments, e.g., in subjects exposed to prolonged or repeated exposures to noise, e.g., normal noises such as are associated with activities of daily life (such as lawnmowers, trucks, motorcycles, airplanes, music (e.g., from personal listening devices), sporting events, etc.), or loud noises, e.g., at concert venues, airports, and construction areas, that can cause inner ear damage and subsequent hearing loss; e.g., subjects who are subjected to high levels of environmental noise, e.g., in the home or workplace, can be treated with repeated, e.g., periodic, doses of the pharmaceutical compositions, e.g., to prevent (reduce the risk of) or delay progression or hearing loss.

Dosage, toxicity and therapeutic efficacy of the therapeutic compounds can be determined by standard pharmaceutical procedures, e.g., in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. For example, samples of the perilymph or endolymph can be obtained to evaluate pharmacokinetics and approximate an effective dosage, e.g., in animal models, e.g., after administration to the round window. The dosage of such compounds lies preferably within a range of concentrations that include the ED50 with little or no toxicity. The dosage may vary within this range depending upon the dosage form employed and the route of administration utilized. For any compound used in the method of the invention, the therapeutically effective dose can be estimated from cell culture assays, and/or a dose may be formulated in animal models; alternatively, for those compounds that have been previously used in humans, clinically desirable concentrations can be used as a starting point. Such information can be used to more accurately determine useful doses in humans.

EXAMPLES

The invention is further described in the following examples, which do not limit the scope of the invention described in the claims.

Example 1 describes an improved methodology to culture human VS and great auricular nerve-derived SC cultures, which provided a robust and representative model to study VS pathobiology. Example 2 establishes the aberrant activation of pro-inflammatory transcription factor nuclear factor kappa B (NF-κB) Inhibition of NF-κB using siRNAs, an experimental NF-κB inhibitor and a clinically relevant and well-tolerated NF-κB inhibitor led to decrease in proliferation and survival in VS cells. Example 3 investigates another inflammatory pathway that is also upregulated in VS, namely cyclooxygenase 2 (COX-2). COX-2 was aberrantly upregulated and activated in VS and COX-2-inhibiting salicylates, including aspirin, led to decreased VS proliferation. Example 4 validates upregulation of hepatocyte growth factor and VEGF-A signaling in VS and investigates novel cross talk between the two angiogenic pathways in VS and SCs.

Following our hypothesis that VS leads to SNHL at least partially due to secreted factors, we explored the role of VS secretions and of specific molecules within the VS secretions in causing cochlear damage. Example 5 establishes the negative correlation between the level of VS secreted fibroblast growth factor 2 (FGF2), a growth factor previously implicated to be oto- and neuroprotective in other pathologies, with the degree of SNHL in VS patients. Further, FGF2's otoprotective potential is demonstrated by pre-treating murine neonatal cochlear explant cultures with FGF2 to prevent gentamicin-induced cochlear degeneration. Example 6 shows that VS-secreted factors cause damage to cochlear cells as tumor secretions from different VS applied to cochlear explants led to varied levels of damage. The potential of specific molecules within the VS secretions to modulate SNHL was explored. Example 7 focused on the ototoxic potential of tumor necrosis factor alpha (TNFα), a molecule whose concentration in VS secretions positively correlated with the degree of SNHL in VS patients. TNFα application led to damage in cochlear explants and TNFα neutralization led to partial rescue of cochlear damage due to VS secretions. Example 8 explored the potential role of VEGF-A in SNHL and could not identify its independent role or its role within VS secretions, although trends were noted.

Overall, several pathways in VS pathobiology that contribute to either VS growth or VS associated SNHL were identified or validated. Manipulation of these pathways through experimental and clinically relevant inhibitors identified promising biological targets to minimize tumor burden in VS patients.

Example 1

Primary Culture as a Representative Model to Study Vestibular Schwannoma Pathobiology Primary cultures of human Schwann cells (SCs) and VS cells are invaluable tools to investigate SC physiology and VS pathobiology, and to devise effective pharmacotherapies against VS. However, existing culture protocols, in aiming to create robust and pure cultures, employ methods that can lead to loss of biological characteristics of the original cells, potentially resulting in misleading biological findings. We have developed a minimally manipulative method to culture primary human SC and VS cells, without the use of selective mitogens, toxins, or time-consuming and potentially transformative laboratory techniques. SC purity was quantified longitudinally using S100 staining in SC cultures derived from great auricular nerves (GANs) and VS cultures followed for 7 and 12 weeks, respectively. SC cultures retained ≥85% purity for 2 weeks. VS cultures retained ≥80% purity for the majority of the span of 12 weeks, with maximal purity of 87% at 2 weeks. The VS cultures showed substantial biological similarity (68% on average) to their respective parent tumors, as assessed using a protein array featuring 41 growth factors and receptors. Apoptosis rate in vitro correlated negatively with tumor volume. Our results, obtained using a faster and simplified culturing method than previously utilized, indicate that highly pure, primary human SC and VS cultures can be established with minimal manipulation, reaching maximal purity at 2 weeks of culture. The VS cultures recapitulate the parent tumors' biology to a great degree, making them relevant models to investigate VS pathobiology.

Methods

Specimen Collection

GANs were used as the source for healthy human SCs as they are routinely sacrificed for access during parotidectomies and neck dissections Immediately after GAN resection, nerve specimens measuring 1 cm (from parotidectomies) to 5 cm (from neck dissections) were placed in sterile saline on ice and transported to the laboratory. Similarly, human VS tumor specimens were collected immediately after resection and were transported to the laboratory in sterile saline on ice. The total time from resection to processing was approximately 20 minutes for GANs and VSs. Specimens were handled according to the institutional review board's study protocol approved by the Human Studies Committee of Massachusetts General Hospital and Massachusetts Eye and Ear Infirmary.

Schwann and Schwannoma Cell Isolation and Culture

GAN samples were washed with sterile PBS thrice to remove accompanying blood or scar tissue, and transferred to supplemented DMEM/F12 medium, consisting of 39% Dulbecco's Modified Eagle's Medium (DMEM; Life Technologies, NY), 39% F12 Nutrient Mixture (ThermoScientific, MA), 10% Fetal Bovine Serum (Life Technologies, NY), 1% Penicillin/Streptomycin mix (ThermoScientific, MA, 15140-122) and 1% L-Glutamate (Life Technologies, NY). Under a dissecting microscope, the fascicles were isolated from the epineurium by tugging on the perineurium using no. 5 forceps (Fine Science Tools, CA, #11251-20), while clasping the epineurium with no. 3 forceps (Fine Science Tools, CA). A scalpel blade (#10) was used to cut the nerve into 1-2 mm segments, which were then incubated in an enzymatic mixture containing 250 U/mL Hyaluronidase Type I-S (Sigma-Aldrich, MO) and 160 U/mL Collagenase Type I (Sigma-Aldrich, MO) in DMEM/F12 medium. No further growth factors were added. GAN pieces were incubated for 24 hours at 37° C. with 5% $CO_2$ levels. In the meantime, in a sterile environment, 12-well dishes (USA Scientific, Inc., FL) were coated with poly-L-ornithine (Sigma-Aldrich, MO) overnight at room temperature (RT), rinsed with sterile PBS thrice and coated with laminin (BD Biosciences, MA) diluted in DMEM/F12 medium for at least 1 hour at room temperature (RT). After the enzymatic incubation of the culture, the cell culture-containing medium was triturated using an 18-gauge needle (BD Biosciences, MA). The cells were recovered by centrifugation at 1000 g for 5 minutes at RT. The pellet was resuspended in supplemented DMEM/F12 medium and plated on poly-L-Lysine and laminin pre-coated coverslips (BD Biosciences, MA) within the 12-well dishes coated with poly-L-ornithine and laminin. Culture medium was replaced with fresh medium after 24 hours, then every 3 days.

The same protocol was followed for VS cell cultures with two notable changes. Firstly, during initial tissue dissection, cauterized portions (white and opaque) and blood vessels were carefully separated and removed from the main specimen (yellow and clear, fascia-like). The cleaned specimen was minced into approximately 1 $mm^3$ pieces by using two no. 5 forceps. Secondly, the tumor cells were incubated in media with enzyme mixture for 18 hours (versus 24 hours for GAN). This length of time was found to be ideal for separating cells while also retaining some tumor cell clusters to augment the growth of the culture.

Culture Characterization

Longitudinal culture growth was assessed qualitatively through light microscopy. Differential interference contrast microscopy images were obtained weekly in select GAN-derived and VS-derived cultures for up to 10 and 12 weeks, respectively.

Immunofluorescence

Longitudinal SC purity was quantified using immunofluorescence. Cultured cells were washed in PBS, fixed with 4% paraformaldehyde (Electron Microscopy Sciences, PA) in PBS for 20 minutes, washed with PBS, treated with 0.4% Triton X (Integra Chemical, WA) for 5 minutes, exposed to a blocking buffer consisting of 5% Normal Horse Serum (NHS, Sigma-Aldrich, MO), and incubated in primary anti-S100 antibody (Dako, CA, 1:400) diluted in 1% NHS overnight at 4° C. to mark SCs. According to the manufacturer, this antibody strongly labels S100B, an isoform expressed by glial cells and highly enriched in SCs (Spreca et al., 1989), and very weakly labels S100A6, an isoform found in fibroblasts and epithelial cells. At the dilution used, we did not find S100 labeling in morphologically fibroblast-like cells. The cells were washed and an anti-rabbit IgG (Jackson Immuno Research, PA, 1:200) diluted in 1% NHS was applied for 2 hours at RT. Nuclear staining was performed with two 5-minutes washes in Hoechst stain 33342 (Life Technologies, NY, 1 nM dilution) followed by two 5-minutes PBS washes. The coverslips were mounted on glass slides using Vectashield (Vector Laboratories, CA, #H-1000). The edges of the coverslips were sealed using clear nail polish (Electron Microscopy Sciences, PA). Cells were observed under the Axioskop 2 mot plus differential interference contrast microscope (Carl Zeiss, Germany) and photographed with the Axiocamera (Carl Zeiss, Germany) attached to the microscope. The fraction of Schwann and schwannoma cells present in the culture was quantified using manual counting. Cells were counted in ≥3 random fields per culture per time point. SC purity was reported as the ratio of S100 positive cells (cytoplasmic stain) to Hoechst positive cells (nuclear stain). The quantification was done for ≥3 different cultures for each time point. The data for each time point were not necessarily obtained from the same culture, although the majority of the measurements were done by following a given culture longitudinally. Slides were stored in the dark at −20° C. to minimize photobleaching.

Growth Factor Protein Arrays

Part of the fresh tumor specimens, after being washed in fresh sterile phosphate-buffered saline (PBS) thrice, were placed into cold RIPA buffer fortified with protease and phosphatase inhibitors for protein extraction. Protein was also extracted from VS cultures, aged approximately 2 weeks. Human growth factor array membranes printed with 41 specific antibodies in replicate (Human Growth Factor Array C1, RayBiotech, Inc., GA) were probed with tissue lysate from 3 parent VSs and corresponding cell culture lysates. The manufacturer's protocol was followed for experimental procedures. Briefly, samples were dialyzed and protein concentrations, measured spectrophotometrically, were normalized and then conjugated with biotin. The membranes were exposed to the blocking buffer, incubated with biotin-conjugated sample at 4° C. overnight, washed and incubated with HRP-conjugated streptavidin at 4° C. overnight. The membranes were incubated in detection buffer for 1 minute, and exposed in Chemidoc (BioRad Laboratories, Hercules, Calif.). Optical density for the growth factor arrays was measured using Quantity One (BioRad Laboratories, Hercules, Calif.) and was analyzed and normalized for all samples using the RayBiotech Growth Factor Array analysis tool (RayBiotech, Inc., GA).

Proliferation Assay

Proliferation rate of 12 VS cultures was assessed and correlated with the tumor volume in the latest gadolinium enhanced T1-weighted MRI scan prior to surgical resection, and with tumor growth in vivo, measured as changes in the tumor's volume over time calculated from serial MRI scans. Tumor growth was standardized by dividing the growth rate by the initial tumor volume. Separate analyses were performed for solid tumors, which generally account for approximately 96% of VSs (Charabi et al., 1994), versus all studied tumors, which included 4 out of 13 total tumors with a visible cystic component, because cystic components could misrepresent true tumor volume (Charabi et al., 1994). To determine the level of cell proliferation in the cultures, Bromodeoxyuridine (BrdU) was added to the cells at a concentration of 10 μg/ml 20 hours before the cells were fixed. The cells were kept in the dark after the addition of BrdU Immunofluorescence protocol was followed as described under 'Immunofluorescence,' and cell and nuclear membranes were permeablized by incubation in 1% Triton-X for 10 minutes and by incubation in 2N Hydrochloric acid for 20 minutes, respectively, after fixation. Primary antibody against BrdU (AbD Serotec, NC, 1:200) and anti-rat IgG (Life Technologies, NY, 1:1000) were used. BrdU- and Hoechst-stained nuclei were counted in 3-5 fields and the ratio of BrdU positive to Hoechst positive nuclei was used to determine the proliferation rate in vitro.

Apoptosis Assay

Rate of apoptosis in 6 VS cultures was assessed and correlated with tumor growth in vivo and tumor volume. Two out of the six VS had cystic components. Apoptosis was measured using terminal deoxynucleotidyl transferase dUTP nick end labeling (TUNEL, Roche Applied Sciences, NY) following manufacturer's instructions. Briefly, immunofluorescence protocol was followed as described under 'Immunofluorescence,' until fixations, then the cells were washed with PBS thrice and incubated in 1% Triton-X for 10 minutes on shaker. The cells were washed with PBS once and incubated in TUNEL mix for 1 hour at 37° C., then for 30 minutes at RT on shaker. The cells were then incubated in rhodamine phalloidin (Life Technologies, NY, 1:40) and Hoechst stain for 20 minutes, washed with PBS thrice and mounted onto slides for imaging. TUNEL and Hoechst stained nuclei were counted in >3 fields and the ratio of TUNEL positive to Hoechst positive nuclei was used to determine apoptosis rate in vitro. A positive control of 10 minutes-DNAse (Roche Applied Sciences, NY) treatment prior to TUNEL labeling was utilized.

Statistical Analyses

Microsoft Excel 2010 was utilized for statistical analyses pertaining to Schwann cell purity, proliferation and apoptosis assays. Schwann cell purity was compared between different time points using a two-tailed t-test followed by Benjamini-Hochberg adjustment to obtain p-values. Nonparametric spearman's rank correlations were utilized when correlating VS culture proliferation and apoptosis rates to tumor growth rate in vivo and tumor volume as recommended for small sample sizes (n<15). Standard errors of mean (SEM) are provided for S100, proliferation and apoptosis cell counts, where mean of each culture (counted in ≥3 different fields) was compared across cultures from different specimens. Standard deviations (SD) are provided for all other measures. To analyze growth factor array expression, R software was utilized for hierarchical clustering (with Manhattan distance measurement and complete linkage). Additionally, repeated measures ANOVA and Excel were utilized for paired t-tests followed by Benjamini-Hochberg adjustment to obtain p-values. For all statistical analyses, a p-value (p)<0.05 was considered significant.

Results

Morphological Characteristics of Human Nerve-derived Primary Schwann Cell Culture Fifteen GAN specimens, each from a different patient, were acquired, yielding healthy SCs for culture. Cells isolated after enzymatic digestion were cultured in media and adhered onto coverslips in less than 24 hours. Dissections with the most clear and successful isolation of the fascicles gave rise to the purest SC cultures. The cultured cells demonstrated distinct morphologies whose distribution changed significantly overtime. The morphologies seen were SC-like with a small cell body and bipolar processes versus fibroblast-like with flat and polygonal cell body accompanied by a larger nucleus than that of SC-like cells. SC-like morphology predominated in the culture until week 2 at a confluence of approximately 40%, at which point fibroblast-like cells began to predominate. Although the confluence increased significantly after week 2 progressively reaching 99%, most of this increase could be attributed to fibroblast-like cell infiltration and proliferation. This interceding phase of fibroblast-predominance reverted around week 7, at which time proliferation subsided and fibroblast-like cells appeared to be dying faster than SCs.

The culture retained a high SC-like cell distribution in weeks 8 through 10, similar to the cellular distribution seen before 2 weeks of growth. Culture growth was not assessed after 10 weeks in vitro as very few cells remained.

Morphological Characteristics of Human Schwannoma-derived Primary Cell Culture

Twenty-four VS specimens, each from a different patient, were acquired and used for VS cell culture. Specimens that were minimally cauterized before resection and were processed for culture immediately after resection seemed to yield the purest and most robust cultures. Cellular morphology seen was similar to nerve-derived cultures, although the cells were larger. Longitudinally, the cells could be characterized by sustained growth, lacking contact-mediated inhibition and cell loss noted in week 7 of nerve-derived cultures. These characteristics are consistent with neoplastic growth. For VS cultures, it was important to retain few cell clusters for many of the cultures, or else the cultures were not as robust. The cell density was noted to be increasing until week 2, after which the total number of cells decreased as the cultures aged (Table 1), suggesting that culture proliferation peaks at approximately week 2.

Purity of Primary VS and SC Cultures

SC purity was assessed by immunostaining for cytoplasmic S100, a well-established marker for SCs (Spreca et al., 1989). Actual values for fraction of S100 positive cells from the nerve-derived and schwannoma-derived cultures are provided in Table 1. In the SC cultures followed in vitro over time, we demonstrate a high level of SC purity, averaging 85% for up to 2 weeks; after that fibroblast-like cells predominate (Table 1). For weeks 1 through 7, our qualitative observations were in concert with the quantitative measurements based on the fraction of S100 positive cells (Table 1). Although most SC cultures demonstrated ≥70% purity throughout the duration of the experiments, two out of nine cultures retained approximately 10% SCs over time.

VS cells retained 80% purity on average for the majority of 12 weeks in vitro (Table 1). There was a decrease in S100 positivity at week 3, which could be partly attributed to the fact that different cultures were used to quantify percentage of S100-positive cells at 3 weeks than at other time points (Table 1). Similar to the nerve-derived cultures, two out of seventeen VS cultures retained many more fibroblast-like cells than SCs. S100-based SC or VS purity did not differ significantly between subsequent weeks of growth (p>0.05 for all comparisons).

TABLE 1

Longitudinal growth of Schwann cell and VS cultures. For each type of culture, first column describes the age at which the cultures were assessed. Second column details the total cells counted per field on average per time point.Third column details the average fraction of immunofluorescently marked S100 positive cells over total Hoechst stain marked nuclei as seen in ≥3 different fields with the number of cultures derived from different surgical specimens shown with n in parentheses. Fourth column details the standard error of mean (SEM) calculated within the cultures at a given time point.

| Schwann cell cultures | | | | VS cultures | | | |
|---|---|---|---|---|---|---|---|
| Culture age (weeks) | Total cells per field | Percentage S100-positive cells Average (n) | SEM | Culture age (weeks) | Total cells per field | Percentage S100-positive cells Average (n) | SEM |
| 1 | 86 | 85 (4) | 7 | 2 | 258 | 88 (5) | 5 |
| 2 | 189 | 85 (3) | 2 | 3 | 211 | 72 (6) | 14 |
| 4 | 172 | 42 (3) | 22 | 4 | 210 | 78 (5) | 5 |
| 7 | 136 | 61 (3) | 13 | 5 | 177 | 78 (3) | 4 |
| | | | | 7-12 | 148 | 86 (4) | 4 |

Correlation of Parent VS Biology to Derived Cultures

Biological similarity was compared between three VSs, namely VS1, 2 and 3, and their derived primary cultures. Out of the 41 growth factors and receptors analyzed, VS1, 2 and 3 had 31, 25 and 7 proteins expressed, respectively (Table 2). VS1 culture's, having 25 proteins expressed, protein expression was most similar to its parent tumor, with 83% proteins overlapping (Table 2). Cultures from VS2, having 19 proteins expressed, and VS3, having 4 proteins expressed, had 76% and 43% proteins overlapping with their respective parent tumors (Table 2). On average, 68% proteins present in a tumor were also present in the corresponding derived culture, with only a few new proteins being detected in the culture that were not present in the tumors, on average 13.4% (Table 2). Three proteins, namely macrophage colony stimulating factor (M-CSF), vascular endothelial growth factor D (VEGF-D) and fibroblast growth factor 2 (FGF2), were present in all VS and VS cultures. Hierarchical clustering demonstrated that a given VS and its derived culture were most closely related. Although we did find that the relative level of different proteins differed between the original tumor and cultures, the most highly expressed proteins in the tumors were also highly expressed by the cultures (Table 2). Conducting a repeated measures ANOVA, significant expression difference among the entire set of tumors and derived cultures was found for the 41 proteins ($p<0.001$). Paired t-tests indicated that the parent tumors were not significantly different from their cultures, with p-values for VS1, VS2 and VS3 being 0.99, 0.99 and 0.41, respectively. The rest of the comparisons, e.g. VS1 with VS2 or VS1 with VS2 culture, were significant ($p<0.01$), except for VS3 with VS1 ($p=0.55$) and VS1 culture ($p=0.55$). This trend of similarity between VS1 and VS3 is also reflected in the dendrogram with VS1 and VS3 samples branching closest together.

Although most proteins found in the VS were present in the cultures, three proteins, being the insulin growth factor 2 (IGF-II), insulin-like growth factor 1 receptor (IGF-IsR) and neurotrophin-3 (NT-3), were not found in the cultures although being present in at least two out of three VSs analyzed (Table 2). Members of the fibroblast growth factor family, fibroblast growth factor 6 (FGF6) and 7 (FGF7), although not being present in the parent tumors, were expressed in the derived cultures VS2C and VS3C, respectively (Table 2). Probing with RIPA only did not produce positive staining except at the positive control spots coated with the biotinylated immunoglobulins (IgGs).

TABLE 2

Protein symbols, names and expression values of 41 proteins analyzed in VS and their derived cultures. Values (optical density units) for three VS, namely VS1, VS2, VS3, and their derived cultures VS1C, VS2C and VS3C, respectively, are shown. All optical densities were normalized to VS1. Zeros represent no protein detected, i.e. when signal detected was below the negative control on the array. (Continued)

| | | Relative Expression in Tumor and Respective Culture | | | | | |
|---|---|---|---|---|---|---|---|
| Symbol | Protein Name | VS1 | VS1C | VS2 | VS2C | VS3 | VS3C |
| AR | Amphiregulin | 3.43 | 21.87 | 36.11 | 13.13 | 0 | 0 |
| bNGF | Nerve growth factor B | 12.5 | 21.09 | 32.53 | 34.55 | 0 | 0 |
| EGF | Epidermal growth factor | 0 | 0 | 0 | 0 | 0 | 0 |
| EGFR | Epidermal growth factor receptor | 14.52 | 21.07 | 33.54 | 36.91 | 32.45 | 0 |
| FGF-2 | Fibroblast growth factor 2 | 6.65 | 23.03 | 36.14 | 17.26 | 12.34 | 8.03 |
| FGF-4 | Fibroblast growth factor 4 | 0 | 0 | 0 | 31.34 | 0 | 0 |
| FGF-6 | Fibroblast growth factor 6 | 0 | 0 | 0 | 31.83 | 0 | 0 |
| FGF-7 | Fibroblast growth factor 7 | 15.04 | 25.68 | 44.85 | 32.17 | 0 | 25.68 |
| G-CSF | Granulocyte colony-stimulating factor | 14.84 | 21.02 | 55.44 | 37.72 | 0 | 0 |
| GDNF | Glial cell line-derived neurotrophic factor | 0 | 0 | 47.1 | 40.48 | 0 | 0 |
| GM-CSF | Granulocyte macrophage colony-stimulating factor | 14.55 | 21.46 | 40.48 | 0 | 0 | 0 |
| HB-EGF | Heparin-binding EGF like growth factor | 48.52 | 20.71 | 38.86 | 138.8 | 40.5 | 0 |
| HGF | Hepatocyte growth factor | 0 | 0 | 0 | 0 | 0 | 0 |
| IGFBP-1 | Insulin-like growth factor-binding protein 1 | 0 | 0 | 34.92 | 44.91 | 0 | 0 |
| IGFBP-2 | Insulin-like growth factor-binding protein 2 | 12.59 | 25.43 | 33.56 | 45.27 | 0 | 0 |

TABLE 2-continued

Protein symbols, names and expression values of 41 proteins
analyzed in VS and their derived cultures. Values (optical density units) for three VS,
namely VS1, VS2, VS3, and their derived cultures VS1C, VS2C and VS3C,
respectively, are shown. All optical densities were normalized to VS1. Zeros represent
no protein detected, i.e. when signal detected was below the negative control on the
array. (Continued)

| | | Relative Expression in Tumor and Respective Culture | | | | | |
|---|---|---|---|---|---|---|---|
| Symbol | Protein Name | VS1 | VS1C | VS2 | VS2C | VS3 | VS3C |
| IGFBP-3 | Insulin-like growth factor-binding protein 3 | 16.79 | 20.2 | 34.52 | 63.86 | 0 | 0 |
| IGFBP-4 | Insulin-like growth factor-binding protein 4 | 0 | 20.11 | 33.68 | 0 | 0 | 0 |
| IGFBP-6 | Insulin-like growth factor-binding protein 6 | 16.11 | 21.74 | 36.9 | 44.27 | 0 | 0 |
| IGF-I | Insulin-like growth factor I | 13.45 | 21.94 | 40.64 | 42.16 | 0 | 0 |
| IGF-I sR | Insulin-like growth factor 1 receptor | 13.29 | 0 | 43.31 | 0 | 0 | 0 |
| IGF-II | Insulin-like growth factor II | 34.88 | 0 | 54.67 | 0 | 35.3 | 0 |
| M-CSF | macrophage colony-stimulating factor | 57.85 | 64.61 | 116.5 | 203.2 | 149.1 | 89.18 |
| NT-3 | Neurotrophin-3 | 19.07 | 0 | 37.98 | 0 | 0 | 0 |
| NT-4 | Neurotrophin-4 | 12.62 | 19.78 | 39.45 | 45.3 | 0 | 0 |
| PDGF-AA | Platelet Derived Growth Factor-AA | 0 | 0 | 51.64 | 69.88 | 0 | 0 |
| PDGF-AB | Platelet Derived Growth Factor-AB | 0 | 0 | 37.12 | 39.73 | 0 | 0 |
| PDGF-BB | Platelet Derived Growth Factor-BB | 0 | 0 | 0 | 0 | 0 | 0 |
| PDGF-R-a | Platelet-derived growth factor receptor alpha | 0 | 0 | 0 | 0 | 0 | 0 |
| PDGF-R-b | Platelet-derived growth factor receptor beta | 12.78 | 20.53 | 38.22 | 41.89 | 0 | 0 |
| PlGF | Placental Growth Factor | 0 | 0 | 42.96 | 42.03 | 0 | 0 |
| SCF | Mast cell growth factor | 0 | 0 | 0 | 0 | 0 | 0 |
| SCFR | Mast/stem cell growth factor receptor Kit | 14.09 | 19.26 | 57.41 | 46.11 | 0 | 0 |
| TGF-a | Transforming growth factor alpha | 0 | 0 | 0 | 0 | 0 | 0 |
| TGF-b-1 | Transforming growth factor beta-1 | 12.4 | 0 | 41.62 | 0 | 0 | 0 |
| TGF-b-2 | Transforming growth factor beta-2 | 14.79 | 0 | 39.43 | 38.99 | 0 | 0 |
| TGF-b-3 | Transforming growth factor beta-3 | 0 | 0 | 38.6 | 33.45 | 0 | 0 |
| VEGF-A | Vascular endothelial growth factor A | 32.14 | 19.66 | 38.99 | 36.32 | 33.09 | 0 |
| VEGF-D | Vascular endothelial growth factor D | 35.82 | 25.54 | 41.47 | 50.6 | 40.99 | 25.36 |
| VEGFR-2 | Vascular endothelial growth factor receptor 2 | 0 | 0 | 0 | 0 | 0 | 0 |
| VEGFR-3 | Vascular endothelial growth factor receptor 3 | 15.45 | 22.19 | 41.1 | 34.06 | 0 | 0 |
| PDGF-BB | Platelet Derived Growth Factor-BB | 0 | 0 | 0 | 0 | 0 | 0 |

Correlation of Tumor Characteristics In Vivo to Culture Characteristics

To determine whether the growth patterns noted in vivo were recapitulated in the cultures, we studied how VS volume and growth in vivo, as assessed by MRI, correlated with VS cell proliferation and apoptosis in vitro. Thirteen VS patients had tumor growth rates available because their tumors were followed by serial imaging prior to resection; 12 of these tumors were used for assessing proliferation rate in vitro and 6 for apoptosis rate in vitro in the derived cultures. MRI sections of the 13 VS demonstrate that 4 tumors had an apparent cystic component (tumors labeled (j)-(m)). Spearman's coefficient of rank correlation is indicated by R, with number of specimens being n. The range of VS proliferation in vitro was 0% to 13.51% for all VS analyzed. When including all tumors, VS proliferation in vitro, expressed as mean+SEM, was 6.58+1.29% and did not correlate with tumor volume, expressed as mean+SD, being 2.61+2.39 $cm^3$ (R=0.27, n=12, p=0.39) or the normalized tumor growth rate in vivo, being 0.05+0.07 $cm^3$/month (R=−0.11, p=0.73). When including only solid tumors (n=9), VS proliferation in vitro was 6.77+1.48% and still did not correlate with tumor volume, being 1.87+1.41 $cm^3$ (R=0.33, p>0.10) or the normalized tumor growth rate in vivo, being 0.04+0.08 $cm^3$/month (R=−0.10, p>0.10). Analyzing a subset of the tumors (n=4), 64.0%±4.7% (SEM) of the BrdU-positive cells were also S100-positive, suggesting that majority of the proliferation is arising from the schwannoma cells in the culture. Tumor growth and tumor volume in vivo did not correlate when including all VS (n=12 different VS, R=−0.08, p=0.81) or when including only solid VS (n=9 different VS, R=−0.37, p>0.10) in the analysis.

Apoptosis was measured in VS cultured cells using TUNEL and found to be occurring at low rates (1.55+0.72% SEM) in VS cultures (n=6 different VS). Apoptosis rates in vitro negatively correlated with tumor volume (R=−0.91, $0.025<p<0.05$) and did not correlate with tumor growth in vivo (R=0.16, p>0.10) when analyzing all VS. When including only solid VS (n=4), the negative correlation between apoptosis rate in vitro and tumor volume was no longer present (R=−0.8 p=0.20).

Discussion

Primary cultures of VS cells and non-neoplastic SCs are important tools to investigate VS pathobiology and its divergences from healthy SCs. To overcome some of the manipulations currently utilized in VS and SC cultures, which could transform cells and alter their true biology, we established a reproducible and technically easier method to culture primary human SCs and VS cells. We avoided currently popular practices of using cell specific-mitogens or toxins, and circumvented time-consuming, resource-intensive protocols. Additionally, we did not passage the cultured cells, a procedure known to alter the cells' biology (Neumann et al., 2010). Our modified protocol employs techniques such as laminin-coated coverslips and mild collagenase treatment, as suggested by previous successful work in isolating SCs (Pannunzio et al., 2005). This work is the first to longitudinally and quantitatively characterize primary human nerve-derived culture (over 7 weeks) and schwannoma-derived culture (over 12 weeks). This provides estimates for the most effective time windows to use healthy and neoplastic Schwann cells to investigate biological pathways in vitro. Additionally, we investigated biological similarity between the parent VSs' and derived cultures' pathobiology, validating our culture system to be representative of the tumor in vivo.

The SC purity that we achieved (85%) from surgically sacrificed human GANs is superior to previously described minimally manipulative SC culture methods, which demonstrated SC purities ranging from 35-64% (Morrissey, Kleitman & Bunge, 1991; Niapour et al., 2010). In line with other studies demonstrating fibroblast infiltration in Schwann and VS cultures (Calderon-Martinez, Garavito, Spinel & Hurtado, 2002; Niapour et al., 2010), we note fibroblast-like cells infiltrating the cultures over time, although at lower levels than previously reported. Our success may partly result from careful dissection of the nerve to remove the epineurium. In fact, in the two outlier SC cultures with very low purity, we believe that impurities may have been introduced at the time of nerve dissection due to incomplete removal of fibrous sheath or contamination of cell culture with discarded pieces. We realized over the duration of the study that precision in removing the epineurium cleanly and carefully to avoid damage to the fascicles was an important factor for a high SC purity longitudinally. While we were unable to overcome eventual fibroblast-like cell contamination, as has been possible with potentially highly manipulative and transformative methodologies, e.g. 95% purity gradually achieved over 20 days with antimitotic cytosine arabinoside (Ara-C) treatment (Calderon-Martinez, Garavito, Spinel & Hurtado, 2002), we did establish a relatively pure population (85% purity) of minimally transformed SCs for up to 2 weeks. Our data demonstrating a drop in SCs after 2 weeks, followed by resurgence of SCs at 7 weeks, are consistent with fibroblast proliferation and eventual death in culture, with more stable SCs over time.

Our protocol was also effective in establishing a robust VS cell culture (80% pure) for the majority of 12 weeks, in contrast to others who noted significant fibroblast contamination when using a minimally manipulative protocol (Nair, Leung, Collins, Ramsden, & Wilson, 2007). Our purity was highest at 2 weeks (87% pure), suggesting that this time point is optimal for use of the culture to investigate schwannoma pathobiology.

Although an immortalized schwannoma cell line is available, i.e. HEI-193, a major advantage of primary cell cultures over cell lines is that the primary cultures are not transformed, and that they can capture the inherent biological diversity between different patients and tumors, which facilitates development of therapies that are generally effective. We attempted to explore the similarity between the parent tumors' biology and their derived cultures using a protein array, a novel comparison to the best of our knowledge. This microarray, consisting of 41 proteins, included several receptor tyrosine kinases (e.g. epidermal growth factor receptor (EGFR), Ahmed et al., 2011) and growth factors (e.g. fibroblast growth factor 2 (FGF2), Koutsimpelas et al., 2007; Dilwali et al., 2013) that have already been implicated in VS pathobiology. Such correlations are important to critically evaluate how representative a culture system is of the VS pathobiology in vivo. We found, on average, 68% biological similarity between the parent tumor and the derived culture, as assessed with protein arrays. Our studies are comparable to those of other cells, namely hepatocytes, which showed 77% similarity in gene expression between parent tissue and primary cultures (Olsaysky et al., 2007) using mRNA microarrays. Our analysis demonstrates that the significant intertumor heterogeneity present in VS is maintained in our culture system since the parent VSs and their derived cultures segregated into pairs in an unbiased hierarchical clustering analysis. Although most of the biology in parent tumors was noted in the derived cultures, the diminished expression of specific proteins, such as some components of the insulin growth factor pathway or neutrotrophin-3, and new expression of proteins in culture reinforces that one should validate the aberrant expression of a given biological protein in primary tissue and its derived culture before studying its role in culture. Interestingly, some components of the IGF pathway, i.e. IGF-I, IGFBP-1 and IGFBP-3, were still detected in the culture if present in the parent VS, suggesting the diminished expression to be protein-specific rather than pathway-specific. Similarly, there was new expression of some members of the fibroblast growth family. These changes are expected as we alter the microenvironment of these cells from in vivo to a much simpler in vitro system. Nonetheless, it is reassuring that our VS culture system still provides a representative model to a great extent.

Along with protein expression, we attempted to correlate VS cultures' growth patterns with the clinical features of the parent tumors in vivo. We observed a large range of VS proliferation in vitro among different cultures, consistent with the heterogeneous VS growth rates in vivo and in vitro (Utermark, Kaempchen, Antoniadis & Hanemann, 2005). The low rates of apoptosis that we observed in VS cultures are consistent with the neoplastic nature of these cells. Although our rate, averaging 1.55%, is lower than a study conducted by Utermark et al. describing apoptosis rate in primary VS cultures (8.5% using TUNEL), it was closer to their findings in paraffin-embedded tumor specimens (0.65%) (Utermark, Kaempchen, Antoniadis & Hanemann, 2005) and similar to other studies noting 1.16% apoptosis rate in primary VS cultures (Cioffi et al., 2010). Interestingly, we did find that the apoptosis rate was negatively correlated with tumor volume ($0.025<p<0.05$), suggesting that smaller tumors exhibit higher rates of cell death. Future work is needed to affirm this correlation. Removing the VSs with a cystic component, the correlation's significance was lost. Since the spread of the data points did not change considerably, it is probable that this change in significance was due to a decrease in sample size from n=6 to n=4, rather that due to exclusion of cystic tumors. We did not find proliferation rates of cultured VS cells to correlate with tumor growth rate or volume in vivo—this held even if only solid tumors were analyzed, if tumor growth was not standardized to initial volume or if growth rate was measured linearly, rather than volumetrically. This could be partially due to the intratumor heterogeneity as we could have obtained the specimen from a portion of the tumor that is proliferating differently than other areas within the tumor. Additionally, sample manipulation prior to surgical removal could have led to the cells' behavioral changes from in vivo to in vitro. However, we could not find any specific characteristic such as potential time delay in extracting and processing the sample or the level of cauterization to be indicative of the culture's proliferation rate. Further, since on average 64% of the BrdU-positive cells were S100-positive, it could be that the remainder of proliferating cells, including fibroblasts and other cell types that may be differentially proliferative in vitro versus in vivo, are actually altering the proliferation rate of the culture in comparison to if it was solely comprised of schwannoma cells.

We found no correlation between tumor growth in vivo versus tumor volume, in line with studies that indicate that there is a negative or weak correlation between tumor volume and growth rate (Herwadker, Vokurka, Evans, Ramsden, & Jackson, 2005, Nutik & Babb, 2001; Yoshimoto, 2005). Importantly, our study employed mostly large tumors because smaller tumors are typically not surgically removed (Smouha, Yoo, Mohr, & Davis, 2005) and therefore size could have been a confounder leading to the lack of correlations noted. Additionally, although approximately 4% of all VS are usually cystic in nature (Charabi et al., 1994), our study had 31% VS (4 out of 13) with a cystic component, a characteristic that has been associated with large and symptomatic tumors that are targeted for surgical removal (Nutik & Babb, 2001). In our study, cystic VSs' growth patterns in vivo or in culture could not be distinguished from solid VSs.

Example 2

Role of Nuclear Factor Kappa B in Neoplastic Vestibular Schwannoma Growth

A bioinformatic network analysis of all genes reported to be differentially expressed in human VS revealed a pro-inflammatory transcription factor nuclear factor kappa-B (NF-κB) as a key modulator. The canonical NF-κB complex was found to be aberrantly activated in human VS and derived VS cultures in comparison to nerve specimens and SCs, respectively. Primary VS cells and the NF2 VS cell line were treated with specific NF-κB siRNAs, experimental NF-κB inhibitor BAY11-7082 (BAY11) and clinically relevant NF-κB inhibitor curcumin. All three treatments significantly reduced proliferation in primary VS cultures and NF2 VS cell line, with siRNA, 5 µM BAY11 and 50 µM curcumin reducing average proliferation to 57%, 14% and 23% of non-treated cells, respectively. These treatments also induced substantial cell death. Curcumin, unlike BAY11, also affected primary SCs. Overall, this work highlights NF-κB as a key modulator in VS cell proliferation and survival, making this transcription factor a promising therapeutic target against VS.

Introduction

Although much is known about the different pathways implicated in VS pathobiology, the interconnectedness among these pathways has not been studied. In an attempt to create an interactome of the many biological pathways to identify the major orchestrators of VS growth and progression, we conducted the first comprehensive network analysis of the published genes aberrantly expressed in sporadic VS. Nuclear factor kappa-B (NF-κB), a transcription factor known for mediating the physiological inflammatory response and pathologic processes in several diseases, including neoplastic growth (Hoesel and Schmid, 2013), was identified as a central molecule in a top-ranking network.

Chronic, pathological inflammation has been implicated as a major contributor to neoplastic growth. Current evidence suggests that initially inflammatory cells serve a tumor-immunosurvelliance function by identifying and destroying cells with a neoplastic phenotype (Hoesel and Schmid, 2013). Some of these neoplastic cells evade the immune system and form tumors and continue to outperform the immune system (Hoesel and Schmid, 2013). Inflammatory cells responding to this unregulated group of cells are then recruited to further promote neoplastic growth due to the cytokine and growth factor signals released by the tumor cells and the associated microenvironment, morphing into tumor-associated inflammatory cells (Hoesel and Schmid, 2013). These tumor-associated inflammatory cells then work synergistically by promotion of an anti-apoptotic and pro-proliferative proteome in and around the neoplastic cells. CD163+ tumor-associated macrophages, known to pathologically promote tumor growth and survival, have been identified in VS, with the level of infiltration correlating with the tumor's growth rate (deVries et al, 2013). As deVries et al. mention, understanding the biological basis and pathways through which CD163+ macrophages may promote VS growth will help unravel inflammation's contribution to VS and provide therapeutic targets against this process.

NF-κB, a complex of proteins consisting of a canonical and a non-canonical pathway, can regulate transcription of over 300 downstream genes, which can gravely affect cellular responses with sometimes opposite influences on cell growth, proliferation and survival based on the stimulus and cellular environment (Gilmore, 2014; Hoesel and Schmid, 2013). NF-κB has been implicated as a major regulator of the pathological inflammation in neoplastic growth and its therapeutic inhibition has been investigated in several cancers (Hoesel and Schmid, 2013). NF-κB is especially relevant for VS since merlin acts as a negative regulator of the NF-κB signaling pathway. NF-κB activation and subsequent gene transcription was suppressed by merlin induction in astroglioma and fibroblast cell lines (Kim et al., 2002). Further, a member of the TAM family of receptor tyrosine kinases, Axl, seems to regulate overexpression of survivin and cyclin D1 through NF-κB, leading to enhanced survival, cell-matrix adhesion and proliferation of cultured VS cells (Ammoun et al., 2013).

We investigated NF-κB's aberrance in VS and the therapeutic potential of NF-κB inhibition against VS. We found that NF-κB was activated in VS and VS-derived cultures at significantly higher levels than in healthy nerves and SCs, respectively. We further explored therapeutic efficacy of NF-κB inhibition in primary VS cells and NF2 VS-derived HEI-193 cell line using NF-κB siRNA, an experimental NF-κB inhibitor BAY11-7082 (BAY 11) (Pierce et al., 1997) and a clinically-relevant inhibitor curcumin (Marin et al., 2007) Inhibition of NF-κB using the three different means led to decreased proliferation and survival of primary VS and HEI-193 cells. Potential toxicity of the small molecule inhibitors was tested in primary SC cultures.

In this example, we established NF-κB's aberrance in VS, implicating inflammation as a potential major regulatory process in VS growth and progression. Further, NF-κB inhibition using experimental techniques and a clinically-relevant inhibitor was found to be efficacious, suggesting NF-κB as a promising therapeutic target against VS.

Methods

Ingenuity Pathway Analysis

A literature search was performed with PubMed using MeSH term neuroma, acoustic, combined with the MeSH terms proteins, genes, gene expression, gene expression regulation, gene expression profiling, micorarray analysis, DNA mutational analysis, immunohistochemistry, enzyme-linked immunosorbent assay, tumor suppressor proteins, DNA and RNA. Limits were set to include only research on humans. Articles were selected for inclusion in the study if expression of reported molecules in sporadic unilateral VS was statistically significant at p<0.05 level. Studies without controls or explicit description of statistical criteria were excluded.

Differentially expressed molecules from the selected articles were analyzed using Ingenuity Pathway Analysis (IPA, Ingenuity Systems, Inc., CA), because IPA is based on Ingenuity Knowledge Base—one of the largest curated databases of biological and chemical interactions extracted from the scientific literature. A core analysis was performed with IPA version 9.0 using the Ingenuity Knowledge Base version 3602. We entered differentially expressed molecules into IPA, which created networks by connecting these molecules with other molecules from the Ingenuity Knowledge Base that are known to biologically interact with the input molecules; the interactions can be direct, requiring that two molecules make direct physical contact with each other, without an intermediate step, or indirect if an intermediate step is involved.

Specimen Collection

Specimen collection, comprised of GAN and VS surgical specimens was conducted as outlined in Example 1. The specimen was rinsed with saline (PBS) and divided for protein, RNA or culture work.

Reverse transcription-quantitative polymerase chain reaction (RT-qPCR)

Expression of genes in the NF-κB pathway was measured using real time quantitative PCR (RT-qPCR). Specifically, human VS or GAN tissue was placed in RNA Later (Qiagen, CA) and stored at −20° C. until RNA extraction. Total RNA was extracted using RNeasy Mini-Kit (Qiagen, CA) according to the Manufacturer's protocol. Quantification and quality assessment of the RNA were performed using Agilent 2100 Bioanalyzer (Agilent Technologies, Santa Clara, Calif.) or Nanodrop (ThermoScientific, DE). All samples yielded undegraded RNA as shown by electropherograms or through 260/280 nm absorbance ratios. Isolated RNA was stored at −80° C. The RNA was reverse-transcribed to cDNA with Taqman Reverse Transcription Reagent kit (Applied Biosystems, Foster City, Calif., USA) following the Manufacturer's protocol. The cDNA was stored at either 4° C. for short term or −20° C. for long term. qPCR was performed with TaqMan Primers and 6-FAM linked fluorescent probes (Applied Biosystems, CA) for canonical pathway components: NFKB1 (encoding p50, a subunit of the NF-κB heterodimer, Hs01042010_m1), RELA (encoding p65, a subunit of the NF-κB heterodimer required for activation, Hs01042010_m1) and TNF (tumor necrosis factor, an inducer for NF-κB, Hs01042010_m1); for non-canonical pathway components: RANK (encoding receptor activator of nuclear factor kappa-B, Hs00187192_m1), NFKB2 (Hs01028901_g1), REL (Hs00968440_m1), and RELB (Hs00232399_m1); and for downstream genes with κB sites: CCND1 (encoding cyclin D1, Hs00765553_m1), BCL2 (encoding B-cell lymphoma 2, Hs00608023_m1), CSF2 (encoding colony stimulating factor 2, Hs00929873_m1), and XIAP (encoding X-linked inhibitor of apoptosis, Hs00745222_s1). The primary reference gene was ribosomal RNA 18s (Hs9999901_s1) and the findings were validated using a second reference gene PP1A (Cyclophilin, Hs04194521_s1). The PCR measurements were performed using Applied Biosystems 7700 Sequence Detection System.

Protein Extraction and Western Blot

Translation and activation of the NF-κB pathway components was investigated through western blot analysis. Protein was extracted from VS specimens and cultures as described in Example 1. After quantifying the protein concentration in the tissue lysate using spectrophotometry, protein was loaded at a total protein concentration of 7.5 µg per lane, separated on a 4-20% Tris-glycine gel (Invitrogen, CA) and transferred onto a Polyvinylidene fluoride membrane (Millipore). The membrane was blocked for an hour with 5% Bovine Serum Albumin/PBST (w/v) solution and probed with Cell-Signaling Technology antibodies against NF-κB phosphorylated (P-) p65 (#3033, 1:1000), NF-κB p65 1:2000), NF-κB p50 (1:1000, Abcam, MA), inhibitor of kappa B, alpha (IκBα, 1:1000), followed by corresponding secondary antibodies (Jackson-Immuno Research, PA). Antibody against GAPDH (1:1000, Cell Signaling, MA) served as an internal control. Membranes were visualized with an enhanced chemiluminescence detection system Chemi-Doc Plus (Pierce Laboratories, IL). Band densities were quantified using Image J and were normalized to GAPDH for a given lane.

Immunohistochemistry

Human VS and GAN specimens were fixed in 4% PFA for 2 hours at room temperature (RT) on shaker. The specimens were transferred to PBS and kept on shaker at −4° C. until sectioned to 10 µm thickness. GAN samples were cut in cross-section. Paraffin-embedded tissue on slides was deparafinized with xylene, washed in PBS trice, permeabilized with 0.4% Triton-X 100 (Integra, WA) for 5 min and incubated with 5% normal horse serum (NHS) for 1 hour at RT with gentle agitation. The cells were incubated with primary antibodies against s100 (1:400, Dako, Denmark), a marker for Schwann cells (SC), or p50 (1:100, Abcam, MA) at 4° C. overnight, washed with PBS trice, and incubated for 2 hours at RT in secondary antibodies (Jackson-Immuno Research, PA). Nuclei were labeled by washing the cells twice for 5 min each with Hoechst 3342 stain/PBS (1:500, Invitrogen, CA). The tissue was washed with PBS and a coverslip was mounted with VectaShield (Vector Laboratories, Inc., CA). The tissue was visualized and imaged using Carl Zeiss 2000 upright microscope.

Primary Vestibular Schwannoma, SC and HEI-193 Culture

The same methodology as described in Example 1 was utilized for primary VS and SC cultures. Cultures were treated with NF-κB inhibitors approximately after 2 weeks of culturing. HEI-193 cell line was a gift from Dr. Giovannini at the House Ear Institute (Hung et al., 2002a).

Pharmacologic Treatment of Cultures with NF-κB siRNA, BAY 11-7082 and Curcumin

For siRNA treatment, cultured primary VS cells or HEI-193 cells were placed in antibiotic and serum free media overnight. The next day, the cells were incubated with Life Technologies siRNAs targeting NF-κB genes RELA and NF-κB1, with control cells being treated with vehicle only (Lipofectamine RNAiMax), for 5 days. Some cultures were also incubated with a fluorescent random Oligo (Life Technologies) along with vehicle to assess transfection efficiency. siRNA experiments were performed in antibiotic and serum free media.

Cultured human primary VS cells, primary SCs and HEI-193 cells were treated with NF-κB inhibitors BAY11-7082 (BAY11) or curcumin for 48 hours (Santa Cruz Biotechnology). BAY11 or curcumin, diluted in 100% DMSO, were mixed to the accurate concentrations in warmed media and applied to the cultures (with DMSO concentration in media being 1% maximum), alongside a no-treatment control receiving media alone with appropriate corresponding DMSO levels. Experiments were performed in media fortified with antibiotics and serum (same formulation as described in Example 1 for culturing cells).

Proliferation and Apoptosis Assay

After 48 hours of treatment, primary VS and Schwann cultures were fixed for BrdU staining, to visualize proliferation, or TUNEL staining, to visualize cell death. The same methodology as described in Example 1 was utilized. Cleaved caspase 3 staining, another apoptosis marker to reinforce findings using TUNEL, was conducted using an antibody against cleaved caspase 3 following the 'immunofluorescence' protocol outlined in Example 1.

Statistical Analyses

The networks were analyzed by IPA with the right-tailed Fisher's exact test with a $p<0.05$ being considered significant. Statistical significance was determined using the two-tailed t-test for qPCR and western blot analyses. Paired two-tailed t-test was used to compare differences in proliferation and cell death after treatment. The p-values for multiple comparisons were adjusted using the Benjamini-Hochberg adjustment for false discovery rate, with a $p<0.05$ considered significant.

Results

Figure 3:
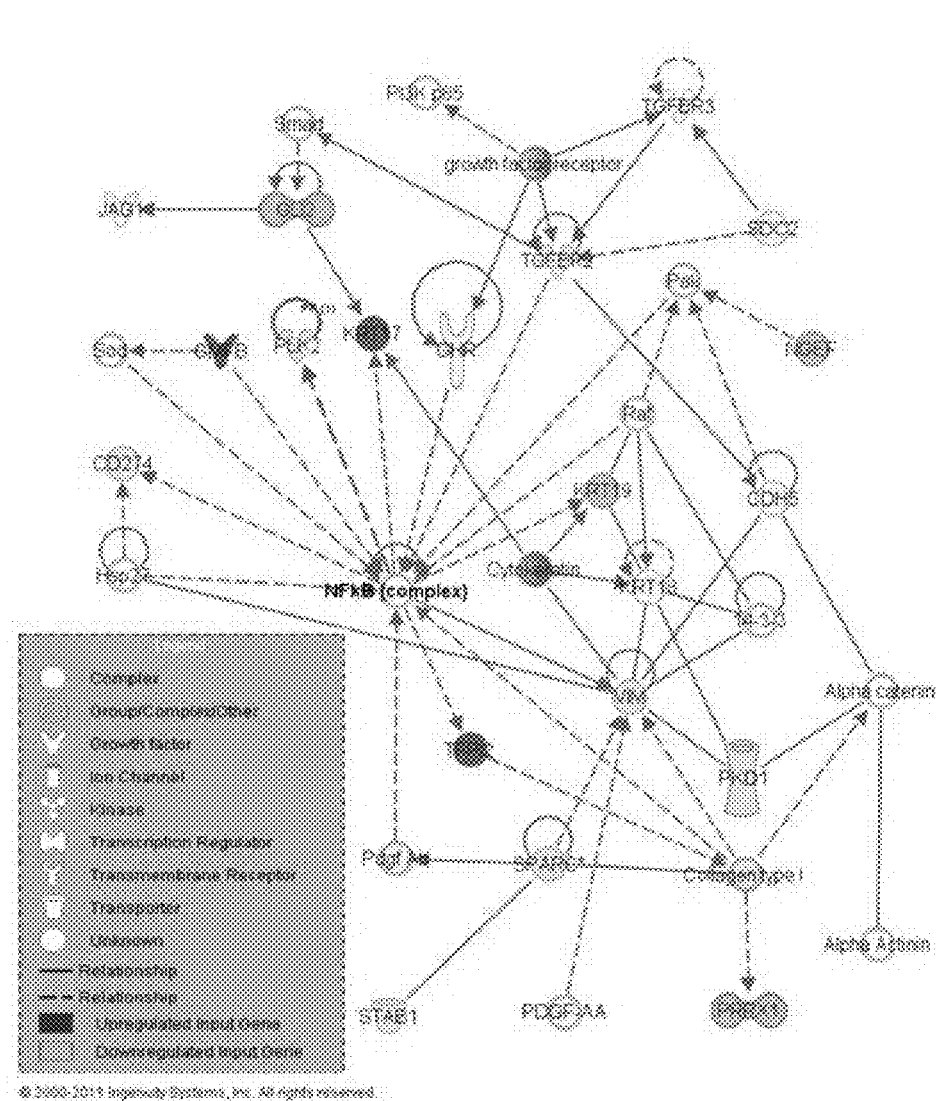
FIG. 3 is the highly significant network that connects molecules reported to be aberrantly expressed in VS with other molecules from the Ingenuity Knowledge Base. Light grey: downregulated, Dark grey: upregulated molecules implicated in VS pathobiology. Significance of this network was 10-33. The hub of this network is nuclear factor kappa B (NF-κB) complex, consisting of NFKB1, NFKB2, RELA, RELB and REL genes. Solid lines represent direct and dashed lines represent indirect interactions.
Figure 4:
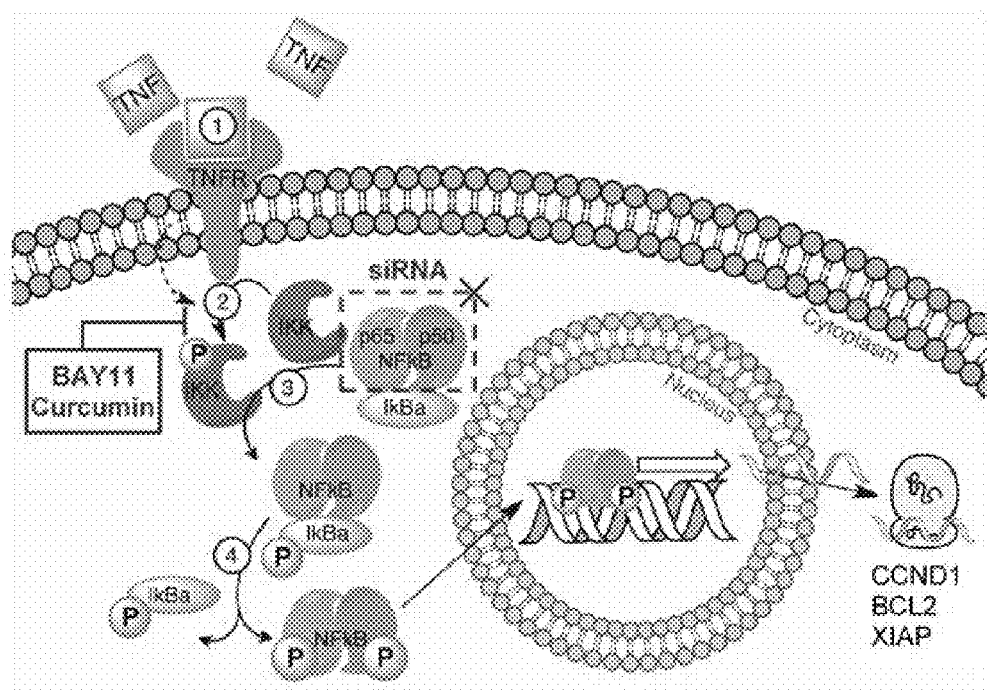
FIG. 4 is a schematic of the canonical NF-κB activation cascade. Schematic designed after published description by Karin, 1999. Inhibitors used against NF-κB: NF-κB siRNA targeting RELA and NFKB1, genes that encode p65 and p50 subunits, respectively; BAY11 and curcumin that inhibit phosphorylation of IκK, disabling phosphorylation of IκBα and consequent activation of NF-κB (Pierce et al., 1997; Marin et al., 1999).

Ingenuity Pathway Analysis Demonstrates Nuclear Factor Kappa-B (NF-κB) as a Central Modulator of VS Growth Of the 622 articles that were found with the literature search, 19 met our inclusion criteria. These articles used microarray analysis, immunohistochemistry, western blotting, northern blotting and PCR to study molecules of interest. After removing duplicates and applying fold change and FDR cutoffs, these 19 articles generated 221 molecules eligible for generating networks: 162 overexpressed and 59 underexpressed molecules in sporadic VS relative to non-neoplastic control tissue. IPA generated a total of 19 networks. The top ranking network, included merlin, which was directly linked to the network's hub, thus validating our approach. Here we focus on validation of the hub of the second most significant ($p=10^{-33}$) network (FIG. 3): NF-κB, a key pro-inflammatory transcription factor. We focus on NF-κB because inflammation is important for tumorigenesis of various neoplasms and has been little studied in VS. At the time of this analysis (April 2011), no studies demonstrating NF-κB's role in VS had been published. To validate our bioinformatic result pointing to NF-κB and TNFα as possible important orchestrators of VS development and proliferation, we have conducted several experiments to elucidate the role of NF-κB. A schematic for NF-κB activation is shown in FIG. 4. When an inducer such as TNFα binds to its receptor TNFR, inhibitor of kappa B kinase (IκK) is activated, leading to phosphorylation and degradation of inhibitor of kappa B alpha (IκBα) (Karin, 1999). This enables the heterodimer of NF-κB p65 and p50 to be phosphorylated in the cytoplasm and relocate to the nucleus to promote transcription of genes important for survival and proliferation.

RT-qPCR Shows Aberrant Expression of TNF-induced NF-κB Pathway in Sporadic VS

Figure 5:
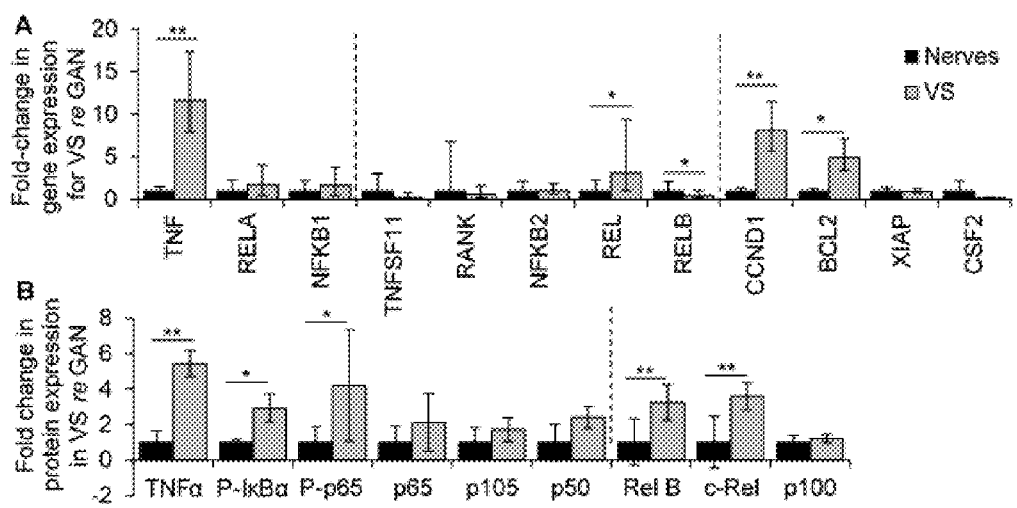
FIG. 5 is a graph demonstrating that NF-κB is aberrantly activated in VS. A. NF-κB pathway expression in human VS (n≥9) versus great auricular nerve (nerves, n≥8) as measured through qPCR. Dashed lines separate genes by groups, being genes associated with canonical NF-κB pathway, non-canonical NF-κB pathway and downstream NF-κB-regulated genes, *p<0.05, **p<0.01, error bars represent range; B. NF-κB pathway expression in human VS (n≥4) versus GAN (n≥4) as quantified through western blot analysis; P− means phosphorylated protein. Dashed line separates canonical proteins from non-canonical proteins, *p<0.05, **p<0.01, error bars represent SD; GAN (nerves) and VS expression is shown in black and grey bars, respectively, for panels A and B.

We quantified differences in expression of several NF-κB-related genes in VS as compared to GAN using qPCR. Generally, the canonical and non-canonical NF-κB pathways were not found to be significantly different in VS. The data are expressed as the average with range of expression in parentheses. Benjamini-Hochberg adjusted p-values are given. In the canonical pathway, genes NF-κB1 (encoding the p50 subunit) and RELA (encoding the p65 subunit) were 1.75 (1.3-2.3) (p=0.18) and 1.63 (1.2-2.2) (p=0.17) fold higher, respectively when comparing 10 tumors with 10 nerves (FIG. 5A). With the average being normalized to be 1, the range of expression GAN was 0.9-1.6 and 0.8-1.3 for NFKB1 and RELA, respectively. Non-canonical NF-κB components REL, RELB and NF-κB2 exhibited different patterns of expression. REL was 3.1 (1.0-9.4) fold-higher in VS (n=13) than GAN (n=10) (p=0.01, FIG. 5A).

NFKB2 had the same average expression in VS (range 0.6-1.8, n=13) as GAN (range 0.4-2.2, n=10) (p=0.22, FIG. 5A). RELB, interestingly, was substantially downregulated in VS (n=13), being 0.4 (0.2-1.0) fold of GAN (n=10, range 0.5-2.1) (p=0.02, FIG. 5A).

Exploring the downstream genes with κB binding sites, two genes under canonical NF-κB control were significantly upregulated in VS (n=15) relative to GAN (n=15): pro-proliferative CCND1 at 8.1 (5.7-11.5) (p=0.0007) and anti-apoptotic BCL2 at 4.9 (3.3-7.1)-fold (p=0.02) (FIG. 5A). The ranges in GAN were 0.7-1.4 and 0.8-1.3 for CCND1 and BCL2, respectively. Anti-apoptotic XIAP, was not significantly changed, with an equal average expression in VS (n=12) as GAN (n=7) and a range of 0.7-1.3 in VS and 0.7-1.4 in GAN (p=0.18, FIG. 5A) and pro-proliferation CSF2, was substantially downregulated in VS (n=9), being 0.11 (0.06-0.20)-fold of GAN, although it did not meet significance (p=0.11, FIG. 5A). The range of expression in GAN (n=7) was 0.5-2.2.

The canonical NF-κB pathway was not upregulated in VS, although its downstream genes were upregulated. We also found, for the first time, that the non-canonical pathway gene REL are upregulated in VS. Using qPCR, we also explored the upstream regulators of canonical and non-canonical NF-κB pathways, being TNFα and RANKL, respectively. We found TNF, encoding TNFα, to be expressed at significantly higher levels in VS, being 11.7 (7.9-17.4)-fold higher in VS (n=10) than in GAN (n=10, range 0.7-1.5) (p=0.003) (FIG. 5A). RANKL gene TNFS11 was not significantly different in VS versus GAN, being 0.22 (0.08-0.60)-fold expression in VS (n=10) of GAN (n=10, range 0.5-2.0) (p=0.20) (FIG. 5A).

Western Blot Analysis Reveals Aberrant Activation of the NF-κB Pathway in Sporadic VS NF-κB translation and activation was assessed using western blot analysis. Data are summarized as average fold change±standard deviation. Benjamini-Hochberg adjusted p-values are given. Western blot analysis revealed that NF-κB canonical pathway, although expressed at similar levels as GAN as seen through qPCR, is activated at significantly higher levels. NF-κB p65 (encoded by the RELA gene) had 2.1±1.7-fold higher expression in VS (n=10) in comparison to GAN (n=9) (p=0.09, FIG. 5B). The phosphorylated form of p65 was significantly higher in VS, being 4.2±3.1-fold higher in VS (n=9) in comparison to GAN (n=8) (p=0.03, FIG. 5B). NF-κB p105 (encoded by the NF-κB1 gene) had 1.7±0.7-fold higher expression in VS (n=7) in comparison to GAN (n=7) (p=0.14, FIG. 5B). p105's derived subunit p50 was 2.4±0.6-fold higher expression in VS (n=15) in comparison to GAN (n=11) (p=0.10, FIG. 5B). NF-κB's canonical inducer, TNF, was 5.4±0.7-fold higher expression in VS (n=4) than GAN (n=4) (p=0.001, FIG. 5B), following the same trend as seen through qPCR. Additionally, the phosphorylated form of IκBα was also significantly higher in VS (n=4) than in GAN (n=4), being 2.8±0.8-fold higher (p=0.01, FIG. 5B). Although expression for p50 and p65 was not significantly higher in VS, both proteins had a trend of being present at higher levels, suggesting a potential post-transcriptional regulation leading to higher levels of these proteins being translated. Since an antibody that detects only phosphorylated p50 was not available, we could not test p50's activation status.

The NF-κB non-canonical subunits c-Rel (encoded by REL gene) and p100 (encoded by NF-κB2 gene) had the same trend as seen in qPCR. c-Rel had 3.6±0.8-fold higher expression in VS (n=7) in comparison to GAN (n=7) (p=0.003, FIG. 5B). p100 did not have higher expression, being 1.2±0.2-fold in VS (n=4) in comparison to GAN (n=4) (p=0.42, FIG. 5B). Interestingly, Rel-B (encoded by RELB) was significantly higher in VS when looking at protein expression in VS, although it was substantially lower when looking at RNA expression through qPCR. It was 3.3±1-fold higher expression in VS (n=7) than GAN (n=7) (p=0.006). Other than for Rel-B, a high level of consistency was noted between qPCR and western blot results.

The internal control protein, GAPDH, was not significantly different between VS and GAN (p=0.36). These results demonstrate presence and basal activation of NF-κB in GAN and VS, and substantially higher activation of the NF-κB pathway in VS.

Immunohistochemistry Highlights Aberrant NF-κB Activation in VS

Immunohistochemistry (IHC) verified that NF-κB was active in VS as the p50 subunit localized to the nuclei in VS specimens (n=5 different VS). GAN specimens showed minimal p50 nuclear localization although p50 was present in the cytoplasm (n=4 different GAN). This is in concert with the western blot results demonstrating a higher level of phosphorylation, and hence activation of NF-κB in VS. s100, a marker for SCs, highlights schwannoma cells in VS specimens and SCs encasing the nerve fibrils in GAN. Additionally, CD163-positive tumor-associated macrophages were present in the same VS specimens (n=4 different VS) at substantially higher levels than in GAN (minimal CD163-positive staining noted, n=4 different GAN). Both schwannoma and CD163 cells demonstrated activated NF-κB, as assessed by overlapping s100 or CD163 stain with p50 nuclear localization.

Western Blot Analysis Reveals Aberrant Activation of the NF-κB Pathway in Primary VS Cultures The NF-κB canonical pathway was found to be expressed and activated at significantly higher levels in primary VS cultures (n=6) in comparison to SC cultures (n=6). NF-κB p65 had 1.9±0.4-fold higher expression in VS cells in comparison to SCs (p=0.01, FIG. 6A). The phosphorylated form of p65 was significantly higher in VS, being 2.8±0.4-fold higher in VS cells in comparison to SCs (p=0.02, FIG. 6A). NF-κB p105 had 0.9±0.4-fold higher expression in VS cells in comparison to SCs (p=1.0, FIG. 6A). p105's derived subunit p50 had 1.7±0.4-fold higher expression in VS cells in comparison to SCs (p=0.06, FIG. 6A). Although p50 and p65 expression was not significantly higher in VS versus GAN specimens, both proteins had a trend of being present and activated at a similar magnitude as in the cultures. These results validate our primary culture model to study NF-κB.

NF-κB siRNA Decreases Proliferation and Survival of Specific VS Cultured Cells

To assess NF-κB's role in VS, primary human VS cultures were treated with three different NF-κB inhibitors, namely siRNA (targeting the canonical NF-κB components RELA and NF-κB1), BAY11 and curcumin. The postulated mechanisms are that siRNA acts to silence the NF-κB genes whereas BAY11 and curcumin act by inhibiting its activation (FIG. 4). siRNA is considered highly specific whereas BAY11 and curcumin could have multiple targets.

Figure 6:
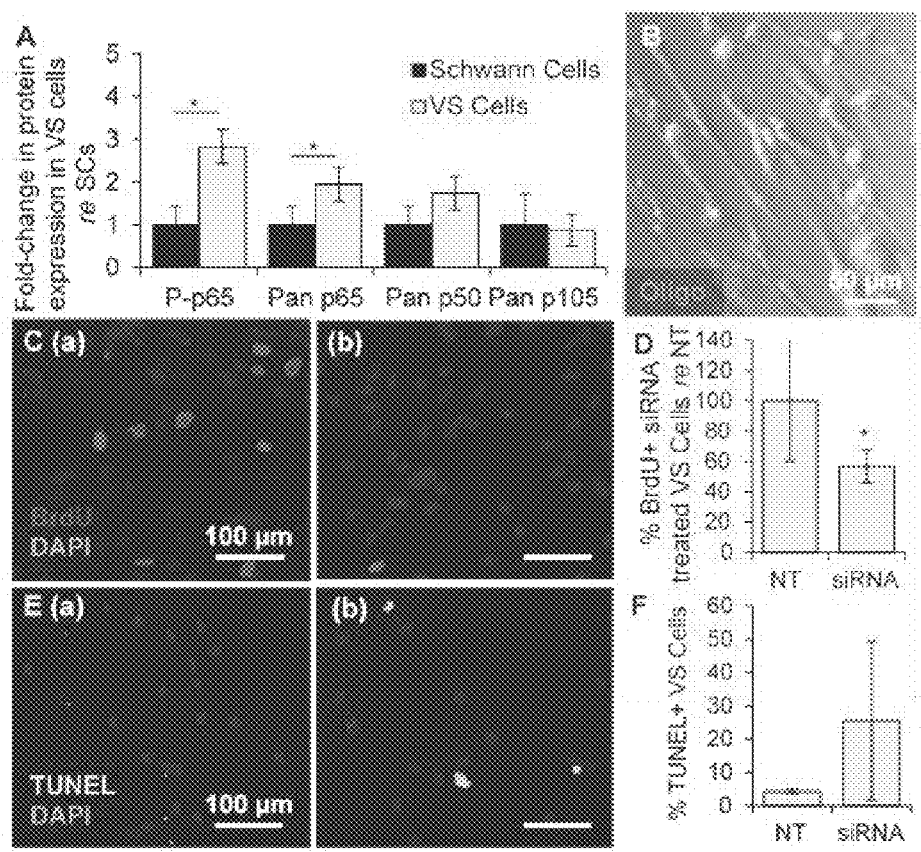

We were able to achieve a transfection efficiency of approximately 94±3% in primary VS cells (n=3), as assessed by transfection of a fluorescent red-labeled oligo (FIG. 6B). Applying both siRNAs concurrently and thereby knocking down the canonical NF-κB p50 and p65 complex to VS cultures led to a decrease in proliferation, as measured by nuclear BrdU staining, and cell survival, as measured by the TUNEL assay. Results are summarized as average±standard error of mean (SEM). Benjamini-Hochberg adjusted p-values are given. Proliferation changes are normalized to each culture's proliferation rate. Basal proliferation in VS cultures treated with vehicle was 6.5%±2.6% (n=4, FIGS. 6C (a), 6D). Proliferation significantly decreased to 56.9%±10.7% of the no-treatment levels after siRNA treatment (n=4, p=0.04, FIGS. 6C (b), 6D). Percentage of VS cells treated with vehicle only exhibiting TUNEL staining was 4.3%±0.7% (n=3, FIGS. 6E (a), 6F). Cell death increased to 25.6%±23.79% in VS cultures treated with NF-κB siRNA, although the increase did not meet our criterion of significance (n=3, p=0.38, FIGS. 6E (b), 6F). These findings were in line with qPCR results that demonstrated elevated level of downstream NF-κB pro-proliferative and survival genes of CCND1 and BCL2, respectively, in VS.

To assess the role of NF-κB in NF2-associated VS also, we utilized NF-κB siRNAs on the NF2 VS HEI-193 cell line. Here, we found that knockdown of NF-κB led to a potent and specific decrease in proliferation, reducing proliferation from 25.4% for vehicle only to 0%. Cell death did not change, going from 2.2% to 3.0% for vehicle only and siRNA-treated cells. These findings suggest a key role for NF-κB in modulating VS cell proliferation.

Figure 7:
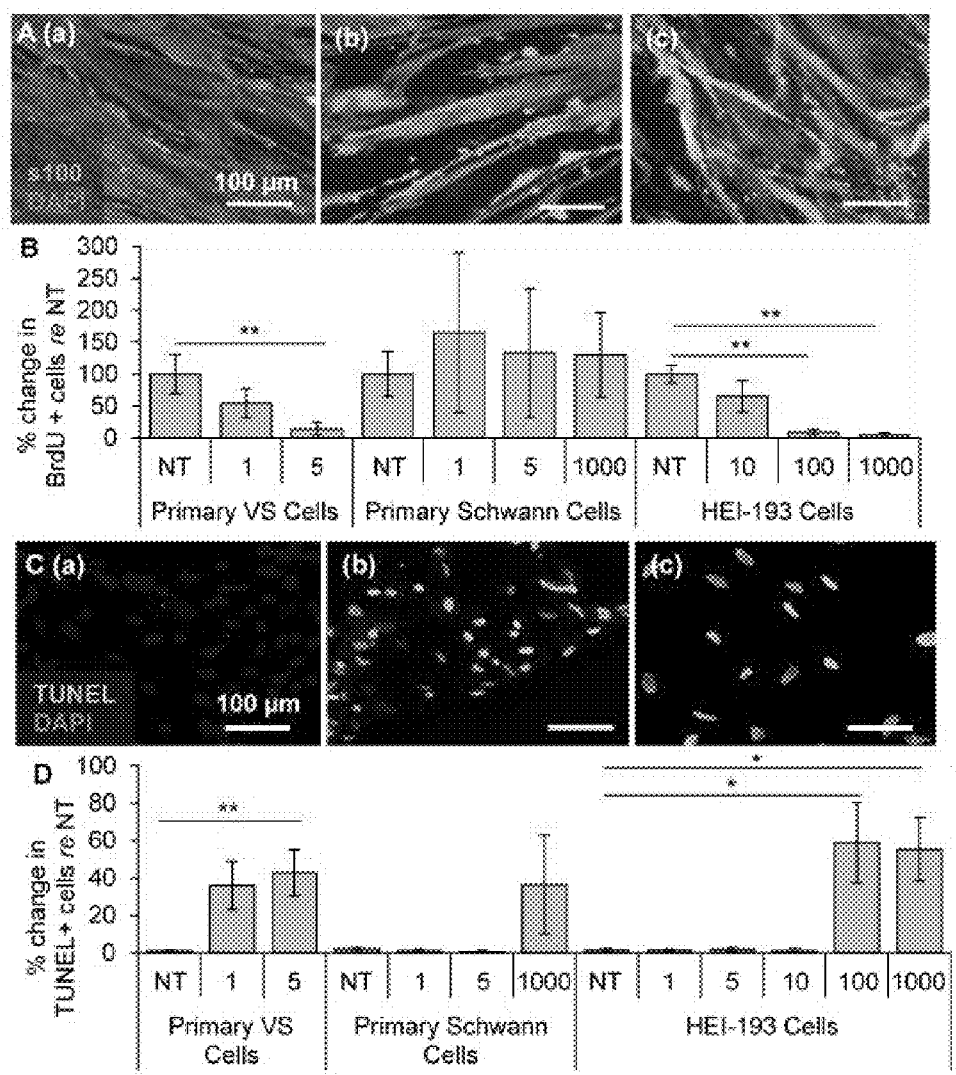
FIG. 7 is a collection of images and graphs demonstrating that NF-κB inhibitor BAY11-7082 leads to selective decrease in proliferation and survival of VS cells. A. Representative proliferation images are shown for primary VS cultures treated with no treatment (a, NT), 1 µM (b) and 5 µM (c) BAY11-7082 (BAY11). BrdU in nuclei marks proliferating cells, S100 marks schwannoma cells, nuclei are labeled with DAPI, Scale bar=100 µm for all images; B. Quantification of proliferation changes after treatment with BAY11 at different concentrations (given in µM) in primary VS cells, primary SCs and HEI-193 NF22 VS cell line, all normalized to proliferation in control non-treated cells (n≥3); C. Representative cell death images are shown for primary VS cultures treated with no treatment (a, NT), 1 µM (b) and 5 µM (c) BAY11-7082 (BAY11). TUNEL (light grey) in nuclei marks dying cells, nuclei are labeled with DAPI, Scale bar=100 µm for all images; D. Quantification of cell death rate changes after treatment with BAY11 at different concentrations (given in µM) in primary VS cells, primary SCs and HEI-193 NF2 VS cell line (n≥3), *p<0.05, **p<0.01, re=in comparison to; Error bars represent SEM.

NF-κB Small-Molecule Inhibitor BAY 11-7082 Decreases Proliferation and Survival Selectively in Cultured Primary VS Cells and NF2 VS Cell Line Primary VS cells, control SC cultures and the NF2 VS HEI-193 cell line were treated with BAY11. Data are summarized as average±standard error of mean. Benjamini-Hochberg adjusted p-values are given. Proliferation changes are normalized to each culture's proliferation rate. After treatment, proliferation changed in VS cells to 54.7±22.8% (n=5 different VS cultures, p=0.15, FIGS. 7A (b), 7B) and 14.3±9.7% (n=4 different VS, p=0.002, FIGS. 7A (c), 7B) of the non-treated cells (NT, FIG. 7A (a)) with 1 μM and 5 μM BAY 11, respectively. The cell death rate changed from 1.1±0.27% (FIGS. 7C (a), 7D) in the NT cultured VS cells to 36±13% (n=7 different VS, p=0.06. FIGS. 7C (b), 7D) and 47±12% (n=8 different VS, p=0.02, FIGS. 7C(c), 7D) in cells treated with 1 μM and 5 μM BAY 11, respectively.

In the control SC cultures (n=3 cultures, each derived from a different GAN), normalized proliferation rates did not change significantly, being 100.0±34.7%, 165.2±125.1% (p=0.70), 133.2±101.1% (p=0.69), 130.2±65.6% (p=0.78), for NT, 1 µM, 5 µM and 1 mM BAY 11 treated cells, respectively (n=3 different VS cultures, FIG. 7B). SCs demonstrated higher cell death only at 1 mM BAY 11 with NT; 1 µM, 5 µM or 1 mM treated GAN cells exhibiting apoptosis rates of 2.0±0.9%, 1.0±0.7% (p=0.53), 0.7±0.7% (p=0.47) and 36.5±26.5% (p=0.43) (n=3, FIG. 7D). Combing the results from BAY11-treated primary VS and SC cultures, an effective therapeutic window to target VS cells seems to be around 5 µM.

BAY11 treatment also decreased HEI-193 cell survival in a dose-dependent manner. HEI-193 cells had very high basal proliferation rates, being 84.9±11.7% (n=3 different experiments). NT, 10, 100 µM and 1 mM BAY 11 treated HEI-193 cells exhibited normalized proliferation rates of 100.0±13.8%, 65.6±24.6% (n=5, p=0.25) 9.1±4.9% (n=5, p=0.006) and 4.3±3.3% (n=5, p=0.003), respectively (FIG. 7B). NT, 1, 5, 10, 100 µM and 1 mM BAY 11 treated HEI-193 cells exhibited cell death rates of 1.3±0.8%, 1.3±0.5% (n=6, p=0.22), 1.9±1.2% (n=6, p=0.26), 1.1±1.1% (n=5, p=0.63) 58.8±21.5% (n=5, p=0.04) and 55.3±16.9% (n=5, p=0.02), respectively (FIG. 7D). These results demonstrate that BAY11 decreased proliferation and survival of HEI-193 cells in a dose-dependent manner.

Cleaved Caspase-3 staining, done for primary VS cells and HEI-193 cells, exhibited the same dose-dependent patterns, with higher rates of positive caspase-3 staining at all concentrations. This can be attributed to the fact that caspase-3 stains dying cells at all stages including and past early apoptosis, whereas TUNEL staining highlights dying cells only at the late apoptosis stage.

Clinically-relevant NF-κB Inhibitor Curcumin Decreases Proliferation and Survival in Cultured Primary VS Cells, NF2 VS Cell Line and Primary SCs Curcumin, a natural NF-κB inhibitor derived from turmeric that is currently in several clinical trials for various neurological and inflammatory diseases ranging from Alzheimer's disease to colon cancer (Hatcher et al., 2008; clinicaltrials.gov), was also tested to assess efficacy in VS cells. Our results show curcumin as a promising therapeutic against VS as it selectively targeted VS cells in culture and is known to be well-tolerated. Data are summarized as average±standard error of mean. Benjamini-Hochberg adjusted p-values are given. Proliferation decreased in a dose-dependent manner in VS cultures, with VS cells receiving NT (FIG. 8A (a)), 5 µM (FIG. 8A (b)), 20 µM (FIG. 8A (c)) and 50 µM (FIG. 8A(d)) curcumin exhibiting normalized proliferation rates of 100.0%±30.5%, 141.8%±95.2% (p=0.57), 23.0±20.9% (p=0.03) and 9.8±5.3 (p=0.0005) (n=3 different VS, FIG. 8B). Cell death also increased in a dose-dependent manner, with VS cells receiving NT (FIG. 8C (a)), 5 µM (FIG. 8C (b)), 20 µM (FIG. 8C (c)) or 50 µM (FIG. 8C (d)) exhibiting cell death rates of 0.3±0.1, 11.6±6.3% (n=8, p=0.37), 1.8±1.0% (n=3, p=0.37) and 73.3±6.3% (n=7, p=0.0005) (FIG. 8D).

Surprisingly, in contrast to the seemingly well-tolerated profile for curcumin in humans, curcumin also led to decreased proliferation and increased cell death in control SC cultures at concentrations comparable to those efficacious in VS cultures. Proliferation demonstrated a trend towards a decrease in a dose-dependent manner, with SCs receiving NT, 5 µM, 20 µM, 50 µM curcumin exhibiting normalized proliferation rates of 100.0%±29.6%, 85.3±25.7% (n=4, p=0.33), 31.0±18.3% (n=4, p=0.13) and 3.14% (n=1, p=0.04) (FIG. 8B). The trend became significant only at the highest tested dose. Cell death increased, with NT, 5 µM, 20 µM or 50 µM treated GAN cells exhibiting cell death rates of 0.6±0.2, 1.3±0.3% (n=4, p=0.16), 1.7±0.4% (n=4, p=0.31) and 52.2±14.9% (n=5, p=0.03) (FIG. 8D).

Intriguingly, the HEI-193 cells were more susceptible to curcumin than primary VS cells or even healthy SCs. They exhibited a very drastic level of both decreased proliferation and increased cell death starting at the 20 µM treatment, in contrast to the primary cells exhibiting cell death at 50 µM. Proliferation decreased drastically with dose increases, with HEI-193 cells receiving NT, 5 µM, 20 µM or 50 µM curcumin exhibiting normalized proliferation rates of 100.0%±0.2%, 95.0±1.6% (p=0.12), 0.4±0.4% (p=0.0001) and 2.3±2.3% (p=0.001) (n=3 different experiments, FIG. 8B).

Figure 8:
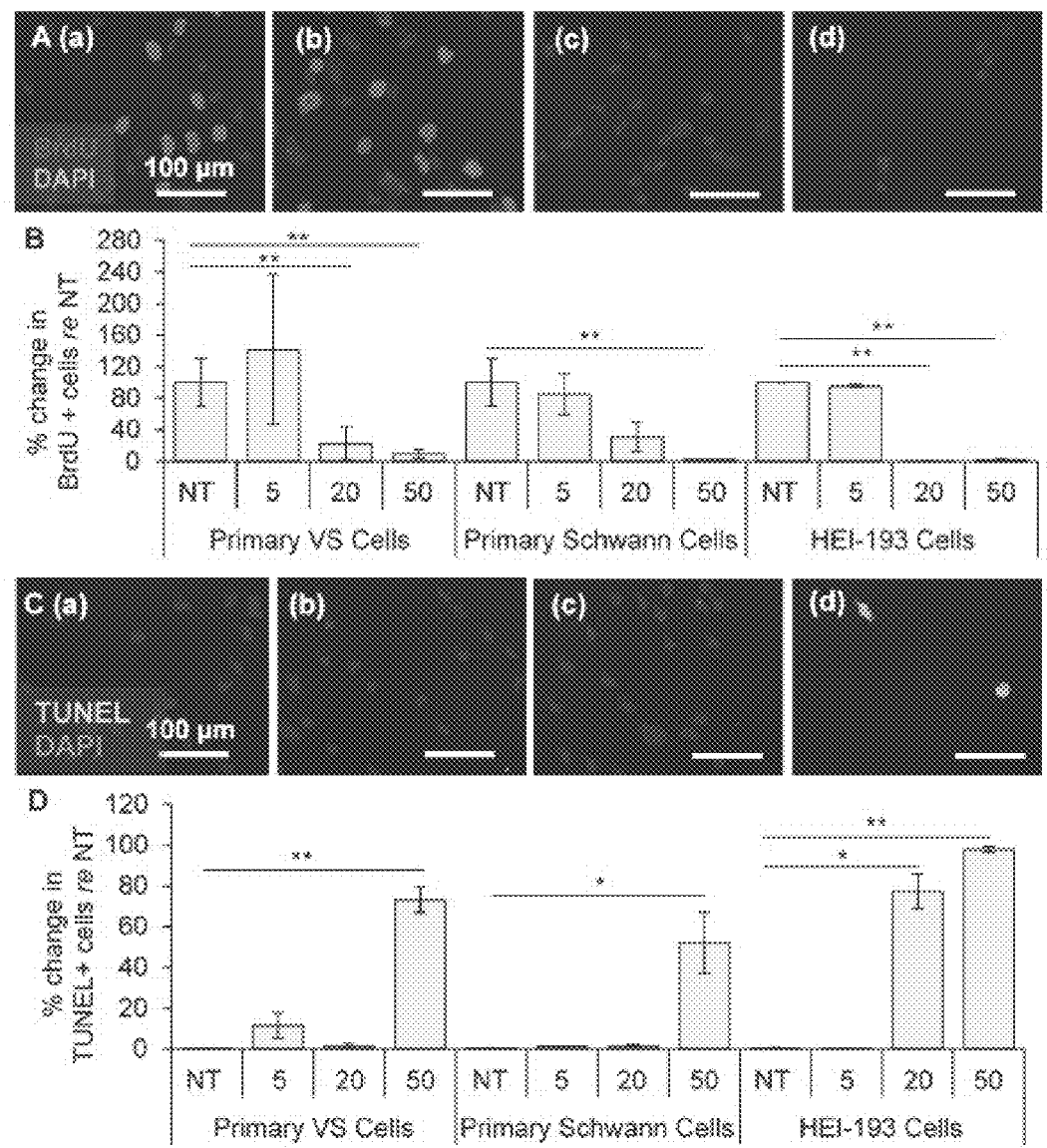
FIG. 8 is a collection of images and graphs demonstrating that the clinically-relevant NF-κB inhibitor curcumin leads to selective decrease in proliferation and survival of VS cells. A. Representative proliferation images are shown for primary VS cultures treated with no treatment (a, NT), 5 µM (b), 20 µM (c), and 50 µM (d) curcumin. BrdU in nuclei (red in original) marks proliferating cells, nuclei are labeled with DAPI, Scale bar=100 µm for all images; B. Quantification of proliferation changes after treatment with curcumin at 5, 20, and 50 µM (given in µM) in primary VS cells, primary Schwann cells and HEI-193 NF22 VS cell line, all normalized to proliferation in control non-treated cells (n≥3); C. Representative cell death images are shown for primary VS cultures treated with NT (a), 5 µM (b), 20 µM (c), and 50 µM (d) curcumin. TUNEL (green in original) in nuclei marks dying cells, nuclei are labeled with DAPI, Scale bar=100 µm for all images; D. Quantification of cell death rate changes after treatment with curcumin at 5, 20, and 50 µM (given in µM) in primary VS cells, primary Schwann cells and HEI-193 NF2 VS cell line (n≥3), *p<0.05, **p<0.01, re=in comparison to; Error bars represent SEM.

Cell death also increased drastically at the 20 µM concentration, with HEI-193 cells receiving NT, 5 µM, 20 µM or 50 µM curcumin exhibiting cell death rates of 0.5±0.4, 0.3±0.1% (n=5, p=0.32), 77.3±8.4% (n=3, p=0.02) and 97.8±1.5% (n=4, p=0.00003) (FIG. 8D). Cleaved caspase-3 staining in the cultures exhibited the same dose-dependent patterns, with generally higher rates of positive caspase-3 staining than TUNEL staining at all effective concentrations.

Discussion

Conducting the first comprehensive bioinformatic network analysis of molecules implicated in VS pathobiology, we identified a central regulator, NF-κB. Transcription factor NF-κB is a key mediator of pro-inflammatory responses, promoting expression of genes attributed to cell survival and proliferation in the context of neoplastic growth (Heosel and Schmid, 2013). We also found direct interactors of NF-κB, which have been implicated as important VS progression modulators, to be central nodes in other networks. PDGFBB and MAPK were highly significant as central nodes of other networks generated by IPA, highlighting the potential significance of the PDGF-modulated NF-κB activation leading to MAPK upregulation in VS growth (Olson et al., 2007).

Motivated by our bioinformatic result, we explored the aberrance of NF-κB in VS and its relevance as a therapeutic target against VS. We found that the canonical NF-κB pathway, consisting of NF-κB p65 and p50, was aberrantly activated in VS. We found that this aberrance was also present in primary VS cultures. This is in line with previous findings showing significantly higher NF-κB activation in VS in comparison to healthy SCs (Ammoun et al., 2013). Additionally, we found that the non-canonical pathway component REL, encoding c-Rel subunit, were upregulated and expressed at significantly higher levels. c-Rel can form heterodimers with p50 or p65 or form a homodimer, all leading to increased survival and proliferation of healthy B-cells or neoplastic cells, such as in lymphomas (Gilmore et al., 2004). Interestingly, CSF2, a gene regulated by c-Rel and associated with malignancies, was downregulated in VS. It may be interesting to study c-Rel's role in VS in future work.

We focused on the canonical pathway as it most commonly implicated in neoplastic growth (Hoesel and Schmid, 2013) and we found it consistently abnormally activated in VS in our work. Merlin-deficient cultured VS cells are known to have aberrantly high levels of NF-κB, which can be decreased by merlin re-introduction (Ammoun et al., 2013). As all prior experiments had been conducted on cultured cells and cell lines, we are the first to show that this aberrant activation occurs also in the VS specimens and cannot be deemed an artifact due to culturing. We consistently found NF-κB localized to the nucleus in VS specimens, a feature that was lacking in GAN specimens. This contrast between VS and GAN also provides some affirmation that NF-κB was inherently active in VS, rather than being activated due to turbulence during surgical resection as the VS and GAN samples are both collected during surgical resections.

It is interesting to compare NF-κB's role in VS pathobiology and its role in SC development. Nickols et al. found NF-κB to be essential for differentiation of pre-mature SC's into myelinating SCs, with NF-κB expression progressively declining from pre-myelinating SCs to near absence in adult SCs (Nickols et al., 2003). Our findings reinforce previous findings of schwannomas exhibiting a gene expression profile akin to immature SCs (Hung et al., 2002b), and support the hypothesis that an excess of precursor SCs make the vestibular nerve the predilection site for schwannomas. This potentially pre-existing upregulation of NF-κB, along with a few defining mutations in other modulator genes, could lead to the pathogenotype enabling axon-independent, neoplastic SC proliferation.

Exploring downstream NF-κB genes, we found some were substantially upregulated in VS, i.e. cyclin D1 (Toualbi-Abed et al., 2008) and BCL2 (Catz et al., 2001), while others were unchanged or had a trend of downregulation, XIAP (Turner et al., 2007) and CSF2. Interestingly, CSF2 is a pro-proliferative gene associated with malignant transformation with a non-canonical c-Rel (encoding by gene REL) binding site (Bunting et al., 2007), and REL was actually upregulated in our analysis. The downstream genes overall had an interesting expression pattern suggesting a unique NF-κB target gene program in VS, in line with literature that shows that transcription factors can modulate different genes based on stimuli. In pathologic inflammation, NF-κB would be expected to have a unique program in contrast to a typical physiological response (Heosel and Schmid, 2013).

Our work with freshly harvested VS samples from different patients allowed us to capture the potential variability of NF-κB aberrance in VS. Our results suggest that therapeutic targeting of NF-κB may be generally effective against VS, not only against a small subset of VS. Further, we utilized three different modalities to inhibit NF-κB, the first being highly-specific siRNAs against the NF-κB canonical subunits p50 and p65, second being a pharmacologic inhibitor, BAY11, and the third being a clinically-relevant, natural NF-κB inhibitor curcumin, in order to affirm NF-κB's role and to expedite translation of a potential pharmacotherapy against VS. BAY11 and curcumin act by inhibiting IκK activation, leading to inhibition of phosphorylation and consequent activation of NF-κB. Effective, targeted inhibition of NF-κB with small-molecule inhibitors, including curcumin, has been a focus in clinical research to control the neoplastic growth.

Targeting canonical NF-κB p65 through siRNA knockdown reduced primary VS cell growth, survival and cell-matrix adhesion in previous work (Ammoun et al., 2013). Our results reinforce these findings. We further expand these findings since we noted reduced proliferation also in the HEI-193 cell line after siRNA-mediated knockdown of both the canonical NF-κB p65 and p50 subunits. Unlike in the primary VS cells, the effect was specific to cell proliferation. It may be that NF-κB is not controlling survival genes such as BCL2 in the case of HEI-193 cells. Our results highlight NF-κB's regulatory roles in promoting VS growth and survival, potentially through regulation of pro-proliferative CCND1 and anti-apoptotic BCL2 upregulated in VS, both genes known to be regulated by NF-κB. CCND1 previously has been shown to decrease in expression after NF-κB knockdown in VS cells (Ammoun et al., 2013).

BAY11 showed a high level of efficacy and specificity against VS cells. BAY11's mechanism of action is unclear in our study. Although BAY11 has been characterized as an effective inhibitor of NF-κB, recently, many other targets, including TNF, have been discovered (Lee et al., 2012). It is thought to generally inhibit the inflammasome and other inflammation-related processes (Lee et al., 2012). Focusing on NF-κB and inflammation more generally, BAY11 could target this pathological process in VS cells. Further, BAY 11 was also not found to be cytotoxic in primary SCs and has been used in vivo in murine tumor xenograft studies (Dewan et al., 2003), suggesting its potential specificity in targeting neoplastic cells. We also utilized BAY11 on the NF2 VS cell line to understand the efficacy of NF-κB inhibition in NF2 VS. It was found to reduce proliferation and survival of the tumor cell line, although at approximately a 10-fold higher concentration, potentially due to the transformed nature of these cells as a robust and highly proliferative cell line.

We tested curcumin against VS cells due to our motivation to investigate clinically relevant inhibitors against VS. Curcumin is derived from turmeric, an Indian spice that has been described to have anti-inflammatory and anti-septic properties. More recently, curcumin has been established as an NF-κB inhibitor and has been tested in many clinical trials, including over 95 ongoing clinical trials currently (Hatcher et al., 2008). Marin et al. (2007) found that curcumin inhibits NF-κB activity and the expression of its downstream target genes, and also selectively induces apoptosis of melanoma cells but not normal melanocytes. This mechanism has been noted in several studies showing that curcumin acts by inhibiting TNFα-induced IκB degradation and therefore inhibits NF-κB activation (Hatcher et al., 2008). In our work, curcumin was found to be effective in reducing proliferation and survival in primary VS cells. Intriguingly, curcumin was more effective against the cell line at a lower dose than in VS or SCs, suggesting a higher therapeutic efficacy against NF2 VSs. The dosage curve of curcumin resembles a previously established dosage curve for HEI-193 cells (Angelo et al., 2011). Interestingly, Angelo et al. focused on another mechanism through which curcumin may be acting, Hsp70. Additionally, a follow up paper investigating curcumin's direct binding partners did not find NF-κB complex components as a target in HEI-193 cells (Angelo et al., 2013), although the authors did find inhibition of Protein Kinase B (AKT) phosphorylation in previous work (Angelo et al., 2011), an upstream regulator of NF-κB activation (Bai, Ueno & Vogt, 2009). This is in contrast to the large body of literature that shows curcumin's role as an NF-κB inhibitor, although many have also found additional curcumin targets (Marin et al, Hatcher et al., 2008). Similar to BAY11, it has been deemed a general inhibitor of inflammation.

Although curcumin has been found to be efficacious against colon cancer and Alzheimer's disease in animal and human studies, it is important to note that therapeutic and toxicity profiles of curcumin have not been comprehensively elucidated (Burgos-Moron et al., 2010). Although very high dosages of curcumin can be ingested safely, the amounts reaching the target cells are either very low (in nM range) or cannot be detected, potentially due to a change in curcumin's structure that hasn't been discovered. Burgos-Moron et al. outline some of the toxicity that has been noted in animal models with long term high dosage protocols leading to increased incidences of ulcers, hyperplasia, and inflammation of the cecum in rats. Some clinical trials have noted nausea and diarrhea in patients taking curcumin (Burgos-Moron et al., 2010). Formulations leading to higher absorption are currently under trial as curcumin is not readily absorbed in the body. We delivered curcumin dissolved in DMSO, increasing its solubility in media and ability to cross the cell membrane. Since the levels of curcumin that led to VS and SC death were comparable, it suggests that the drug may be toxic to healthy cells at those dosages, rather than specific to neoplastic cells. More research on curcumin's toxicity profile, best method for administration and its efficacy in brain diseases in needed before this drug may be applicable for VS patients.

To gain mechanistic insight in order to use these drugs most effectively, it would be important to explore whether the therapeutic efficacy of BAY11 and NF-κB against VS cells is solely due to NF-κB inhibition. Further, curcumin has recently been shown to have otoprotective effect against aminoglycoside toxicity (Salehi et al., 2014). If curcumin's otoprotective role against VS-induced SNHL is demonstrated, it would be beneficial to utilize it to attenuate both VS growth and associated SNHL.

Conclusion

In an attempt to find key modulators of VS growth by constructing the interactome of pathobiological pathways in VS, we identified pro-inflammatory transcription factor NF-κB. In this study, we established canonical NF-κB's aberrant activation. We also established pre-clinical efficacy of its inhibition using experimental and clinically relevant inhibitors that reduced growth and survival of primary VS cells and NF2 VS HEI-193 cells. Our results complement and augment previous findings of NF-κB modulating VS cell growth and survival. By establishing aberrance of several molecules involved in the NF-κB pathway and efficacy of NF-κB inhibition selectively in VS cells via several inhibitors, we expand on previous findings and reinforce NF-κB as a promising pharmacologic target against VS.

Example 3

Role of Cyclooxygenase 2 as a Modulator of Vestibular Schwannoma Growth

Motivated by previous findings that cyclooxygenase 2 (COX-2) expression correlates with VS growth rate (Hong et al., 2011), we investigated the role of COX-2 in VS. COX-2 was found to be aberrantly expressed in human VS and primary VS cells in comparison to nerve specimens and primary human SCs. Levels of COX-2's enzymatic product, prostaglandins, correlated with VS culture proliferation rate. Because COX-2 inhibitors, including salicylates such as aspirin, are frequently clinically used and are relatively well-tolerated, we explored their repurposing for VS. Primary VS cells were treated with three clinically used salicylates, namely aspirin, sodium salicylate (NaSal) and 5-aminosalicylic acid (5-ASA). All three treatments significantly reduced proliferation in primary VS cultures, with 5 mM aspirin, 1 mM NaSal and 5 mM 5-ASA reducing average proliferation to 19%, 18% and 55% of non-treated cells, respectively. These drugs did not lead to increased VS cell death nor affect healthy SCs. The cytostatic effect of aspirin in vitro was in concurrence with the retrospective finding that VS patients taking aspirin demonstrate significantly reduced tumor growth (Kandathil et al., 2014). Overall, this work suggests that COX-2 is a key modulator in VS cell proliferation and survival and highlights salicylates as promising pharmacotherapies against VS.

Introduction

Along with NF-κB, another major inflammatory mediator, cyclooxygenase 2 (COX-2), has been implicated in VS. The level of COX-2 in VSs, as judged by the intensity of COX-2 immunostaining in VS specimens, correlated with the tumors' proliferation rates (Hong et al., 2011). The COX enzymes catalyze biosynthesis of prostaglandins (PTGs), hormone-like lipid compounds that can trigger the inflammatory response (Sobolewski et al., 2010). In contrast to COX-1, which is expressed constitutively as a homeostatic enzyme in several cell types such as platelets and gastrointestinal mucosal cells, COX-2 is expressed at sites of inflammation and neoplasia (Hong et al., 2011; Sobolewski et al., 2010). Specifically, COX-2 has been described to modulate cell proliferation and apoptosis in many solid tumors, such as colorectal, breast, and prostate cancers (Sobolewski et al., 2010).

In this example, we have explored the aberrance of COX-2 in VS and therapeutic efficacy of salicylate-mediated COX-2 inhibition in primary VS cells. We found that COX-2 is aberrantly expressed in VS, as noted through COX-2 staining of VS and GAN specimens. Further, COX-2 was present at higher levels in VSs in comparison to healthy GANs, along with being present and active in VS-derived cultures. We tested the efficacy of COX-2 inhibition using salicylates. Salicylate, a class of drugs within non-steroidal anti-inflammatory drugs (NSAIDs) classified by its chemical structure, are attractive because they are clinically-relevant, well-tolerated and effective COX-2 inhibitors, commonly used against pathologies such as pain and arthritis (Hardman et al., 1996). Further, a chronic intake of salicylates led to a significant reduction in the incidence and decrease in burden of various tumors, such as colorectal cancer (Sobolewski et al., 2010). We explored the efficacy of three different salicylates against VS: aspirin, NaSal, and 5-ASA. These three salicylates, although acting through similar mechanisms to inhibit COX activity, have nuances that can lead to differential therapeutic and toxic profiles (Hardman et al., 1996). Further, the finding of each salicylate reinforces the findings of the other. We found that all salicylates tested were effective in selectively reducing proliferation of cultured VS cells, accompanied by reduced secreted PTG levels. Our work suggests promising potential of well-tolerated and commonly used salicylates against VS.

Methods

Reverse Transcription-quantitative Polymerase Chain Reaction (RT-qPCR)

The same methodology as described in Example 2 was utilized. qPCR was performed with TaqMan Primers and 6-FAM linked fluorescent probes (Applied Biosystems, CA) for PTGS2 (Hs00153133_m1) with reference gene ribosomal RNA 18s (Hs9999901_s1).

Immunohistochemistry of GAN and VS Specimens

The same methodology as described in Example 2 was utilized. Antibody against COX-2 was purchased from Abcam (ab15191).

Protein Extraction and Western Blot

The same methodology as described in Example 2 was utilized. Antibody against COX-2 was purchased from Abcam (ab15191).

Primary VS and SC Culture

The same methodology as described in Example 1 was utilized. Cultures were treated approximately after 2 weeks of culturing.

Prostaglandin E2 Assay

Prostaglandin (PTG) E2 was assayed in the media of VS cultures using the Prostaglandin E2 Parameter Assay Kit (R&D Systems, KGE004B). The media was collected after 48 hours of treatment from non-treated and treated cultured cells. Manufacturer's instructions were closely followed.

Drug Preparation and Treatment

Primary VS and SC cultures were treated with aspirin (sc-202471), NaSal (sc-3520) and 5-ASA (sc-202890) purchased from Santa Cruz Biotechnology. 1 mM and 5 mM aspirin, 1 mM, 5 mM and 10 mM NaSal, and 1 mM and 5 mM 5-ASA were prepared by mixing appropriate amount of drug (powder form) into pre-warmed culture media. The cultures were incubated with the drugs for 48 hours. To label proliferating cells, BrdU was added 20 hours before fixation. pH was measured in the media after drug addition to ensure no significant deviations.

Proliferation and Apoptosis Assay

After 48 hours of treatment with salicylates, primary VS and SC cultures were fixed for BrdU staining, to visualize proliferation, or TUNEL staining, to visualize cell death. The same methodology as described in Example 1 was utilized.

Statistical Analyses

Two-tailed t-test was used to compare differences in qPCR and western blot analyses. Spearman's correlation was used to assess the relationship between PTG levels and culture growth. Paired two-tailed t-test was used to compare differences in proliferation and cell death after treatment with salicylates. P-values for multiple comparisons were adjusted using the Benjamini-Hochberg adjustment for false discovery rate. P-values less than 0.05 were considered significant.

Results

Figure 9:
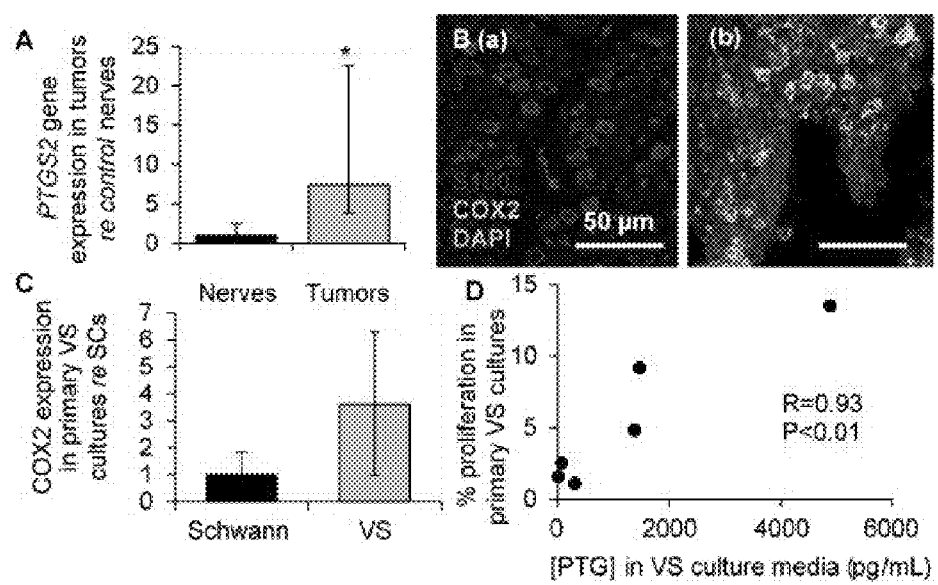
FIG. 9 is a bar graph demonstrating that COX-2 is aberrantly upregulated in VS and derived primary cultures. A. COX-2 expression in human VS (n=9) versus great auricular nerve (GAN, n=8) as measured through qPCR. *p<0.05. Error bars represent range. B. Representative images of COX2 expression (light grey), as visualized through immunohistochemistry, in GAN (n=5 different nerves, a) and VS (n=6 different VSs, b) specimens. COX-2 is localized to the cytoplasm of cells in VS and is not detected in healthy GAN. Schwann or schwannoma cells are labeled with S100 (dark grey) and nuclei are labeled with DAPI. C. COX-2 expression in cultured human VS (n=6 different cultures) normalized to expression in Schwann cell cultures (n=6 different cultures) as quantified through western blot analysis. Error bars represent SD. D. Correlation of PTG concentrations secreted in VS culture media with VS proliferation rate (% BrdU-positive cells) in vitro. R represents Spearman's correlation coefficient (n=6).

Cyclooxygenase 2 is Aberrantly Expressed and Active in VS and its Derived Cultures COX-2, an enzyme responsible for prostaglandin (PTG) synthesis, is encoded by the PTGS2 gene. PTGS2 was found to be 7.4-fold higher (range of 3.7 to 15.1, p=0.04) in human VS (n=9) in comparison to healthy great auricular nerves (GAN, n=8), as measured through qPCR on extracted RNA from fresh human VS and GAN tissue (FIG. 9A). Further, through immunohistochemistry, COX-2 staining could be noted in most of the cytoplasmic and perinuclear regions of VS cells in 4 out of 6 specimens, with 2 having a smaller COX-2 positive cell population (FIG. 9B (a)). COX-2 was minimally detectable in 2 out of 5 healthy GAN specimens: although the SCs were S100-positive as they wrapped around nerve fibers of GANs, only a few (approximately 4-5 cells per frame) COX-2-positive cells were detected (FIG. 9B(b)).

On the protein level, COX-2 was present at substantially higher levels in cultured VS cells in comparison to SCs. Expressed as mean±SD, COX-2 expression was found to be 3.6±2.7-fold higher in cultured human VS (n=6) versus SCs derived from GAN (n=6) as quantified through western blot analysis (p=0.06, FIG. 9C). To understand COX-2's role in VS, we explored correlation of PTGs levels in culture media with VS cultures' growth rates, as quantified by the percentage of BrdU-positive cells in the culture. VS cultures secreted PTGs at varied levels, with an average of 1351 pg/mL and a range of 12-4880 pg/mL, and the PTG concentrations in media strongly correlated (R=0.93, p=0.007) with VS proliferation rate in vitro (n=6, FIG. 9D).

Salicylates Reduce Proliferation of Cultured VS Cells

To assess the therapeutic efficacy of COX-2 inhibition, we utilized three clinically-relevant and well-tolerated salicylates: aspirin, NaSal and 5-ASA. We found that these inhibitors, at physiologically relevant concentrations, selectively reduce VS cell proliferation. Representative images of non-treated (NT), 5 mM aspirin and 1 mM NaSal treated cells are shown in FIG. 10A (a-c), respectively. Data are summarized as average±standard error of mean (SEM). Benjamini-Hochberg adjusted p-values are provided. Proliferation is normalized to the NT cells for each culture. After 1 and 5 mM aspirin treatment, proliferation changed in VS cells to 129.6±26.2% (n=3 different cultures, p=0.44) and 19.3±5.5% (n=5 different cultures, p=0.0002, FIG. 10A (b)), respectively, of the NT cells (FIG. 10A (a), having a SEM of 42.3%) (FIG. 10B). After 1, 5 and 10 mM NaSal treatment, VS cell proliferation changed to 18.9±5.0% (n=3 different cultures, p=0.01), 25.4±11.1% (n=7 different cultures, p=0.0009) and 20.6±11.2% (n=6 different cultures, p=0.003), respectively, of the NT cells (having a SEM of 33.4%) (FIG. 10B). After 5 and 10 mM 5-ASA treatment, VS proliferation changed to 66.0±15.1% (n=6 different cultures, p=0.15) and 54.8±16.5% (n=6 different cultures, p=0.05), respectively, of the NT cells (having a SEM of 36.3%) (FIG. 10B). Going from most effective to least effective based on dosage, NaSal, aspirin and 5-ASA were all effective in reducing proliferation in VS cells.

Salicylates at these concentrations did not induce significant cell death in VS cells (FIG. 10C (a)-(c)). After treatment with 1 and 5 mM aspirin, the cell death rate did not change, going from 0.8±0.4% in the NT cells to 0.6±0.3% (n=6 different cultures, p=0.32) and 2.8±2.2% (n=5 different cultures, p=0.38, FIG. 10C (b)), respectively (FIG. 10D). The cell death rate did not change for 5 mM NaSal and 5-ASA treated cells, going from 1.0±0.5% in the NT cultured VS cells to 3.3±2.3% (p=0.21, FIG. 10C (c)) and 5.6±3.2% (p=0.19), respectively (n=5, FIG. 10D). Additionally, we measured levels of PTGs in VS to assess COX-2 inhibition. Treatment with 5 mM aspirin, 1 mM and 5 mM NaSal reduced secreted PTG levels to 3.1% (n=4 different cultures, p=0.000002), 3.8% (n=4 different cultures, p=0.000005) and 32.2% (n=3 different cultures, p=0.07) of NT cells, respectively (FIG. 10E). Our results suggest that COX-2 was inhibited in these cultures.

Salicylates do not Reduce Proliferation of SCs

The salicylates' cytostatic effect against VS cells seemed to be specific to the neoplastic cells since treating healthy SCs with the same concentrations of the drug did not lead to a decrease in cell proliferation. After aspirin treatment, proliferation did not change in SCs, going to 124.4±72.9% (p=0.48) and 198.1±141.3% (p=0.47) of the NT cells with 1 and 5 mM aspirin, respectively (n=3 different cultures, FIG. 10F). After NaSal treatment, proliferation was not affected until the highest dose of 10 mM NaSal. Proliferation rate was now 104.4±13.2% (n=3, p=0.45) and 64.9±18.9% (n=4, p=0.03) of the NT cells with 5 and 10 mM NaSal, respectively (FIG. 10F). After 5-ASA treatment, proliferation did not change in SCs, being 107.8±22.4% (p=0.51) and 109.7±26.7% (p=0.54) of the NT cells with 5 and 10 mM 5-ASA, respectively (n=3, FIG. 10F). These results suggest the promising utility of salicylates to specifically and effectively minimize VS growth.

Discussion

We have shown that well-tolerated and clinically common salicylates led to selective decrease in proliferation and in secreted PTG levels in primary VS cultures. Our findings in vitro parallel our findings of a retrospective study in which we correlated the growth rates of human VSs, calculated using tumor size in serial MRI scans, with the patient's aspirin intake (for unrelated medical diagnoses to VS)

(Kandathil et al., 2014). We found that the probability of VS growth in patients who take aspirin is approximately half in comparison to VS patients who were not taking aspirin (Kandathil et al., 2014). Interestingly, many VS patients were taking a low-dose aspirin for co-morbidities listed in their medical records. Although a low-dose aspirin may not reach the concentration in sera that we found therapeutic in our work (1-5 mM), salicylates, being organic acids, tend to have a high affinity towards sites of inflammation, potentially explaining their efficacy at low dosages (Hardman and Limbird, 1996). Other clinical studies have shown a protective and therapeutic effect of a low dose aspirin against different types of cancers (Elwood et al., 2009). Nonetheless, the therapeutic range of salicylates detected in the sera of patients ranges from approximately 0.3-2 mM (Hardman and Limbird, 1996), comparable to dosages we found efficacious in vitro. Due to the simplified nature of a culture model, it is difficult to directly translate the concentration effective on cultured tumor cells with the concentration required in vivo in order to be efficacious against VS when salicylates are administered systemically. To gain some insight into whether these concentrations would be feasible in vivo, we applied salicylates onto healthy SCs. We did not find a decrease in SC proliferation with salicylates, suggesting the dosages to be tolerable to SCs. Additionally, salicylates readily cross the blood-brain barrier and can reach up to 50% of the concentration present in the blood (Bannwarth et al., 1989), an appealing aspect that makes translation of salicylates against VS even more promising.

The significant correlation of PTG levels with VS culture proliferation rate is in line with previous literature that COX-2 expression correlated with VS growth rate (Hong et al., 2011). Further, substantially decreased PTG levels in the media after salicylates treatment suggests that the salicylates led to COX-2 inhibition. It was interesting that the salicylate effect was limited to only a decrease in proliferation and did not affect cell survival. Although salicylates can lead to both a decrease in growth and survival in neoplastic cells, most studies implicate salicylate-mediated cell death to mechanisms other than COX-2 inhibition (Chan et al., 1998). In our case, it could be that salicylates have a different therapeutic window for apoptotic effects than for anti-proliferative effects in VS cells, although higher salicylate concentrations were not tested since they would be above the range considered safe in vivo.

It is feasible that the salicylates could be acting through other molecular pathways along with COX-2 inhibition to lead to VS cytostaticity as salicylates do have multiple targets. For instance, although COX-2 is a preferential target for salicylates compared to COX-1 (Sobolweski et al., 2010), it is possible that COX-1 is also inhibited in VS cells as COX-1 expression and activity was not assessed in this study. Further, aspirin and NaSal can also inhibit NF-κB directly, through blockade of TκK especially at higher dosages (≥5 mM) (Kopp and Ghosh, 1996; Kaiser et al., 1999; Yin et al., 1998). This might be the case for aspirin in our work, as we do not note decreased proliferation at 1 mM aspirin, although PTG secretion is inhibited significantly. Interestingly, the COX-2 gene promoter does have a κB binding site (Sobolweski et al., 2010) and it could be that NSAID-mediated NF-κB-mediated cell death is ultimately due to a decrease in COX-2 expression.

Although COX-2 inhibition does not seem to lead to significant side effects, COX-1 inhibition can lead to interference with homeostatic functions, including increased incidence of gastrointestinal hemorrhage and ulceration with chronic intake (Sobolweski et al., 2010). Among the salicylates tested, aspirin is a more potent drug as it leads to an irreversible inhibition of COX-2 by acetylating its binding site in comparison to NaSal and 5-ASA that bind COX-2 through reversible competitive binding (Hardman et al., 1996; Sobolewski et al., 2010). We have also tested NaSal and 5-ASA as they can serve as alternatives to aspirin for people with hypersensitivity to aspirin. Our results also motivate trials of COX-2-selective inhibitors such as celecoxib against VS as these compounds further curb the side effects of general COX inhibitors (Solobweski et al., 2010).

Taken together, our pre-clinical data motivate future work studying the mechanisms behind the therapeutic efficacy of salicylates against VS cells and clinical translation of these drugs against VS.

Conclusion

In this example, we established the aberrance of COX-2 in VS and VS cultures. The secreted levels of its enzymatic product, PTGs, correlated with VS culture proliferation rates. Additionally, we found clinically well-tolerated COX-2 inhibitors, namely aspirin, NaSal and 5-ASA to minimize proliferation of VS cells, without affecting healthy SCs. Our in vitro findings were further reinforced with our clinical findings that the probability of VS growth decreased to approximately half in patients taking aspirin. These drugs, thus far to our knowledge, would be the most promising treatments against sporadic VS as they are commonly used for other pathologies including other tumors such as colon cancer, with minimal side effects when utilized within the clinically well-established therapeutic range.

Example 4

Cross-talk Between Hepatocyte Growth Factor and Vascular Endothelial Growth Factor in Schwann and Schwannoma Cells Although several pathways have been independently implicated in VS pathobiology, interactions among these pathways have not been explored. This work explored potential cross-talk between two angiogenic molecules previously implicated in VS, namely hepatocyte growth factor (HGF) and vascular endothelial growth factor-A (VEGF-A) in VS, an interaction that has been described in other physiological and pathological cell types. We affirmed previous findings that VEGF-A and HGF signaling is aberrantly upregulated in VS. It was found that VEGF-A and HGF signaling pathways modulate each other in primary human VS and SC cultures. siRNAs targeting cMET decreased both VEGF-A and its receptor, VEGFR2 protein levels, and siRNAs targeting VEGF-A reduced cMET expression. Additionally, siRNA-mediated knockdown of VEGF-A or cMET and pharmacologic inhibition of cMET led to decreased proliferation in primary VS cultures. Our data suggests cross-talk between these two prominent pathways in VS and highlights HGF/cMET pathway as an additional important therapeutic target against VS.

Introduction

Although several pathways have been implicated in VS pathobiology, interactions among these pathways have been scarcely established. Levels of vascular endothelial growth factor-A (VEGF-A), a prominent mitogenic and angiogenic factor, and its receptor tyrosine kinase VEGFR-1 correlate with VS growth rate (Møller et al., 2010). Administering bevacizumab, a humanized VEGF-A antibody, to patients with NF2-associated VS leads to a volumetric decrease in 55% of the VSs (Plotkin et al., 2009; 2012). As investigators continue to establish the many interactors of VEGF-A, it is interesting to explore VEGF-A's potential to regulate and be regulated by other molecules that could be driving VS growth, providing us new therapeutic targets and the ability to overcome potential drug resistance inevitable with monotherapies. HGF, a potent angiogenic factor, and its receptor tyrosine kinase cMET have been implicated in several other cancers (Gheradi et al., 2012) and VS (Moriyama et al., 1998a), though they have not been explored as therapeutic targets in VS previously. We investigated cross-talk between VEGF-A and HGF, an interaction that has been established in a few other cell types. HGF/cMET signaling pathway has been shown to interact closely with VEGF-A signaling pathway in other physiological signaling, such as in endothelial cells (Sulpice et al., 2009), and pathological signaling, such as in adenocarcinoma (Matsumura et al., 2013) and glioma cells (Moriyama et al., 1998b), contexts. Specifically, in endothelial cells, VEGF-A and HGF synergistically activated mitogen-activated protein kinases (MAPKs), stimulation with VEGF-A increased cMET levels, and stimulation with HGF elevated VEGFR2 levels (Sulpice et al., 2009). Exploring this cross-talk between VEGF-A and cMET in VS cells can provide insight into mechanism for VEGF-A-mediated tumor growth and additional targets for therapeutics in the future.

We found that HGF signaling, along with VEGF-A signaling, is significantly upregulated in VS, as measured through mRNA and secreted protein levels. In both primary human VS and SC cultures, we found that VEGF-A and cMET signaling pathways modulate each other. In VS cultures, siRNAs targeting cMET decreased VEGF-A and VEGFR2 protein levels, and targeting VEGF-A reduced cMET expression. Additionally, siRNA-mediated knockdown of VEGF-A or cMET, and pharmacologic inhibition of cMET led to decreased proliferation in primary VS cultures.

In this example, by investigating the cross-talk between VEGF-A and cMET pathways in VS, we provide greater insight into the VS interactome, providing potential mechanistic insight into bevacizumab's efficacy against VS and establishing cMET as an additional therapeutic target.

Methods

Real Time-Quantitative Polymerase Chain Reaction (RT-qPCR)

The same methodology as described in Example 2 was utilized. qPCR was performed with TaqMan Primers and 6-FAM linked fluorescent probes (Applied Biosystems, CA) with probes (Applied Biosystems, CA) for VEGFA (Hs00900055_m1), HGF (Hs00300159_m1), VEGFR2 (Hs00911700_m1) and MET (Hs01565582_g1). The reference gene was ribosomal RNA 18s (Hs9999901_s1).

Cytokine Array

VS and GAN secretions were collected by incubating fresh, washed tissue in PBS for 1 hour at 37° C. with 5% $CO_2$ levels. Human cytokine array membranes (RayBio Human Cytokine Antibody Array, RayBiotech, Inc.) were probed with 21 VS secretion samples, 7 GAN samples and 1 blank sterile PBS. Manufacturer's protocol was followed in conducting the experiment and data analysis. Samples were dialyzed twice with PBS. The membranes were exposed to the blocking buffer at room temperature (RT) for 1 hour, incubated with sample at 4° C. overnight, washed with Wash Buffer I and II at room temperature (RT), incubated with biotin-conjugated antibodies at 4° C. overnight, washed and incubated with HRP-conjugated streptavidin at RT for 1 hour. The membranes were then exposed in Chemidoc (BioRad Laboratories, Hercules, Calif.). The relative expression levels of HGF and VEGF-A were compared after densitometry analysis using Quantity One (Bio-Rad Laboratories, Hercules, Calif.).

Primary VS and SC Culture

The same methodology as described in Example 1 was utilized. Cultures were treated with siRNAs approximately after 2 weeks of culturing.

siRNA and Pharmacologic Treatment

To understand cross-talk between HGF and VEGF-A pathway, cultured VS cells were incubated with Life Technologies silencer select siRNAs targeting VEGFA (s461) or MET (s8700). To understand whether HGF signaling contributed to VS proliferation, cultured VS cells were treated with MET inhibitor SU11274 (Sigma-Aldrich, MO, #S9820). Seventy-two hours after siRNA treatment or 12 hours after treatment with SU11274 (2 µM), cells were incubated with 10 µg/mL BrdU (Life Technologies, NY, # B23151) for 20 hours before fixation. The same methodology for proliferation assay as described in Example 1 was utilized.

Protein Extraction and Western Blot

Expression and activation of the VEGF-A, VEGFR2 and cMET was investigated through western blot analysis. The same methodology as described in Example 2 was utilized. The membrane was probed with Santa Cruz antibodies against VEGF-A (#sc-152) and cMET (#sc-161) and Cell Signaling antibody against phosphorylated (P-)-cMET (#3077). Antibody against 3-actin (Cell Signaling, MA, #4970) served as an internal control. Band densities were normalized to 3-actin for a given lane.

Statistical Analyses

Statistical significance was determined using the two-tailed t-test for qPCR and western blot analyses after a Benjamini-Hochberg adjustment for multiple hypotheses. Statistical significance for cytokine array differences was determined using ANOVA test with alpha set to 0.05. Paired two-tailed t-test was used to compare differences in proliferation after treatment. P-values less than 0.05 were considered significant.

Results

Increased Expression and Activation of cMET and VEGF-A Signaling in VS

Figure 11:
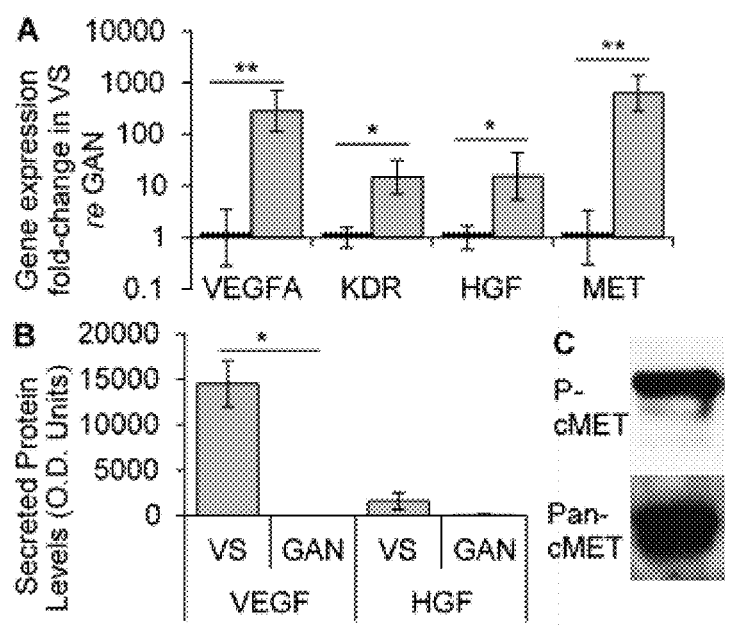

To investigate aberrant expression of HGF and VEGF-A signaling pathways in VSs, gene expression differences in HGF, VEGF-A, cMET, and VEGFR2 (gene KDR) were determined in human VSs in comparison to healthy GANs. Tumor specimens (n=8 different specimens) had significantly elevated expression compared to GANs (n=7 different specimens), being 286.7-fold (p=0.003) and 15.0-fold (p=0.011) higher with a standard error range of 116.6-705.4 and 7.1-31.6 for VEGFA and KDR, respectively (FIG. 11A). GANs had a range of 0.3-3.5 and 0.6-1.6 for VEGFA and KDR, respectively. Genes HGF and its receptor MET were also significantly upregulated, being 15.4-fold (p=0.043) and 632.0-fold (p=0.001) with a range of 5.4-43.7 and 286.0-1391.9, respectively. GANs had a standard error range of 0.6-1.7 and 0.3-3.4 for HGF and MET, respectively (FIG. 11A).

We sought to determine if VEGF-A or HGF secretion levels were higher in VSs versus healthy nerves. Measuring HGF and VEGF-A levels using a cytokine array, we found VEGF-A to be selectively secreted from VSs (n=21 different tumors), with an average optical density (O.D.) value of 14,558±SEM of 2,527, with no detectable VEGF-A in GAN secretions (n=7 different nerves) (FIG. 11B). This differential level of secretion was highly significant (p=0.003). HGF tended to be secreted at higher levels in VSs, with an O.D.

value of 1,615±885, than GANs, with an O.D. value of 87±87, although the trend did not meet significance (p=0.334, FIG. 11B).

To understand if cMET is activated in sporadic VSs, we investigated the phosphorylation status of c-MET. Five different sporadic VS tumors consistently demonstrated phosphorylated cMET (FIG. 11C).

Cross-talk Between cMET and VEGF-A Signaling Pathways in Primary SCs

Figure 12:
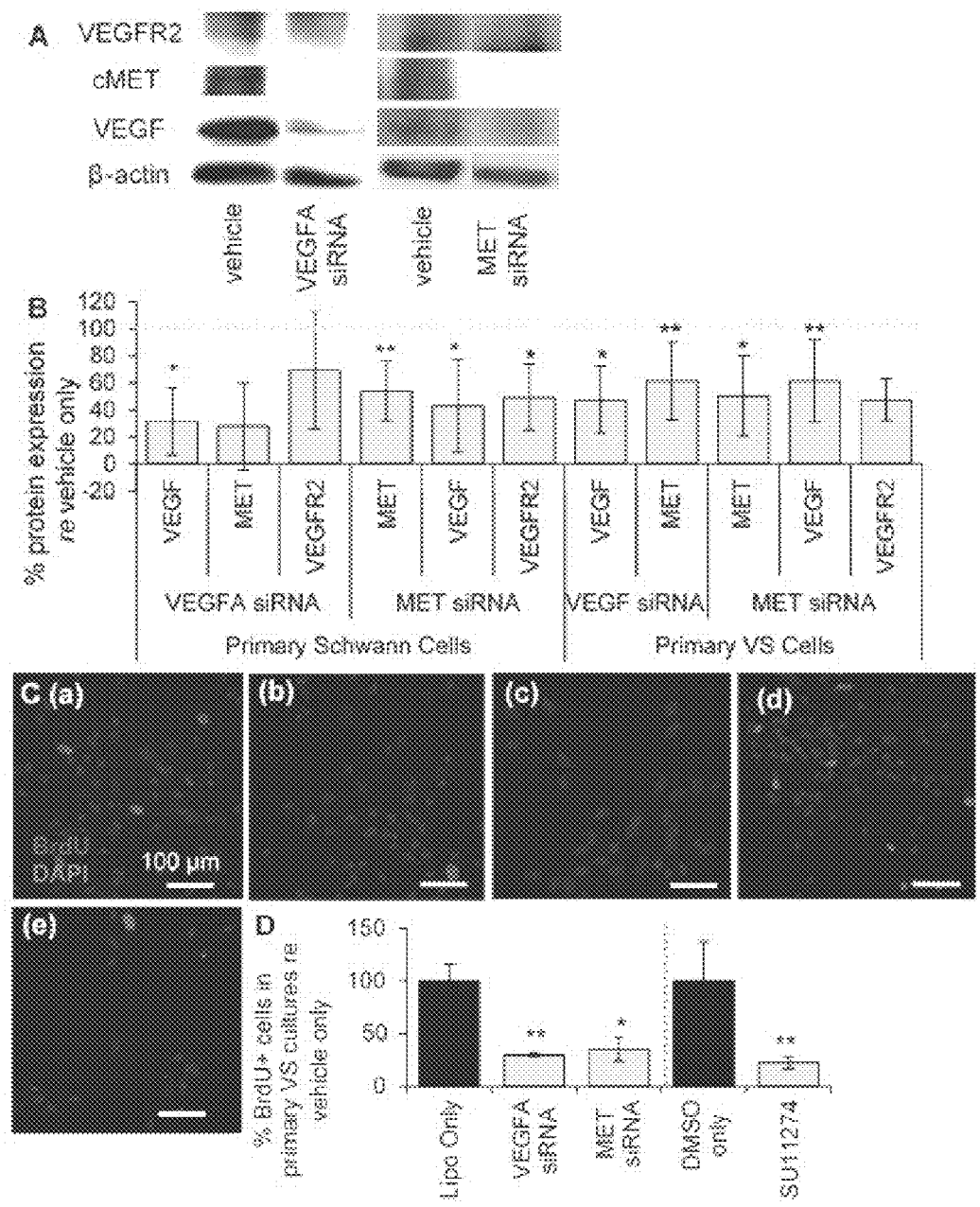
FIG. 12 is a collection of images and graphs that demonstrate the interactions of the VEGF-A and cMET pathways at the molecular level. A. Representative image of western blot showing expression of VEGFR2, cMET and VEGF-A for vehicle only and for siRNAs targeting VEGF and MET genes in primary SCs. B. Protein expression of VEGF, MET and VEGFR2 after VEGF and MET siRNA treatment of cultured SCs (n=2-4 different cultures) and VS cells (n=5 different cultures) quantified through western blot analysis. All levels are normalized to vehicle only protein expression, being 100% (dashed line). *p<0.05 **p<0.01. Error bars represent SEM. C. Representative proliferation images are shown for (a) vehicle only, (b) VEGF, (c) cMET siRNA, (d) DMSO only, (e) SU11274-treated primary VS cells. BrdU in nuclei (light grey) marks proliferating cells, nuclei are labeled with DAPI. Scale bar=100 µm for all images. D. Quantification of proliferation changes after siRNA (n=5 different cultures) and after SU11274 (n=4 different cultures) treatment of primary VS cells normalized to proliferation in control non-treated cells. *p<0.05, p<0.01. re=in comparison to. Error bars represent SEM

Previous studies in endothelial cells identified possible cell signaling crosstalk between the VEGF-A and HGF receptor signaling pathways (Sulpice et al., 2009; Matusumura et al., 2013). We have investigated this cross-talk in normal SCs with siRNAs targeting the VEGF-A and HGF signaling pathways. Comparing protein expression in SCs from the same culture treated with vehicle only, siRNAs were capable of knocking down VEGF-A and cMET to a significant extent, with 32±25% (n=4 different cultures, p=0.04) and 54±22% (n=5 different cultures, p=0.003) knockdown achieved, respectively (FIGS. 12A, 12B). Importantly, MET knockdown decreased VEGF-A levels in normal SCs significantly, reducing the protein levels to 43±34% of vehicle only-treated cells (p=0.02, n=4 different cultures, FIGS. 12A, 12B). MET knockdown also decreased VEGFR2 levels, reducing the protein levels to 50±24% (n=3 different cultures, FIGS. 12A, 12B) of vehicle only-treated cells, although this trend did not meet significance (p=0.07).

VEGF-A knockdown did not lead to a significant decrease in MET levels, being 28±32% of vehicle only controls (n=2 different cultures, p=0.19), or of VEGFR2 levels, being 70±43% with VEGF-A siRNA treatment of vehicle only controls (n=3 different cultures, p=0.35) (FIGS. 12A, 12B). Although VEGFR2 level changes were not consistent between experiments with VEGF-A siRNA leading to a large variability, MET levels were consistently decreased in the two experiments. More experiments with VEGF-A siRNA in SCs will be helpful in establishing the protein expression changes with confidence.

Cross-talk Between cMET and VEGF-A Signaling Pathways in Primary VS Cells

Knockdown of MET also led to decreased VEGF-A and VEGFR2 in primary VS cultures as noted in SCs. Comparing protein expression in VS cells from the same culture treated with vehicle only, siRNAs were capable of knocking down VEGF-A and cMET to a significant extent, with 48±25% (n=5 different cultures, p=0.009) and 51±30% (n=6, p=0.005) knockdown achieved, respectively (FIG. 12B). cMET knockdown led to a decrease in VEGF-A and VEGFR2 levels, with reduction to 62±31% (p=0.03) and 48±16% respectively (n=5 different cultures, p=0.007, FIG. 12B). VEGF-A knockdown did cause a significant decrease in cMET expression in VS cells, reducing cMET levels to 62±29% of the controls (p=0.04, FIG. 12B).

Decreased VS Cell Proliferation with Molecular VEGF-A and MET or Pharmacologic MET Inhibition To understand the implications of silencing VEGF-A and cMET in VS cells, cell proliferation studies were performed in primary VS cells. Basal cell proliferation for VS cells treated with vehicle only was 5.24% on average, with a range of 2.2 to 7.0% (FIG. 12C (a)). Silencing VEGF-A or MET reduced VS cell proliferation to 29.7±1.8% (SEM) (n=5 different cultures, p<0.01, FIGS. 12C (b), 12D) and 34.8±11.4% (n=5 different cultures, p=0.02, FIGS. 12C (c), 12D) of control. Similarly, specific inhibition of cMET signaling with the 2 µM MET inhibitor SU11274 reduced proliferation to 22.4±11.7% (FIGS. 12C(e), 12D) of VS cells treated with DMSO only (9.1±3.4%) (n=4 different cultures, p<0.01, FIG. 12C (d)).

Discussion

To gain a deeper understanding of the VS pathobiological interactome, we have focused on investigating the relationship between the HGF and VEGF-A signaling pathways. Our work establishes abnormal upregulation and activation of the HGF pathway in VS pathobiology as we found drastically higher levels of HGF and cMET being transcribed in comparison to healthy nerves, activated phosphorylated cMET in all tumors tested and relatively higher levels of secreted HGF. Our findings further expand on previous work showing that HGF and cMET are present in VSs based on immunohistochemical staining of human VS specimens (Moriyama et al., 1998a). Importantly, we found that siRNA-mediated cMET silencing or pharmacological inhibition of cMET led to significantly decreased primary VS cell proliferation, demonstrating cMET as a novel therapeutic target. Targeting of cMET and HGF may provide an alternate or adjuvant therapy to other pharmacological approaches being investigated to modulate VS growth.

In this work, we also affirmed aberrant VEGF-A signaling as VEGF-A and VEGFR2 were expressed at significantly higher levels in VS and VEGF-A was secreted at significant higher, albeit variable, levels in VS in comparison to healthy nerves. We also confirmed VEGF-A's role in VS growth as siRNA-mediated VEGF-A silencing inhibited primary VS cell proliferation. This is in agreement with previous work showing the therapeutic efficacy of bevacizumab in NF2 VS patients (Plotkin et al., 2012) and in cranial NF2 HEI-193 xenografts in mice (Wong et al., 2010). We also show efficacy of anti-VEGF-A therapy against sporadic VS cells.

Along with exploring VEGF-A and cMET's role in VS separately, we explored cross-talk between these two pathways. Previous exploration of the cross-talk in other cell types (Sulpice et al., 2009; Moriyama et al., 1998b) focused on changes due to elevation of either HGF or VEGF-A in cultures. With a focus on devising therapies and therefore reducing functional HGF or VEGF-A signaling, we designed our study to silence cMET or VEGF-A and note the effect on the other. VEGF-A and cMET have a direct regulatory relationship, rather than inverse, in VS and SCs. The trends discovered in VS and SC cultures are in line with previous studies in other cell types. Further, since decreases in VEGFR2 after VEGF siRNA treatment were not observed in SCs, it suggests that siRNA targeting is specific.

The stage of VEGF and cMET cross-regulation seems to be at the transcriptional level, where VEGF-A and HGF signaling regulates downstream gene expression ultimately leading to modulation of the other pathway. Sulpice et al. (2009) demonstrated that, both VEGF-A and HGF slightly increased the MET and VEGFR2 mRNA levels, respectively, in endothelial cells. Moriyama et al. (1998b) also found a similar pattern where treatment of the glioma cells with HGF lead to increased secretion of VEGF proteins accompanying increased transcription of VEGF mRNA in a dose-dependent fashion. This relationship could be confirmed in future work by measuring VEGFR2 and MET mRNA levels after HGF and VEGF-A siRNA treatment in SC and VS cultures.

We also found that MET siRNA led to decrease in VEGFR2 levels in both primary SCs and VS cells, a correlation that has not been published for any cell type thus far. This is intriguing because the HGF/cMET signaling, through its regulation of protein kinase B, p38 and other kinases downstream, could regulate several transcription factors that could in turn regulate many genes including VEGFA and VEGFR2 (Moriyama et al., 1998; Sulpice et al., 2009). This could explain, at least partially, how neoplastic cells sustain growth and survival in an autocrine manner.

The cross-talk between VEGF and HGF pathways in VS is fascinating as it suggests that decreasing VEGF-A levels, for example through the use of bevacizumab, could modulate cMET levels. VEGF-A has been known to cross-talk with several other biological molecules, such as fibroblast growth factor 2 (Tokuda et al., 2008). VEGF-A inhibition may also affect several of these pathways in VS cells, with the cumulative effect of relatively high therapeutic efficacy of anti-VEGF therapy against VS, as seen with the clinical use of bevacizumab. It would be interesting to assess large scale protein and gene expression changes in VS after bevacizumab treatment to understand its effect on the entire VS pathobiological interactome.

Our work may also be relevant towards understanding drug resistance. Resistance against bevacizumab, yet to be explored after long term use in VS, has been noted in other tumors and cancers (Lieu et al., 2013). A potential mechanism of resistance could be loss of HGF/cMET regulation by VEGF-A, therefore leading to uncontrolled HGF-regulated growth, although VEGF-A is inhibited (McCarty 2013). In this scenario, it would be efficacious to utilize a cMET inhibitor to overcome this resistance.

Conclusion

We discovered cross-talk between upregulated and activated angiogenic pathways in VS, namely the VEGF-A and HGF pathways. Specifically, we found that siRNA-mediated knockdown of VEGFA led to a decrease in cMET expression, and knockdown of cMET lead to a decrease in VEGF-A and VEGFR2 levels in SCs and VS cells. Our findings are in line with previous work that outlines these interactions in other cell types, such as endothelial cells. Our work, through establishing cross-talk between VEGF-A and cMET, two molecules typically studied independently in VS, can provide new ways to understand and manipulate VS pathobiology with design of more effective pharmacotherapies, including combination therapies targets VEGF-A and cMET.

Example 5

The Potential Otoprotective Role of Fibroblast Growth Factor 2 in Hearing Loss Due to Vestibular Schwannomas Since the recognition that sensorineural hearing loss (SNHL) associated with vestibular schwannomas (VSs) is not solely due to auditory nerve compression, elucidating the mechanism by which VSs cause SNHL has been an important task. We hypothesize that the severity of SNHL associated with sporadic VSs is correlated with tumor secretion of proteins with ototoxic or otoprotective potential. Secretions were collected from fresh surgical specimens of sporadic VS, divided into groups associated with good hearing (GH, word recognition >70% and pure-tone average <=30 dB) or poor hearing (PH). Secretions were analyzed on a cytokine array. Of the 37 molecules studied, 9 were significantly expressed in VS secretions versus control nerves. VS-secreted fibroblast growth factor 2 (FGF2) levels were inversely correlated with the degree of SNHL. Further, FGF2 applied onto murine cochlear explant cultures treated with ototoxic gentamicin was able to prevent neurite loss, demonstrating its otoprotective effect. This work highlights known otoprotective FGF2 as a potential tumor-secreted mediator of hearing protection in VS.

Introduction

The pathobiology of SNHL due to VSs remains elusive. The poor correlation between degree of SNHL and VS radiological dimensions or intracanicular extent suggest that nerve compression is not the only cause of SNHL due to VS (Nadol et al., 1996; Cayé-Thomasen et al., 2007). Tumor presence does, however, lead to cochlear degeneration and neuronal loss in patients with VS (Roosli et al., 2012). Stankovic et al. (2009) demonstrated that VS stratified by hearing have different genetic expression profiles, suggesting that differential expression of potentially ototoxic or otoprotective molecules may contribute to the SNHL associated with VS. We now focus on tumor-secreted factors that may modulate hearing in patients with VS.

We have focused on cytokines—small, secreted cell signaling molecules-because they are thought to mediate SNHL in a variety of diseases, including meningitis, cochlear otosclerosis and labyrinthitis (Adams, 2002; Satoh et al., 2003; Lobo et al., 2013). Specifically, inhibition of pro-inflammatory cytokines through molecules such as interleukin-1 receptor antagonist (IL1RN) and anti-TNFα antibodies has been proposed as potential treatments against presbycusis and other types of SNHL (Rynne et al., 2006; Goldbach-Mansky et al., 2006, Lobo et al., 2013). Additionally, corticosteroids, drugs that are known to repress cytokine gene transcription, are known to be effective in many cases of sudden SNHL associated with VS, suggesting a biochemical imbalance or inflammatory response as a potential trigger for loss of hearing (Lebel & Freij, 1988; Barnes & Adcock, 1993; Chen, Halpin & Rauch, 2003).

In addition to cytokines, we studied expression of several non-secreted molecules in incubated medium from VS because tumors are known to shed (Black, 1980; Steffensen et al., 2008). For example, shedding plasma membrane fragments may have proteins attached, including receptors, which can contribute to intercellular signaling (Taylor & Black, 1986). We also studied several candidate molecules identified in our recent proteomic analysis of perilymph from patients with VS (Lysaght et al., 2011). We investigated a total of 37 proteins using a customized cytokine array and found that VS-secreted fibroblast growth factor 2 (FGF2) levels inversely correlate with degree of SNHL in VS patients. Differential expression was validated with enzyme-linked immunosorbent assay (ELISA). Given FGF2's otoprotective role in other contexts, our results point to FGF2 as a secreted molecule (Zhai et al., 2004) that may contribute to hearing protection in some patients with VS (Low et al., 1996; Sorensen, Nilsen & Wiedlocha, 2006). Additionally, by assessing FGF2's otoprotective capability in murine postnatal organotypic cochlear explant cultures, we attempted to establish the first animal model to study VS-associated SNHL. Using this model, we can causatively explore the potential of VS secreted factors to lead to cochlear cell damage and loss.

In this example, through the use of a cytokine array, we investigated presence of cytokines in VS and their correlation with SNHL due to VS. Further, after identifying FGF2 in VS, its otoprotective role was tested via a cochlear explant culture model.

Methods

Study Population and Specimen Collection

Surgical VS specimens were collected from a total of 16 adults with good hearing (GH, having a pure tone average <30 dB and word discrimination score >70%) and 19 adults with poor hearing (PH). Specimens of healthy great auricular nerves (GAN) were collected from 7 adults undergoing unrelated neck dissections. Specimens were placed in sterile saline on ice for 15 minutes while being transported to the laboratory. Specimens were handled according to the institutional review board's study protocol approved by the Human Studies Committee of Massachusetts General Hospital and Massachusetts Eye and Ear Infirmary, and in accordance with the Helsinki Declaration. Age was defined at the time of diagnosis. Tumor size (largest diameter parallel to the petrous face), pure tone average (PTA, the average of the lowest thresholds (in dB) for two tones among 0.5, 1 and 2 KHz) and word discrimination (WD, the percentage of spoken words a patient can comprehend) were from the last measurements before tumor surgery. Tumor growth rate was derived from transverse or greatest dimension measurement changes in serial MRI scans.

Cytokine Array

Fresh human specimens were thoroughly washed in fresh sterile phosphate-buffered saline (PBS) three times before being incubated in 500 µL sterile PBS at 37° C. for 1 hour. The specimens were then removed from PBS and the tumor-conditioned PBS was stored at −80° C. until further use. The same procedure was followed for the VS and GAN specimens. Sterile PBS without specimen was incubated in parallel as a negative control. Human cytokine array membranes coated with 37 specific antibodies (RayBio Human Cytokine Antibody Array, RayBiotech, Inc.) were probed with 21 VS secretion samples, 7 GAN samples and 1 blank sterile PBS. Antibodies to 6 targets of particular interest due to our past work were shipped to the company for inclusion on the array: Mu-crystallin homolog (CRYM, Abnova, CA), αB-crystallin (CRYAB, Santa Cruz Biotechnology, Inc., CA), Merlin (NF2, Santa Cruz Biotechnology, Inc., Santa Cruz, Calif.), Fibronectin-1 (FN1, BD Pharmingen, CA), F-actin (ACTA1, Abcam, MA) and Versican (VCAN, Abcam, MA). The manufacturer's protocol was followed for experimental procedures and data analysis. Samples were dialyzed twice with PBS, pH 8. Protein concentrations of the dialyzed samples were measured spectrophotometrically and normalized through dilution in sterile PBS before incubation on the array membranes. Cytokine arrays were processed using standard manufacturer's protocol. Briefly, the membranes were exposed to the blocking buffer at room temperature (RT) for 1 hour, incubated with sample at 4° C. overnight, washed with Wash Buffer I and II at RT, incubated with biotin-conjugated antibodies at 4° C. overnight, and washed and incubated with HRP-conjugated streptavidin at RT for 1 hour. The membranes were incubated in detection buffer for 1 min and exposed in Chemidoc (Bio-Rad Laboratories, Hercules, Calif.) for 175-350 seconds to obtain a strong, clear signal. The relative expression levels were compared after performing a densitometric analysis using Quantity One (BioRad Laboratories, Hercules, Calif.). Probing with blank PBS treated in the same manner as the samples did not produce positive staining except at the positive control spots coated with the biotinylated IgGs.

Enzyme-linked Immunosorbent Assays (ELISA)

ELISA was conducted to validate the result obtained in cytokine array analysis. Tumor samples were collected and incubated in PBS as described above. A total of 8 VS secretions associated with GH and 10 VS secretions associated with PH were used. Majority of the samples used were from different patients than the samples studied in the cytokine array; 4 samples (3 GH and 1 BH samples) overlapped with the cytokine array sample group. ELISA for FGF2 and IL8 (Quantikine ELISA, R&D Systems, Minneapolis, Minn.) were used as per manufacturer's protocol. Tumor secretions were diluted in sterile PBS to have a total protein concentration of 30 µg/mL. In brief, duplicates were incubated in the 96-well immunoassay for 2 hours along with the standard and control sterile PBS, which served as background. The plate was washed four times with Wash Buffer, incubated with the specific enzyme-linked monoclonal antibody specific for FGF2 for 2 hours at RT, washed again, and incubated with the substrate solution. The stop solution was added and the plate was read using BioRad Model 680 (BioRad Laboratories, Hercules, Calif.) set to 450 nm, with a correction by 655 nm.

Cochlear Explant Culture

To develop an animal model to study hearing loss due to VS, cochlear explant cultures were established from postnatal CBA/CaJ mice aged P3-P5 (Jackson Laboratory, ME). Briefly, after decapitating the mouse, temporal bones were dissected from the skull in Hank's Balanced Salt Solution (Life Technologies, NY). The otic capsule encasing the cochlea was dissected out from each temporal bone. The otic capsule was carefully stripped away and the spiral ligament was peeled away from the entire cochlea, starting from the base. The basal turn of cochlea was then isolated using the dissecting knife (Fine Science Tools, CA), discarding the apical turn hook region. The tectorial membrane and the Reissner's membrane were removed, leaving the organ of Corti intact with the spiral ganglion neuron region. This explant was cultured onto a 10 mm glass coverslip coated with CellTak (BD Biosciences, CA, #354241) in a 35 mm culture dish with 4 wells. Cells were cultured in 98% DMEM, 1% ampicillin and 1% N2 supplement.

Gentamicin and FGF2 Treatment of Cochlear Explants

To assess FGF2's otoprotective effect, cochlear explant cultures were treated with recombinant human FGF2±gentamicin. After culturing the explants overnight, media fortified with FGF2 (100 ng/mL) was applied. Twenty-four hours later media fortified with gentamicin (1 mM) and FGF2 (100 ng/mL) was applied. These concentrations were based on previous literature demonstrating gentamicin-induced ototoxicity and FGF2's otoprotective effect in cochlear explant cultures. Cochlear explants were fixed after an additional 24 hours of treatment, with total time being 48 hours.

Immunofluorescence and Imaging

After treatment, the explants were fixed and stained with antibodies against myosin 7A (Myo7A, Proteus Biosciences, CA) and β-tubulin (Tuj1, Covance, MA) to identify hair cells (HCs) and neurons, respectively. The same immunofluorescence protocol as described in Example 1 was used, with the exceptions of omission of 1N HCl incubation, usage of 5% NHS with 1% Triton-X for blocking solution and 1% NHS with 0.4% Triton-X solution for primary antibody incubation at room temperature (RT). Secondary antibodies (Alexa Flour 555 anti-mouse and Alexa Four 488 anti-rabbit) were purchased from Life Technologies. Cochlear explants were imaged using a Leica TCS SP5 Confocal microscope. Zoomed-in pictures for the region of organ of Corti, including neurites, were merged in a z-stack to obtain a z-axis projection image in the Leica software. The number of hair cells (HCs) and neurites were manually counted per 100 µm length along the cochlea, with 1-2 samplings per specimen.

Statistical Analyses

For the cytokine array, proteins were determined to be significantly expressed if the corresponding spots had optical densities more than 2 standard deviations of background values above the mean background level for each array. For the cytokine array and ELISA, statistical significance was determined through an analysis of variance (ANOVA) with alpha set to 0.05. For cochlear explant experiments, differences were analyzed using a two-tailed t-test, with $p<0.05$ considered significant.

Results

Figure 13:
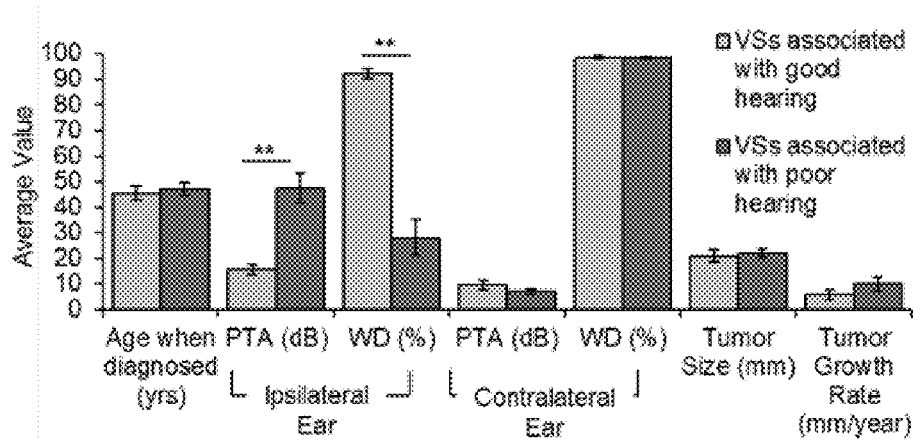
FIG. 13 is a bar graph illustrating the patient demographics for VS secretions used in cytokine array and ELISA. Age, pure tone average (PTA) and word discrimination (WD) for ipsilateral and contralateral ear, tumor size measured in transverse dimension in the cerebellopontine angle (based on most recent MRI scan prior to surgical excision), and tumor growth rate (based on change in transverse or greatest dimension between the first and last preoperative MRI scans) are shown. n=16 in GH and n=19 in PH group. Error bars represent SEM. p<0.01.
Figure 14:
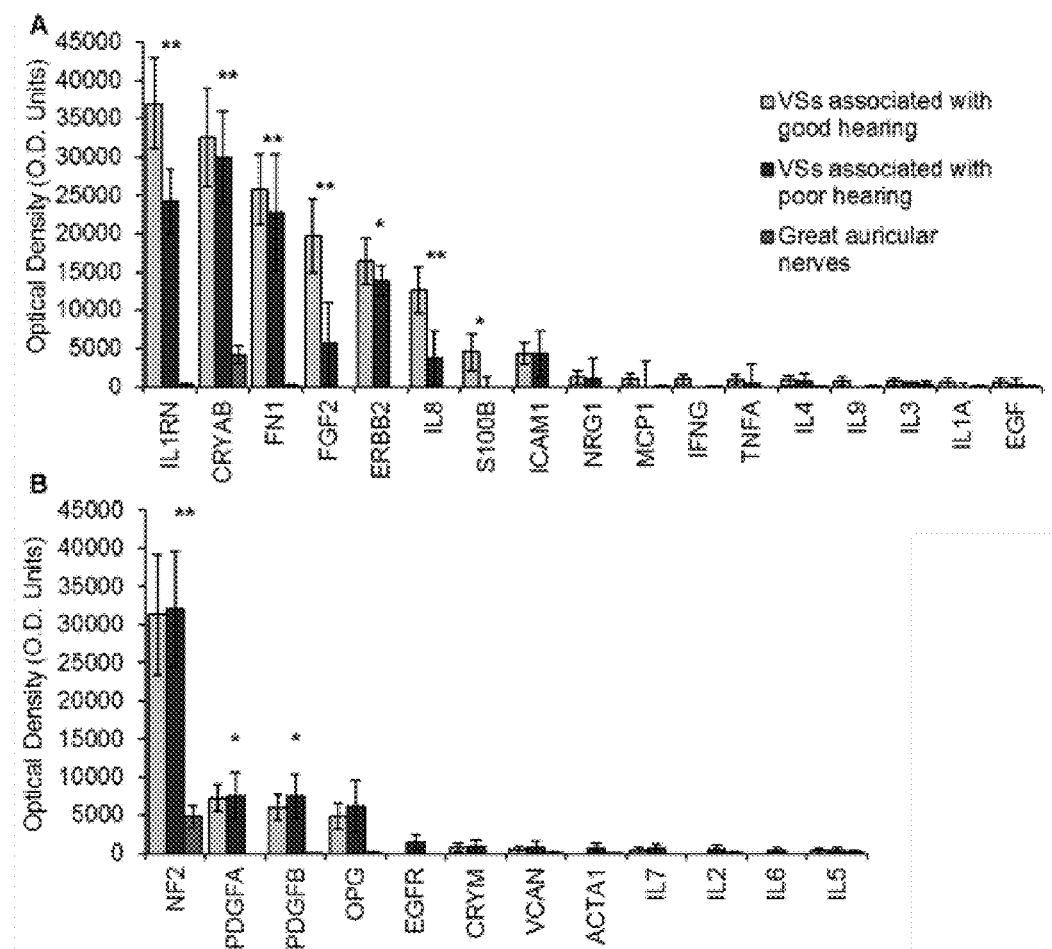
FIG. 14 is a bar graph of the cytokine array results for 37 proteins studied. Means and SEM are plotted for secretions from VS associated with GH (light grey columns, n=11) and PH (darkest grey columns, n=10) and control GAN (medium grey columns, n=7). A. Protein secreted at higher levels in VS associated with GH versus PH; B. Proteins secreted at higher levels in VS associated with PH versus GH. IL1B, IL10, IL12B, IL13, IL15, IL17, TNFB and CEA are not shown as they were not significantly secreted in VS or GAN. Statistical significance of *p<0.05 or **p<0.01 refers to VS secretions (combining GH and PH) versus GAN secretions.

Fibroblast Growth Factor 2 Levels are Negatively Correlated with Degree of VS-associated Hearing Loss Tumors associated with GH significantly differed from those associated with PH in PTA ($p<0.001$) and WD scores ($p<0.001$) of the ipsilateral ear, but not with respect to age ($p=0.70$), sex ($p=0.92$), VS size ($p=0.71$), PTA ($p=0.25$) or WD ($p=0.80$) of the contralateral ear (FIG. 13). Of the 37 proteins studied, listed in the Table 3, nine were significantly expressed in the VS secretions compared with GAN controls (FIG. 14).

TABLE 3

Table of protein symbols and names used in cytokine array

| Symbol | Protein Name |
| --- | --- |
| IL1A | Interleukin-1 α |
| IL1B | Interleukin-1 β |
| IL1RN | Interleukin-1 Receptor Antagonist |
| IL2 | Interleukin-2 |
| IL3 | Interleukin-3 |
| IL4 | Interleukin-4 |
| IL5 | Interleukin-5 |
| IL6 | Interleukin-6 |
| IL7 | Interleukin-7 |
| IL8 | Interleukin-8 |
| IL9 | Interleukin-9 |
| IL10 | Interleukin-10 |
| IL12B | Interleukin-12 p40 |
| IL13 | Interleukin-13 |
| IL15 | Interleukin-15 |
| IL17 | Interleukin-17 |
| NRG1 | Neuregulin-1 β |
| EGF | Epidermal Growth Factor |
| CCL2 | Monocyte Chemotactic Protein 1 |
| IFNG | Interferon-gamma |
| TNF A | Tumor Necrosis Factor α |
| FGF2 | Fibroblast Growth Factor 2 |
| S100B | s100 Calcium Binding Protein β |
| CEA | Carcinoembryonic Antigen |
| PDGFA | Platelet-Derived Growth Factor AA |
| PDGFB | Platelet-Derived Growth Factor BB |
| ICAM1 | Intercellular Adhesion Molecule 1 |
| CRYM | Crystallin, Mu |
| CRYAB | Crystallin, α-B |
| VCAN | Versican |
| NF2 | Neurofibromin 2 |
| EGFR | Epidermal Growth Factor Receptor |
| ERBB2 | Tyrosine Kinase Cell-surface receptor HER2 |
| OPG | Osteoprotegrin |
| TNF B | Tumor Necrosis Factor β |
| FN1 | Fibronectin-1 |
| ACTA1 | F-Actin, Polymer form |

Figure 15:
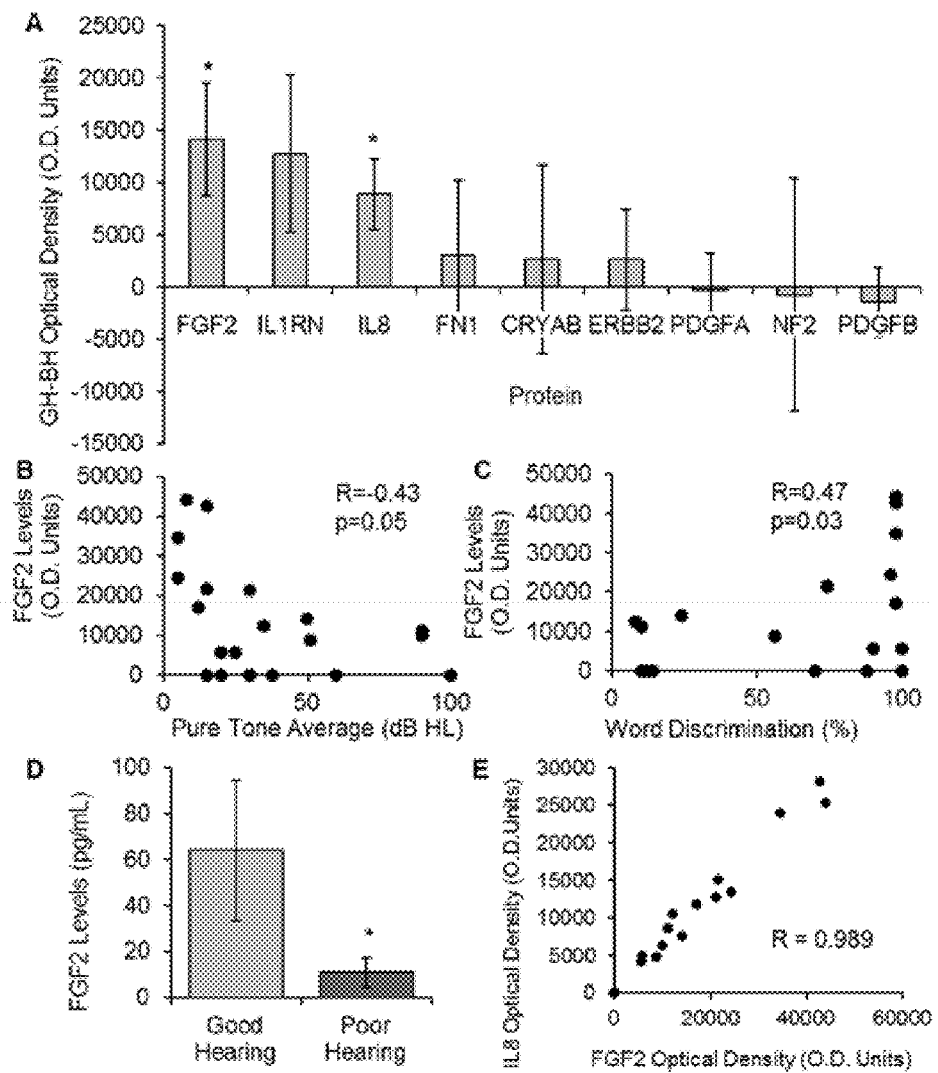
FIG. 15 is the analysis of significantly aberrant pathways in VS. Of the 9 proteins that were secreted by VS at significantly different levels than GAN, FGF2 and IL8 met statistical criteria for differential secretion levels between tumors associated with GH versus PH. A. The difference in optical density between GH and PH group is plotted as mean±SEM. B. Correlation of pure tone average (dB) of ipsilateral ear to the VS and measured secreted FGF2 levels from the tumor C. Correlation of word discrimination score (%) of ipsilateral ear to the VS and measured secreted FGF2 levels from the tumor, R represents Pearson's correlation coefficient. D. FGF2 levels as measured using ELISA of independent set of VS secretions, stratified by VS associated with good hearing (n=8) and associated with poor hearing (n=10). Error bars represent SEM. E. FGF2 and IL8 secretion levels were closely correlated among samples. Each point represents one sample; 2 GH samples and 4 BH samples are not shown as their FGF2 and IL8 levels were within background level. *p≤0.05.

Of these, six demonstrated a trend for higher (FIG. 14A) and three demonstrated a trend for lower expression (FIG. 14B) in the tumors associated with good versus poor hearing. One molecule met our criteria for statistically different level of expression between the two groups: FGF2 was 3.5-fold higher ($p=0.017$) in the VS associated with GH versus VS associated with PH (FIG. 15A). Although this study attempted to investigate IL-8 expression in VS, the antibody was not specific and provided incorrect results.

Further, FGF2 expression was significantly negatively correlated with the pure tone average ($R=-0.43$, $p=0.05$, FIG. 15B) and positively correlated with word discrimination score ($R=0.47$, $p=0.03$, FIG. 15C) of the patients in the ipsilateral ear as the VS. Results of cytokine array analysis were validated on a different set of tumor secretions using FGF2 ELISA. We again found FGF2 at substantially higher levels in secretions associated with good versus poor hearing ($p=0.05$). The magnitude of the difference in average expression detected was higher with ELISA (5.8-fold change) (FIG. 15D) in comparison to the cytokine array, possibly due to the greater sensitivity of the antibody used in ELISA versus the proprietary antibody in the cytokine array, or due to biological differences in tumor samples.

Of the 9 molecules significantly expressed in VS (FIG. 14), most are known to be secreted. However, three molecules are typically not secreted (CRYAB, ERBB2 and NF2), and their presence in tumor secretions is consistent with shedding (Black, 1980; Taylor & Black, 1986; Steffensen et al., 2008).

Figure 16:
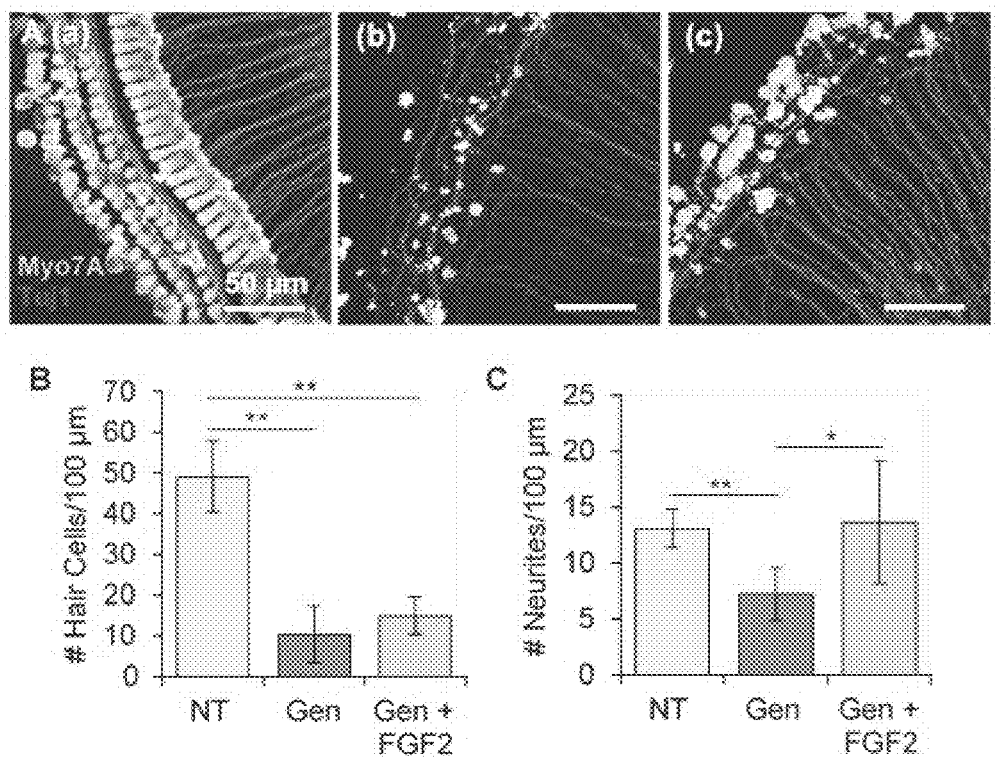
FIG. 16 is demonstrative of FGF2's otoprotective effect against gentamicin. A. Representative images highlighting HCs (Myo7A, medium grey) and neurites (Tuj1, dark grey) of non-treated (NT, n=8, a), 1 mM gentamicin-treated (Gen, n=7, b) and 100 ng/mL FGF2 with 1 mM gentamicin (Gen+FGF2, n=3, c) treated cochlear explant cultures. Scale bar=50 μm for all images. B. Number of total HCs and C. neurites present in 100 μm section of cochlear explant cultures receiving NT, Gen and Gen+FGF2 treatments. Error bars represent SD. *p<0.05, **p<0.01

Fibroblast Growth Factor 2 can Prevent Neurite Loss Due to Gentamicin Treatment in Cochlear Explant Cultures Gentamicin led to significant loss of hair cells (HCs) and neurites, and FGF2 pre-application could prevent the neurite loss. Representative projection images of untreated, gentamicin-treated and FGF2 and gentamicin-treated cochlear explants are shown in FIG. 16A (a-c), respectively. Data are summarized as average±standard deviation for non-treated (NT), gentamicin treated and gentamicin and FGF2 treated cochlear explants. The total number of HCs per 100 μm length reduced from 49.1±8.7 (n=8 different explants) to 10.4±7.0 (n=7 different explants, $p=0.0000004$) after gentamicin treatment. This HC loss could not be prevented with FGF2, being 15.0±4.6 (n=3 different explants, $p=0.0001$ in comparison to NT and $p=0.34$ in comparison to gentamicin alone) (FIG. 16B).

The number of neurites reduced from 13.1±1.7 (n=8 different explants) to 7.3±2.3 (n=8 different explants, $p=0.00005$) after gentamicin treatment. This neurite loss was prevented with FGF2, being 13.7±5.5 (n=3 different explants, $p=0.79$ in comparison to NT and $p=0.02$ in comparison to gentamicin alone) (FIG. 16C). These results confirm FGF2's otoprotective role against gentamicin and help establish a cochlear explant model to study SNHL due to VS secreted factors.

Discussion

A comparative screening of 37 molecules in VS associated with good versus poor hearing identified FGF2 as a potential mediator of hearing protection in VS. The result was robust between the two different techniques applied to different samples despite the large inter-sample variability typically observed in human samples. Nine targets were found to be significantly present in the VS secretions relative to GAN. Some of these targets (CRYAB, NF2, ERBB2, PDGFA, PDGFB, and FGF2) have been previously studied in VS pathobiology (Welling et al., 1996; Hanemann et al., 2006; Hansen et al., 2006; Koutsimpelas et al., 2007; Ousman et al., 2007; Lysaght et al., 2011). FGF2 is a known mitogen for VS proliferation (Weerda, 1998) but it had not been previously studied in the context of SNHL due to VS. Increased levels of FGF2 in tumors associated with good hearing suggest that FGF2 secreted by the tumors may exert hearing protection. This conjecture is intriguing because of FGF2's known role in protection of the auditory neurons and HCs from acoustic trauma, glutamate toxicity and neomycin ototoxicity (Low et al., 1996; Yin et al., 2002; Zhai et al., 2002; 2004). It is possible that FGF2 secreted by VS, or by the cranial nerves surrounding VS, protect the auditory nerve and cochlea from damage and death caused by various mechanisms, including nerve compression or structural degradation. VS are known to be associated with substantial degeneration of cochlear structures, including loss of HCs and cochlear neurons (Roosli et al., 2012). FGF2 may be involved in limiting this degeneration in patients with VS that continue to have GH. It may be that FGF2 is blocking a putative neurotoxic or ototoxic substance, or interfering with the pathway(s) this substance controls, or easing death from nerve compression. Since no causative studies for SNHL due to VS have been conducted thus far, a model is needed to assess the mechanisms through which FGF2 is asserting its protective role on the cochlear and neuronal cells.

To establish a model to study the role of different VS secreted factors and to assess FGF2's otoprotective potential, we established a murine organotypic cochlear explant culture model and tested it with FGF2's otoprotective capability against gentamicin. Previously, FGF2 has been shown to protect rat cochlear explant HCs from neomycin toxicity (Low et al., 1996). Although we did not see decreased HC loss with FGF2 treatment in the mouse model, there was an apparent prevention of neurite loss, in line with previous findings that FGF2 protects the auditory nerve against noise-induced damage and glutamate toxicity (Zhai et al., 2004). It was surprising that we did not see prevention of HC loss due to FGF2. It could be because the gentamicin and FGF2 concentrations were too high or too low, respectively, or due to interspecies differences as FGF2's otoprotective capability had not been established in mice. A previous study on gentamicin-treated rat cochlear explants obtained similar results, with 25% neurites lost and almost complete HC loss with a 1 mM concentration (Zheng and Gao, 1996). Further when treating cultures with 3 mM gentamicin, the authors could not prevent HC or neurite loss with 100 ng/mL FGF2, presumably due to the high dose of gentamicin (Zheng and Gao, 1996). Establishing dosage curves for gentamicin and FGF2 in murine cochlear explants in future experiments would assist in delineating FGF2's otoprotective capability against gentamicin. Nonetheless, the cochlear explant model can be used to study the impact of VS secreted factors by application of secretions with specific manipulations such as neutralization of or augmentation with a given protein, followed by quantification of cochlear damage. For instance, future work could be directed towards studying the role of FGF2 within VS secretions by neutralizing FGF2 or by augmenting with exogenous FGF2. This paradigm will enable us to causatively study the role of specific molecules within the VS secretome.

Our finding of high levels of FGF2 secretions by VS associated with good hearing, combined with the known role of FGF2 as mitogen of VS in vitro (Weerda, 1998) and its correlated expression with VS growth in vivo (Koutsimpelas et al., 2007), is consistent with the published reports of large VS that do not cause SNHL (Nadol et al., 1996; Cayé-Thomasen et al., 2007; Arriaga, Long, & Nelson, 1993). Our data suggest that FGF2 may mediate tumor growth and hearing level by different mechanisms. If the pathways that lead to tumor growth are divergent from the pathways that modulate hearing, then tumor size or growth rate do not have to correlate with SNHL. This notion is supported by our cytokine array analysis where levels of well-established growth modulators, such as ERBB2, did not correlate with the hearing level, and FGF2 levels did not correlate with tumor size. We could calculate tumor growth rate for only 14 out of the 35 tumors because only 40% of the studied patients were followed by serial MRI scans prior to surgical excision. Within this small subset of tumors, we did not find a significant correlation between tumor growth rate and hearing outcome. This is in contrast to the prior work that found a correlation between high tumor growth rate or large tumor size and poor hearing (Meyer et al., 2006; Sughrue et al, 2010). These divergent findings are likely not only due to the differences in the sample size, but also due to the methodological or definitional differences, such as the definition of tumor size and hearing loss.

If the putative otoprotective and neuroprotective effects of FGF2 secreted by VS are to be explored in future therapies to preserve hearing in patients with VS, exogenous FGF2 would have to be modified to minimize its growth promoting potential. Recently, FGF2 application onto the tympanic membrane was extremely efficacious in healing the membrane (Lou, 2012), providing a promising methodology to apply FGF2 locally to the ear. Additionally, if FGF2 levels could be measured in the tumor microenvironment, such as by sampling blood serum or cerebrospinal fluid (Salven et al., 2000; Larsson, Sknöldenberg & Ericson, 2002; Blasko et al., 2006), then physicians could utilize FGF2 as a biomarker for prognosis of the likelihood of SNHL in patients with VS, which would influence counseling and surgical decision making.

It is reassuring that many proteins previously implicated in pathology of VS and/or SNHL were found to be significantly elevated in VS compared with control GAN in the present study. Consistent with our work, in which merlin, the protein encoded by the NF2 gene, was absent in 3 out of 21 VS secretions, another study found approximately 23% of tumors to have alterations or loss of both NF2 alleles (Sainz et al., 1994). About 81% of sporadic schwannomas have mutated NF2 genes with small deletions, and 93% of these mutations result in truncated proteins with defects in all or part of the C-terminus (Sughrue et al., 2011b). Because the NF2 antibody used in the cytokine array targets the N-terminus of the protein, we could detect NF2, even if mutated. ERBB2, known to shed in other types of cancers (Colomer et al., 2000), was also found to be present in 17 out of the 21 tumor secretions. Our results are consistent with past work demonstrating ERBB2 in VS, where it plays a role in tumor proliferation and survival (Ahmad et al., 2011). Similarly, platelet derived growth factor AA (PDGFA) and platelet-derived growth factor BB (PDGFB) have been implicated in VS pathobiology (Wang et al., 1994; Hanemann et al., 2006), and we found both to be present in 13 out of 21 VS secretions. We detected a trend, albeit not significant (p=0.93), for higher PDGFA secretion by VS associated with PH in comparison with GH (FIG. 15A). This trend is consistent with a cDNA microarray analysis published previously (Lassaletta et al., 2009). The decrease in significance between the current and prior study may be because we analyzed protein secretions using a larger sample size.

Interestingly, interleukin-1 receptor antagonist (IL1RN) was found to be substantially elevated in tumor secretions associated with GH versus PH, although the result did not meet our criterion for statistical significance (p=0.10). IL1RN serves to block the receptor for interleukin-1 (IL1) and therefore prevent IL1 signaling. Therapeutic blockade of IL1A and IL1B has been suggested to treat sensorineural SNHL (Goldbach-Mansky et al., 2006). Fibronectin-1 (FN1), seen in our previous work as a biomarker for vestibular schwannomas in perilymph (Lysaght et al., 2011), was also found to be significantly higher in the VS secretions when compared with GAN secretions (p<0.001). A larger sample size as well as a more extensive set of molecular targets will be needed in future studies to validate the results of the current work. It is likely that several different mechanisms lead to the spectrum of SNHL seen with VS, and that these mechanisms vary in significance through a tumor's progression for different patients.

Conclusion

Sporadic VSs secrete cytokines at substantially higher levels than control nerves. In this work, we identified the first VS-secreted factor that correlated with degree of SNHL, supporting the hypothesis that VS-secreted molecules can modulate hearing in patients. Specifically, we found a correlation between levels of VS-secreted FGF2 and hearing in sporadic VS patients. This was consistent with previous findings in which FGF2 demonstrated an otoprotective and neuroprotective role against other insults leading to SNHL. Additionally, FGF2's otoprotective capabilities were assessed using a gentamicin-treated cochlear explant culture model. This model provides a tool to study SNHL due to VS in the subsequent examples.

Example 6

Secreted Factors from Vestibular Schwannomas can Cause Cochlear Damage

To establish a model to study the role of VS secreted factors in causing cochlear damage, we developed and optimized a cochlear explant culture model as described in Example 5. In this example, cochlear explant cultures were treated with tumor secretions from three different sporadic VSs of patients demonstrating substantial hearing loss. Each tumor demonstrated a different pattern of cochlear explant damage. VS-A, derived from an ipsilaterally deaf patient, did not lead to significant cell death, although it did lead to drastic fiber disorganization, including afferent and efferent fibers. VS-B, derived for a patient with moderate SNHL ipsilaterally, led to significant loss of outer hair cells and neurites. VS-C, derived from an ipsilaterally deaf patient, led to significant degeneration, including loss of inner hair cells, outer hair cells and neurites, with increasing severity from the apical to the basal turn. Our results are the first to demonstrate that VS secreted factors can lead to cochlear damage. Additionally, these tumors secreted differential levels of protein of interest. The subsequent examples will study the role of these specific molecules within the VS secretions.

Introduction

SNHL due to VS seems to be mechanistically complex since sporadic VS size or the intracanicular extent does not correlate with the extent of SNHL (Nadol et al., 1996; Cayé-Thomasen et al., 2007). Additionally, significant cochlear atrophy has been noted in patients with untreated sporadic VS with significantly more inner and outer hair cell loss, cochlear neuronal loss and proteinacious precipitate in endolymph and perilymph (Roosli et al., 2012). Since in the case of NF2, VS size does correlate with degree of SNHL, it may be that the mechanisms of SNHL due to NF2 VS versus sporadic VS are divergent, albeit overlapping. To focus our hypothesis, we have concentrated on sporadic VSs to study SNHL due to VS. We explored the hypothesis that VS-secreted molecules, through their effect on cochlear cells, can modulate SNHL due to these tumors. Although postulated, causative experiments to explore this hypothesis have not been published. Here, we have applied VS secretions, collected by incubated fresh VS specimens in culture media, to cochlear explants and assessed damage due to this treatment.

Based on findings by Roosli et al. (2012), we focused on hair cell and neurite loss. Although neuron loss would have been an important measure, we could not accurately quantify this measure due to interspecimen variability arising from thickness of specimen and intraspecimen differences in neuron densities. We considered neurite loss as a proxy for neuronal loss, as both suggest neural degeneration.

We tested three different human VS secretions on the murine cochlear explants. Two VSs, from patients having SNHL only on the ipsilateral side, led to loss of hair cells (HCs) and neurites in the cochlear explants, which was reflective of the patient's degree of SNHL. Intriguingly, the third VS, from a patient who had severe ipsilateral SNHL and also a moderate contralateral SNHL, did not lead to cell loss but rather fiber disorganization. Overall, this is the first demonstration the VS secreted factors can cause cochlear damage. Several molecules are most likely involved in causing the damage noted and our focus on four molecules, i.e. FGF2 (Example 5), TNFα (Example 7), VEGF-A and HGF (Example 8) is discussed in the other examples.

In this example, we describe that applying secretions from VS of patients who had varied levels of SNHL led to differential damage in the cochlear explants, with apparent loss of HCs and neurites.

Methods

VS Secretion Preparation

After removing cauterized and hemorrhagic parts of the fresh sporadic VS specimens, the specimen was washed with sterile PBS thrice. VS secretions were collected by incubating a washed, fresh tumor specimen in 100% DMEM for 3 days at 37° C. and 5% $CO_2$ levels in sterile conditions. The secretions were normalized by weight (0.1 g specimen/0.1 mL DMEM). In addition, DMEM alone was incubated in parallel as control media. After removing the tumor piece, the secretions were then frozen at −80° C. until further use.

Secretion Application onto Cochlear Explants

The same general methodology for murine cochlear explant cultures as described in Example 5 was utilized. Cochlear explant cultures were established from P2-P3 mice. Importantly, instead of only culturing the basal turn, the apical turn was also isolated, providing two pieces per cochlea with a greater frequency range. After approximately 12 hours, the cochlear explant cultures were treated for 48 hours with tumor secretions diluted to half their concentration. The formulation was 46.5% tumor-conditioned DMEM, 46.5% plain DMEM, 5% FBS, 1% ampicillin and 1% N2 supplement. Cochlear explants were treated with control media in parallel, being 46.5% DMEM incubated without tumor, 46.5% plain DMEM, 5% FBS, 1% ampicillin and 1% N2 supplement. All reagents were purchased from Life Technologies, NY. Osmolality in the solutions was measured in samples using a vapor-pressure osmometer (standardized with 290 mOsm/kg of 0.1567M sodium chloride solution) before applying them onto cochlear explants. Extra formulation for each VS secretion was made to be tested on Milliplex arrays and ELISA. Milliplex array, containing FGF2, VEGF-A and HGF beads (Millipore) and human TNFα ELISA (R&D Systems) were conducted as directed by the manufacturer on VS secretions prior to being applied onto the cochlear explant cultures.

Immunofluorescence and Imaging

Cochlear explants were fixed 48 hours after treatment and the same methodology for VS secretion application as described in Example 5 was utilized. Additional parameters, along with total HC loss and neurite loss, were assessed in the cochlear explants, being inner hair cell (IHC) loss, outer hair cell (OHC) loss, and level of fiber organization. Number of IHCs and OHCs was counted as IHCs (being the row of cells located more centrally) or OHCs per 100 μm. Fiber organization, including both afferent radial neurites to the IHCs and efferent spiraling neurites from the OHCs, was assessed using a qualitative scale with 0 being essentially intact and 2 being severe disorganization.

Results

VS Secretions from Patients Ranging from Moderate to Severe Hearing Loss

Figure 17:
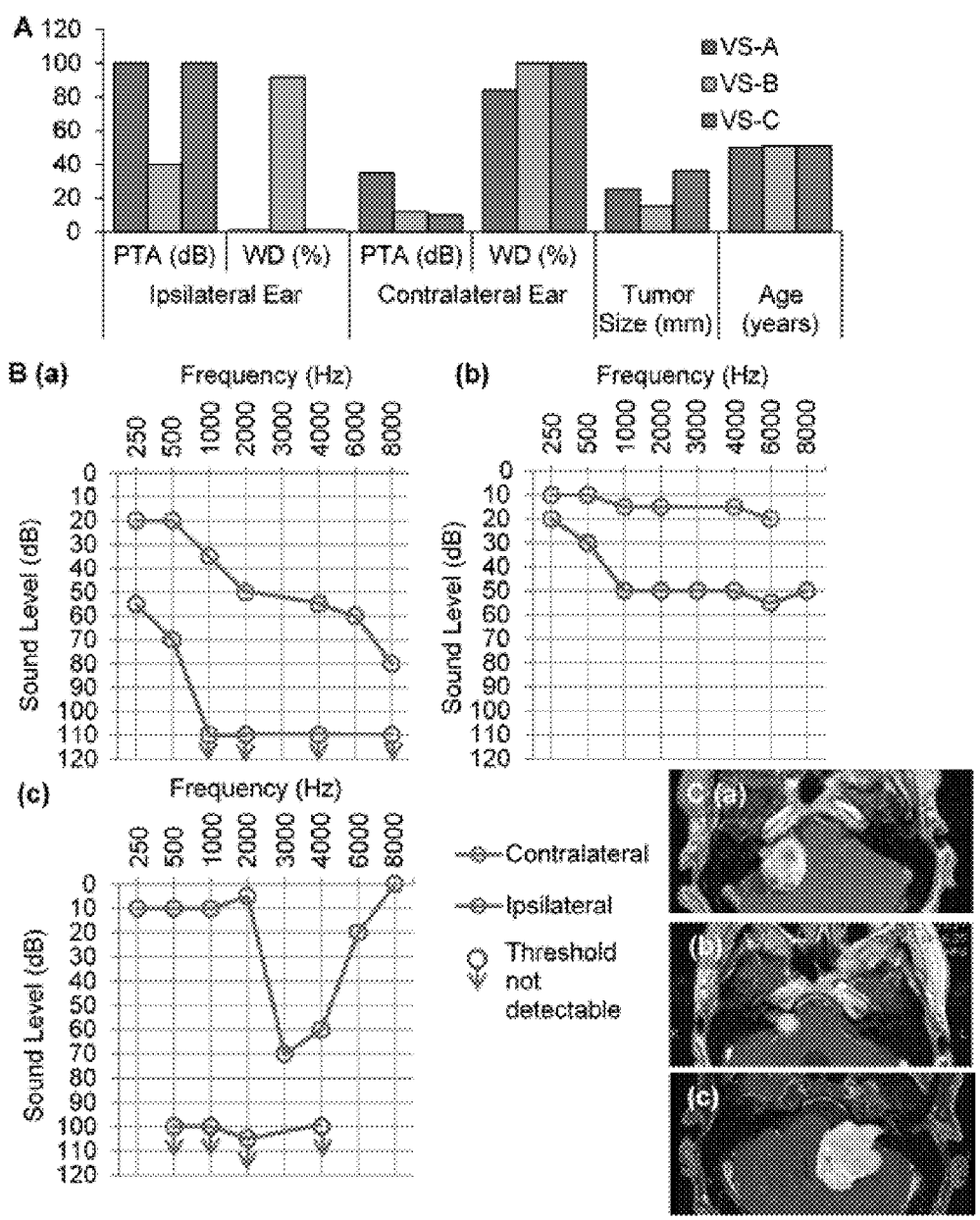
FIG. 17 is illustrating the patient demographics for VS secretions applied to cochlear explants. A. Pure tone average (PTA, dB), word discrimination (WD, %) are given for the ipsilateral and contralateral ears to VS. Tumor size (mm, largest transverse dimension) and age (years) are also shown. Most recent audiometric data prior to VS surgical resection for VS-A, VS-B and VS-c patients were used. B. Most recent audiograms prior to surgical resection for (a) VS-A, (b) VS-B, and (c) VS-C patients are given demonstrating thresholds of hearing for the ipsilateral (red line) and contralateral ear (blue line) to the VS. Arrow represents thresholds still not achieved at the given sound level. C. Most recent MRI scans prior to surgical resection for (a) VS-A, (b) VS-B, and (c) VS-C patients.

All patients had unilateral, sporadic VSs. Summary of patient demographics and hearing status is provided in FIG. 17A. Audiograms for patients with VS-A, B and C are shown in FIG. 17B (a-c), respectively. VS-A was a 25 mm VS from a 50-year old male with gradual SNHL leading to a pure tone average (PTA, the average of the lowest thresholds (in dB) for two tones among 0.5, 1 and 2 KHz) of ≥100 dB and word discrimination (WD, the percentage of spoken words a patient can comprehend) score of 0% ipsilaterally (deaf ear). The contralateral ear had a moderate SNHL, with a 35 dB PTA and 84% WD. The patient had a significant history of noise exposure including chain saws and heavy equipment without ear protection. This SNHL was present 2 years prior to the surgical resection with no recent audiograms. The patient also had significant vestibular symptoms, with previous episodes of vertigo and dizziness. VS-B was a 15 mm VS from a 51-year old female with sudden SNHL leading to a PTA of 40 dB and 92% WD.

The contralateral ear had a 12 dB PTA and 100% WD. An audiogram taken six months prior for this patient demonstrated SNHL which did not improve with steroid therapy. The most recent audiogram demonstrated the ipsilateral ear having a downward sloping SNHL. The contralateral ear had essentially normal hearing. The patient had no notable vestibular symptoms. VS-C was a 36 mm VS from a 51-year old male with a recent gradual SNHL ipsilaterally over several months to a year leading to a PTA of ≥100 dB and WD score of 0% (deaf ear). The contralateral ear had normal hearing with a 10 dB PTA and 100% WD with the exception of a 70 dB notch at 3000 Hz. The patient had vestibular symptoms being light headedness without whirling vertigo. As only one pre-operative MRI was available for each patient, tumor growth rates could not be calculated for these patients.

Loss of Hair Cells and Neurites in Cochlear Explants Due to VS Secretions

Secretions from different tumors led to different types and degree of damage in the cochlear explants. The only significant morphological change due to VS-A secretions was disorganization of the fibers in both the apical and basal turns. VS-B led to significant loss of OHCs specifically in the basal turn and neurite loss in both apical and basal turns. Additionally, fibers were significantly disorganized in the apex. VS-C led to drastic degeneration in the cochlear explants, including significant loss of IHCs and OHCs in the apical and basal turns. There was also significant loss of neurites in the basal turn and fiber disorganization in the apical and basal turns. Representative projection images for the apical turn are shown for cochlear explants treated with control media (NT), VS-A, VS-B and VS-C secretions in FIG. 18A (a-d), respectively. Representative images for the basal turn are shown for cochlear explants treated with NT, VS-A, VS-B and VS-C secretions in FIG. 18A (e-h), respectively.

Data are summarized as average±standard deviation. N represents the number of different cochlear explant cultures tested for a given treatment. The number of inner hair cells (IHCs) per 100 μm length for the apical turns for NT, VS-A, VS-B and VS-C secretions were 13.0±1.0 (n=5 different explants), 12.3±1.2 (n=4 different explants, p=0.17), 12.0±4.4 (n=3 different explants, p=0.17) and 7.2±5.0 (n=5 different explants, p=0.03), respectively (FIG. 18B).

Figure 18:
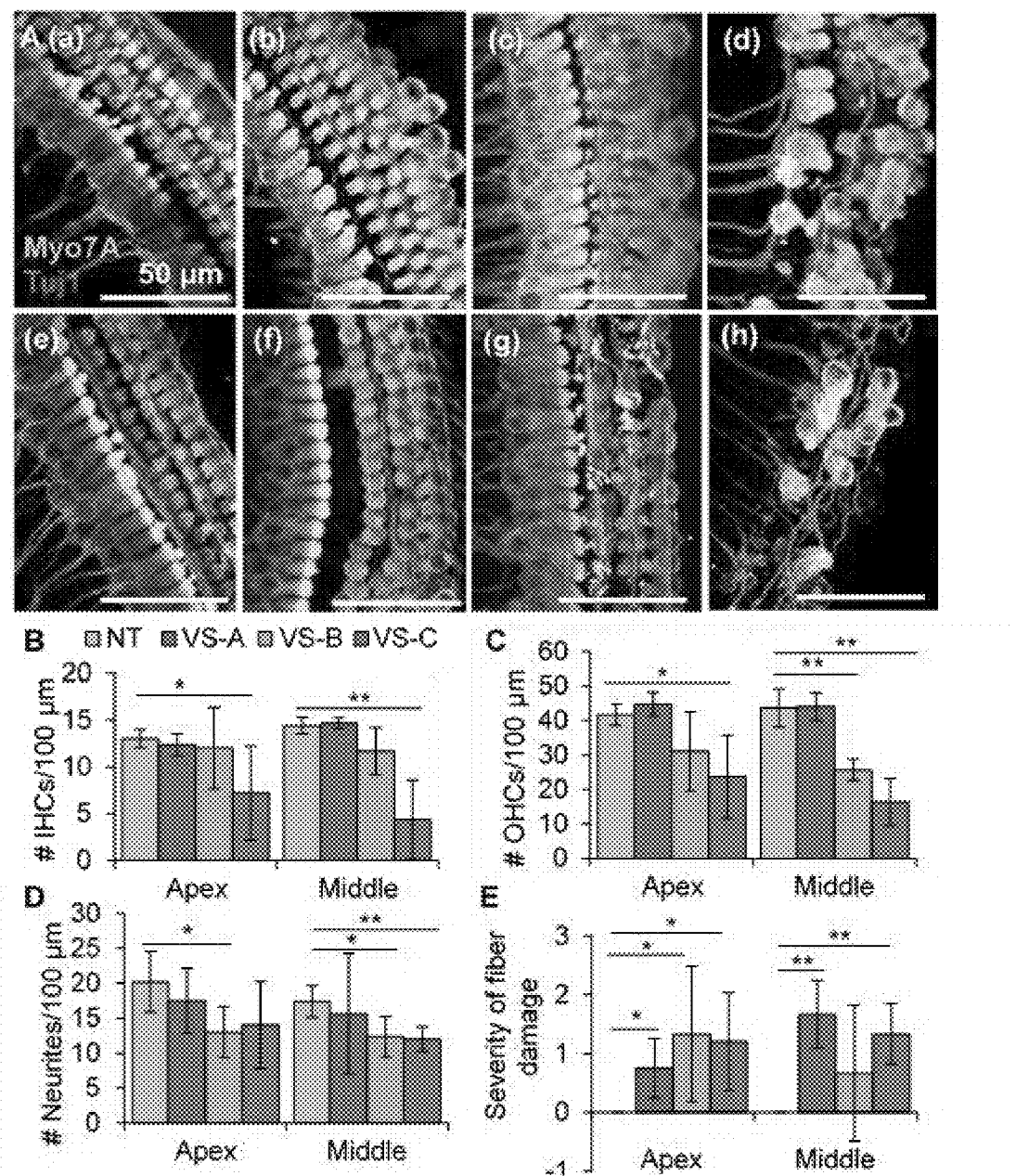
FIG. 18 is the application of human VS secretion onto murine cochlear explant cultures leads to hair cell and neurite loss. A. Representative images for cochlear explants receiving no treatment (NT, n=5 different explants, a), incubated with VS-A (n=4 different explants, b), VS-B (n=3 different explants, c), and VS-C (n=5 different explants, d) secretions are shown for the apical and NT (n=4 different explants, e), VS-A (n=3 different explants, f), VS-B (n=3 different explants, g), and VS-C (n=6 different explants, h) secretions for the basal turn. Myo7A (green) marks hair cells and Tuj1 (red) marks neurites. Scale Bar=50 μm applies to all images. B. Number of inner hair cells (IHC), C. outer hair cells (OHC), D. neurites, and E. severity of fiber damage are shown for a 100 μm length within the apex and basal turn cochlear explants treated with NT (grey columns), VS-A (red columns), VS-B (green columns) and VS-C (blue columns) secretions. *p<0.05, **p<0.01.

The number of IHCs per 100 μm length for the basal turns for NT, VS-A, VS-B and VS-C secretions were 14.5±1.0 (n=4 different explants), 14.7±0.6 (n=3 different explants, p=0.81), 11.7±2.5 (n=3 different explants, p=0.06) and 4.3±4.2 (n=6, p=0.002), respectively (FIG. 18B). N is the same in the rest of analyses as for IHC counts for all treatments. The number of outer hair cells (OHCs) per 100 μm length for the apical turns for NT, VS-A, VS-B and VS-C secretions were 41.6±3.0, 44.7±3.5 (p=0.88), 31.0±11.5 (p=0.09) and 23.6±12.0 (p=0.01), respectively (FIG. 18C). The number of OHCs per 100 μm length for the basal turns for NT, VS-A, VS-B and VS-C secretions were 44.0±6.3, 44.0±4.0 (p=1), 25.7±3.0 (p=0.002) and 16.3±6.9 (p=0.0002), respectively (FIG. 18C). The number of neurites per 100 μm length for the apical turns for NT, VS-A, VS-B and VS-C secretions were 20.2±4.3, 17.5±4.7 (p=0.40), 13.0±3.6 (p=0.05) and 14.0±6.2 (p=0.10), respectively (FIG. 18E). The number of neurites per 100 μm length for the basal turns for NT, VS-A, VS-B and VS-C secretions were 17.5±2.7, 15.7±8.6 (p=0.69), 12.3±2.9 (p=0.03) and 12.0±1.7 (p=0.007), respectively (FIG. 18E).

The severity of fiber damage was assessed qualitatively with 0 being essentially intact and 2 being most severe. The radial fibers arising from the modiolar region consist mostly of afferent fibers synapsing from the IHCs and going to the neurons, with a small population of efferent fibers going from the neurons to the IHCs. The spiraling fibers in the periphery of the specimen mostly contain efferent fibers coming from the medial olivary complex within the superior olive and synapsing onto the OHCs to modulate their function as amplifiers, with a smaller population of afferent fibers coming from OHCs. Although more central centers, such as the superior olive, are not present in the cochlear explant cultures, nerve fibers synapsing at the IHCs and OHCs remain intact and organized in control specimens (FIG. 18A (a), C). In contrast, nerve fiber disorganization is noted in explants treated with VS secretions. Severity of fiber damage per 100 μm length for the apical turns for NT, VS-A, VS-B and VS-C secretions were 0.0±0.0, 0.75±0.5 (p=0.01), 1.3±1.2 (p=0.03) and 1.2±0.8 (p=0.01), respectively (FIG. 18E). Severity of fiber damage per 100 μm for the basal turns for NT, VS-A, VS-B and VS-C secretions were 0.0±0.0, 1.7±0.6 (p=0.002), 0.7±1.2 (p=0.22) and 1.3±0.5 (p=0.001), respectively (FIG. 18E).

Overall, differential levels of damage were noted due to different VS secretions. There was a general trend of increasing damage from apical to basal turns. Osmolality did not significantly deviate from control media, being 323, 316 and 324 mOsm/kg for control media, VS-A and VS-C secretions, respectively. Osmolality for VS-B was not obtained.

Variable Protein Expression in VS Secretions

Figure 19:
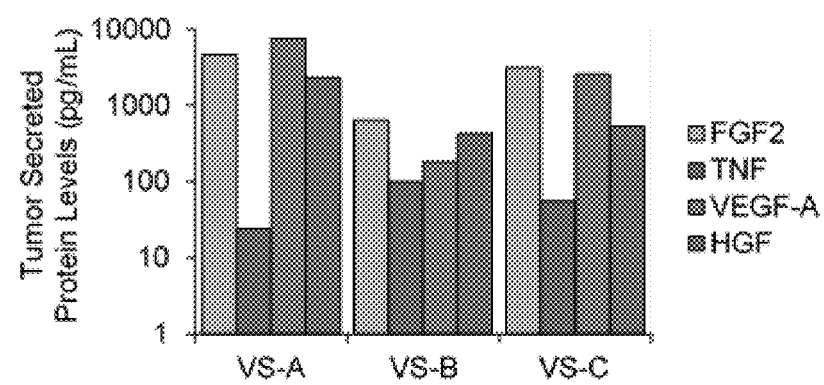
FIG. 19 is the levels of specific molecules in VS secretions. VS secreted fibroblast growth factor 2 (FGF2), tumor necrosis factor alpha (TNFα), vascular endothelial growth factor-A (VEGF-A), and hepatocyte growth factor (HGF) levels secreted from VS-A, VS-B and VS-C.

Four proteins of interest in the context of VS, each discussed in the later examples, were measured in the tumor secretions. FGF2, a known otoprotective cytokine, was found to be 4671, 647, and 3168 pg/mL in VS-A, VS-B, and VS-C respectively (FIG. 19). TNFα, a known ototoxic molecule, was found to be 24, 100, and 56 pg/mL in VS-A, VS-B, and VS-C, respectively (FIG. 19). VEGF-A, a potent angiogenic cytokine, was found to be 7645, 183, and 2579 pg/mL in VS-A, VS-B, and VS-C respectively (FIG. 19). HGF, another potent angiogenic cytokine whose dysfunction leads to hearing loss, was found to be 2312, 431, and 525 pg/mL in VS-A, VS-B, and VS-C respectively (FIG. 19).

Discussion

We show, for the first time, that VS secreted factors can lead to cochlear degeneration. Secretions from different tumors led to different patterns of cochlear damage. VS-C, from a patient with a deaf ear, led to drastic degeneration of the cochlea, including loss of HCs and neurites, with severity increasing from the apical to basal turn. Loss in these particular cell types has been noted due to VS—associated SNHL (Roosli et al., 2012). Further, the SNHL gradient with increasing severity from apex to base is also common in VS patients (Thakur et al., 2012).

It was intriguing that we saw a high level of damage due to VS-C in the span of 2 days and it may be that these secretions are extremely detrimental for cochlea. Since this patient was deaf ipsilaterally, we could not assess retrocochlear dysfunction. Previous studies demonstrate a significant degree of hair cell loss, strial atrophy and neuronal loss in VS patients (Roosli et al., 2012), suggesting that both hair cell loss and neuronal loss could have been present in the patient with VS-C. In contrast, the other two VSs led to more specific and less drastic damage. Secretions from VS-B, from a patient with a moderate SNHL, demonstrated specific significant loss of OHCs in the basal turn, potentially explaining the elevated pure tone average of 40 dB, as OHC dysfunction is thought to lead to 40-60 dB threshold shift in hearing (Liberman et al., 2002). The patient does exhibit a lower than expected WD score according to the audiogram (WD curve not shown), suggesting potential dysfunction of the neural pathway along with HC loss, a pathology that could be explained through neurite loss noted in the apical and basal turn cochlear explant cultures.

The only apparent change with VS-A secretions was fiber disorganization. It was interesting to find that although VS-A and VS-C patients presented with an essentially dead ear, their secretions led to very different changes in the cochlear explants. There could be several reasons for this difference. First, VS-A secretions' induction of significant fiber disorganization could have led to the audiometric results noted (≥100 dB PTA, 0% WD) even if the rest of the cochlear structures are intact. If the fibers are disorganized and dysfunctional, then the information cannot be transmitted from the HCs onto the auditory nerve and therefore the patient cannot hear. In fact, previous work has shown that synaptic loss and disorganization, with no loss of HCs or neurons, can be present in SNHL due to other hearing pathologies, such as Meniere's disease (Nadol, 1988). It would be especially insightful to obtain distortion product oto-acoustic emissions (DPOAEs) for the patient with VS-C to see if the OHCs are preserved and functioning. Second, as the patient with VS-A also had a moderate SNHL contralaterally (34 dB PTA, 84% WD), most likely due to history of noise-exposure, the SNHL ipsilaterally could be entirely due to noise exposure or the noise exposure has made the ear more so susceptible to the VS than in other patients. Hence, we do not observe drastic cochlear damage when we apply the secretions on the cochlear explants but we would if we applied them to a more susceptible inner ear. Third, as our cochlear explants experiments are limited to 48 hours because substantial HC disorganization and migration are noted after 48 hours, these secretions may potentially have a more drastic effect on the patient's cochlea due to differential concentration and longer exposure to the VS secretions in vivo. Fourth, as we do hypothesize that the SNHL due to VS is multifactorial, different VSs could cause SNHL in different ways. The main mechanism behind the SNHL due to VS-A could be more so nerve compression or tumor-associated edema rather the secreted factors whereas for VS-C, it could be mainly due to the secreted factors (Thakur et al., 2012). This is unlikely as VS-A is a smaller tumor than VS-C, assuming that extent of compression is correlated with tumor size. Fifth, the less apparent cochlear damage due to VS-A could also be because the tumor pathobiology has changed overtime, as the VS may be secreting factors that led to hearing deterioration two years ago and now is dependent on other pathways for sustained growth and survival. Osmolality as a potential confounder was eliminated as it did not differ between control media and VS secretions. Osmolality, being approximately 320-325 msOm/kg in the media was near the expected value of 335 mOsm/kg in perilymph (Juhn et al., 1979).

Seeing that applying secretions from different VSs, collected and processed in the same way, led to a range of cochlear damage provides confidence that the degeneration seen is due to the specific molecules present in the secretions rather than due to the paradigm. It will be important to explore this pattern for more tumors, including tumors from patients with good hearing, to more confidently establish the effect of VS secreted factors on cochlear cells. Significantly less drastic cochlear degeneration should be noted for VS patients with good hearing. Further, it may be insightful to employ potentially more sensitive markers of cell death or dysfunction, such as stereocillia organization or cleaved caspase 3 activation, in order to establish the functionality of the cochlear cells in culture. The differential secreted levels of TNFα, VEGF-A, HGF and FGF2 from the tumors highlight the potential complexity of SNHL induced by VS secreted factors.

Conclusion

In this work, we demonstrate cochlear damage due to VS-secreted factors. Different tumors led to different types of damage, as has been noted in previous histological cochlear analyses of patients with untreated VS. Generally, loss of hair cells and neurites was noted, with increasing severity from apical to the basal turn. Our results support the hypothesis that VS-secreted factors can damage cochlear cells, leading to the SNHL noted in VS patients.

Example 7

Role of Vestibular Schwannoma Secreted Tumor Necrosis Factor Alpha in Sensorineural Hearing Loss Tumor necrosis factor alpha (TNFα), a pro-inflammatory cytokine, is a known ototoxic and neurotoxic molecule. Anti-TNFα therapies have shown clinical efficacy against sudden SNHL and autoimmune inner ear disease. Since TNFα is present at aberrantly high levels in VS (Example 2), this example aims to investigate TNFα's role in SNHL in the context of VS secretions. We found that secreted TNFα levels from VS correlated with the degree of hearing loss in patients, suggesting its ototoxic role in the context of VS. As TNFα's effect in the murine cochlea has not been studied previously, recombinant TNFα was applied onto murine cochlear explants. Application of recombinant TNFα led to neurite loss and disorganization in the basal turn of cochlear explant cultures. Further, to specifically study TNFα's role within VS secretions, TNFα in VS secretions was neutralized using a monoclonal antibody before applying the secretions onto the cochlear explants. Neutralization of TNFα in VS secretions seemed to rescue, at least partially, loss of outer hair cells and neurites noted with VS secretions alone. Overall, VS secreted TNFα seems to have an ototoxic and neurotoxic role and could be a promising therapeutic target against VS associated SNHL.

Introduction

After noting damage in cochlear explants with application of VS secreted factors, we attempted to elucidate the role of specific factors present in the secretions. Previously studying the role of inflammation-associated molecules in VS growth (NF-kB in Example 2 and COX-2 in Example 3), we now aimed to explore the role of a VS-secreted inflammatory molecule in SNHL. TNFα, a cytokine generally involved in systemic inflammation and an inducer of NF-κB, has been implicated in SNHL due to meningitis (Amnipour, Tinling, and Brodie, 2005) and auto-immune inner ear disease (AIED) (Lobo et al., 2013), and anti-TNFα therapies are emerging against SNHL due to these pathologies. Specifically, use of antibodies targeting TNFα or its receptor TNFR, either through subcutaneous or intratympanic administration, had led to hearing stabilization or improvement in a significant portion of patients with AIED (Lobo et al., 2013). Further, anti-inflammatory glucocorticosteroids are effective in restoring hearing in patients with sudden SNHL or AIED (Wilson, Byl, and Laird, 1980). Since TNFα was found to be present at significantly higher levels in VS in our work (Example 2), we aimed to test its potential role in SNHL in the context of VS.

We found that secreted TNFα levels correlated with VS patients' degree of SNHL in the ipsilateral ear. We also causatively explored the role of TNFα by treating cochlear explant cultures with recombinant TNFα or TNFα-neutralized VS secretions (using a neutralization antibody against TNFα). TNFα application led to detectable neurite loss and disorganization, with most severe effects in the basal turn. Additionally, TNFα neutralization in VS secretions led to rescue of outer hair cell loss and, partially, neurite loss and disorganization originally seen with VS secretions alone.

In this example, we attempted to understand the role of TNFα in SNHL due to VS through direct application of TNFα and neutralization of TNFα in VS secretions.

Methods

VS Secretion Collection

The same methodology as described in Example 6 was utilized.

Cochlear Explants and VS Secretion Application

The same methodology for cochlear explant cultures as described in Example 5 was utilized. The same methodology for VS secretion application as described in Example 6 was utilized. Results for VS-B secretion application are from the same experiments as described in Example 6. VS-B was chosen as it secreted the highest level of TNFα among the tumors tested.

Enzyme-linked Immunosorbent Assay (ELISA)

TNFα was measured in VS secretions, collected in PBS by incubating a fresh tumor specimen for 1 hour at 37° C. (0.01 g/100 μL PBS). Success of TNFα neutralization was confirmed using ELISA (R&D systems) and manufacturer's protocols were followed.

TNFα Application and Neutralization

Recombinant human TNFα (R&D Systems), diluted in culture media to a 5 μg/mL concentration, was applied to cochlear explants for 48 hours. Control cochlear explants received the same volume of PBS in the media as needed to add recombinant TNFα. The explants were then fixed and the same protocol as outlined in Example 6 was used. VS-B secretions, as described in Example 6, were applied to the cochlear explants. Additionally, TNFα in VS secretions was neutralized by incubating the secretions in affinity purified TNFα polyclonal antibody (R&D Systems) for 2 hours at 37° C. prior to application onto explants. Plain media with TNFα neutralization antibody and VS secretions incubated with only goat immunoglobulins (IgGs) (R&D Systems, MN) were prepared simultaneously as controls.

Results

TNFα Expression Correlates with Degree of Hearing Loss

Figure 20:
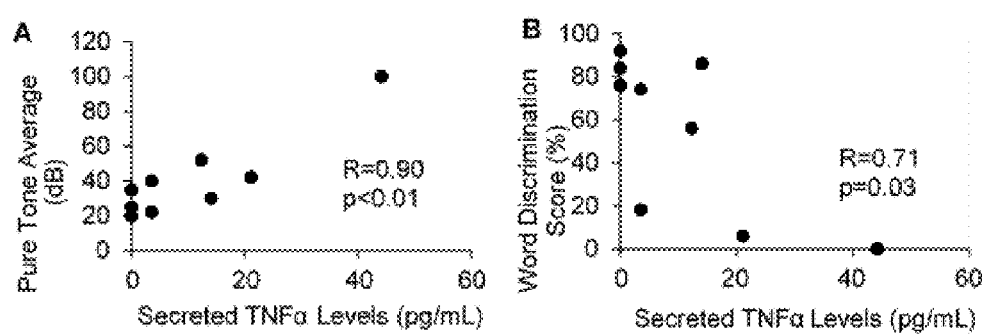
FIG. 20 is the correlation of secreted TNFα levels with VS associated hearing loss. Panels A and B have the same x-axis label. A. TNFα levels present in VS secretions (pg/mL) versus pure tone average (dB) are plotted. B. TNFα levels present in VS secretions (pg/mL) versus word discrimination score (%) are plotted. N=9 for both panels. R and p values for each correlation are embedded within the panel.

TNFα levels were measured in 9 tumor secretions, collected in PBS, using ELISA. The secretions were derived from sporadic VS of patients with varied level of SNHL, with PTA ranging from 20 to 100 dB and WD score ranging from 0 to 92%. TNFα levels, on average being 11.0 pg/mL, had a range of 0.0 to 44.2 pg/mL. TNFα levels in the secretions significantly positively correlated with the patients' PTAs ($R=0.90$, $p<0.01$) and negatively correlated with the WD scores ($R=-0.71$, $p=0.03$) in the ipsilateral ear (FIG. 20). The contralateral ears for all patients had normal hearing.

Morphological and Molecular Changes in Cochlear Explants with TNFα Modulation

Figure 21:
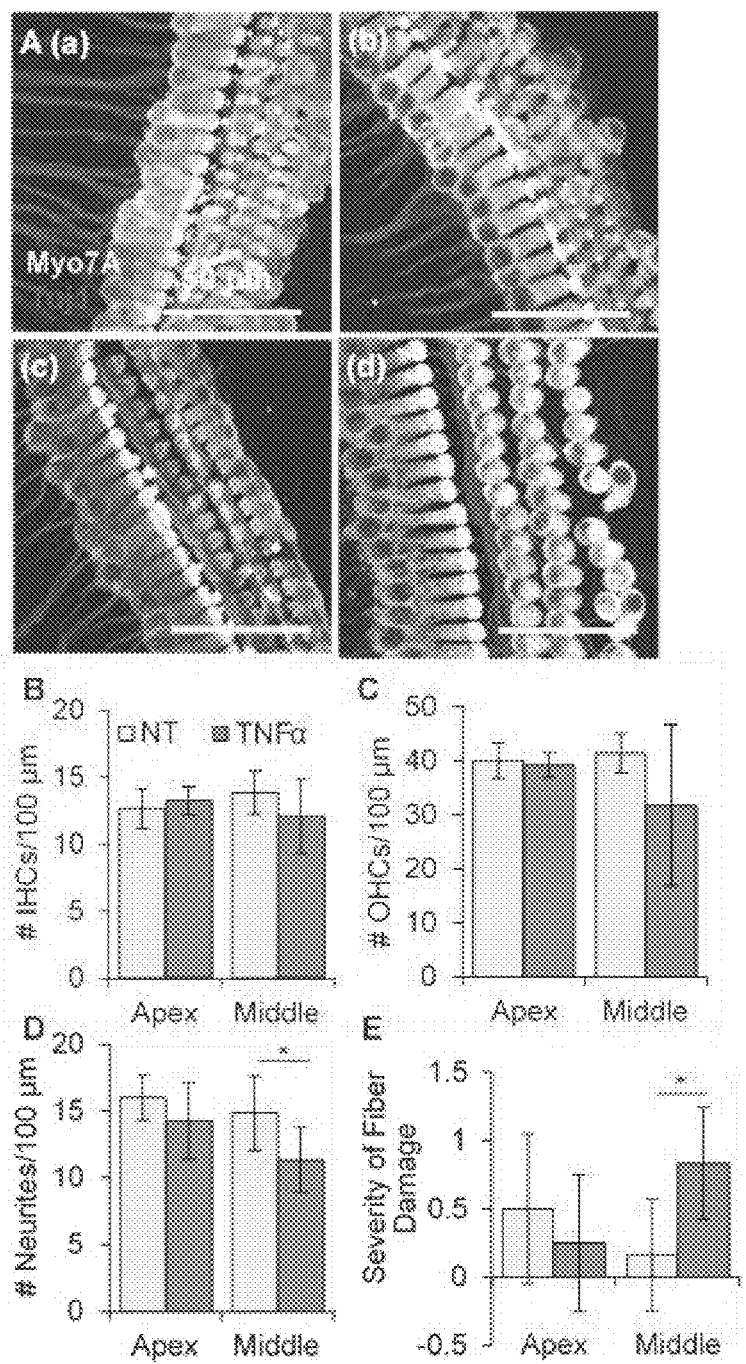
FIG. 21 is demonstrating that the application of TNFα onto cochlear explants leads to neurite loss and disorganization. A. Representative images for cochlear explants receiving no treatment (NT, n=6 different explants, a), incubated with TNFα (n=4 different explants, b) are shown for the apical and NT (n=6 different explants, c) and TNFα (n=6 different explants, d) for the basal turn. Myo7A (green in original) marks hair cells and Tuj1 (red in original) marks neurites. Scale Bar=50 μm applies to all images. B. Number of inner hair cells (IHCs), C. outer hair cells (OHCs), D. neurites E. and severity of fiber damage are shown for a 100 μm length within the apex and basal turn explants for NT (grey columns) and TNFα-treated (red columns). Error bars represent SD. *p<0.05.

Cell counts and morphology of recombinant human TNFα-treated cochlear explants were compared with those of control cochlear explants receiving only PBS (NT). Morphological changes assessed in the cochlear explant after TNFα treatment indicate specific damage to the basal turn. There was significant neurite loss and fiber disorganization in the basal turn after TNFα treatment. Representative images for NT and TNFα-treated apical turn cultures are shown in FIG. 21A (a-b), respectively. Representative images for NT and TNFα-treated basal turn cultures are shown in FIG. 21A (c-d), respectively. Data are summarized as average±SD for NT and TNFα-treated cochlear explants.

N represents the number of cochlear explant cultures tested for a given treatment. The number of IHCs per 100 μm length along the cochlea did not change, going from 12.6±1.5 for NT (n=6 different explants) to 13.2±1.0 for TNFα-treated (n=4 different explants) in the apical (p=0.52) and 13.8±1.6 for NT (n=6) to 12.1±2.8 to TNFα-treated (n=6 different explants) in the basal turn (p=0.21) (FIG. 21B). N for each group is same as for IHCs for all further analyses. The number of OHCs did not change, going from 40.1±3.3 to 39.1±2.2 in the apical turn (p=0.21); although the number tended to decrease in the basal turn, this did not meet significance, going from 41.4±3.6 to 31.8±14.9 in the basal turn (p=0.15) (FIG. 21C). The number of neurites went from 16.0±1.7 to 14.3±2.9 in the apical (p=0.25) and 14.8±2.8 to 11.3±2.4 in the basal turn (p=0.04) (FIG. 21D). The severity of the fiber disorganization, assessed qualitatively with 0 being essentially intact and 2 being most severe, changed from 0.5±0.5 to 0.2±0.5 in the apical (p=0.49) and 0.2±0.4 to 0.8±0.4 in the basal turn (p=0.02) (FIG. 21E). The large variability present in the all the measures could have led to inability to detect significance in some cases. Osmolality did not deviate from control media, being 330 and 329 mOSm/kg for control media and media with recombinant TNFα, respectively.

Damage to the Basal Turn of Cochlear Explants Due to VS Secretions can be Partially Rescued by TNFα Neutralization VS-B secretions were chosen to study TNFα's role as VS-B secreted the most TNFα (99.6 pg/mL) out of the VS tested (Example 6). Applying VS-B secretions to the cochlear explants led to significant loss of OHCs, specifically in the basal turn, and neurite loss in both apical and basal turns. Additionally, fibers were significantly disorganized in the apex. The effect of TNFα in these secretions was assessed by neutralizing TNFα in the secretions before applying them to the cochlear explants. Neutralization was verified through ELISA. Human TNFα level was 17.6 pg/mL in prepared cochlear explant media containing VS secretion incubated with goat IgGs versus 3.7 pg/mL after incubating the media with the TNFα neutralization antibody for 2 hours. TNFα neutralization of VS secretions led to a significant rescue of the OHC loss, and a trend of restored neurites and fiber organization in the basal turn.

Figure 22:
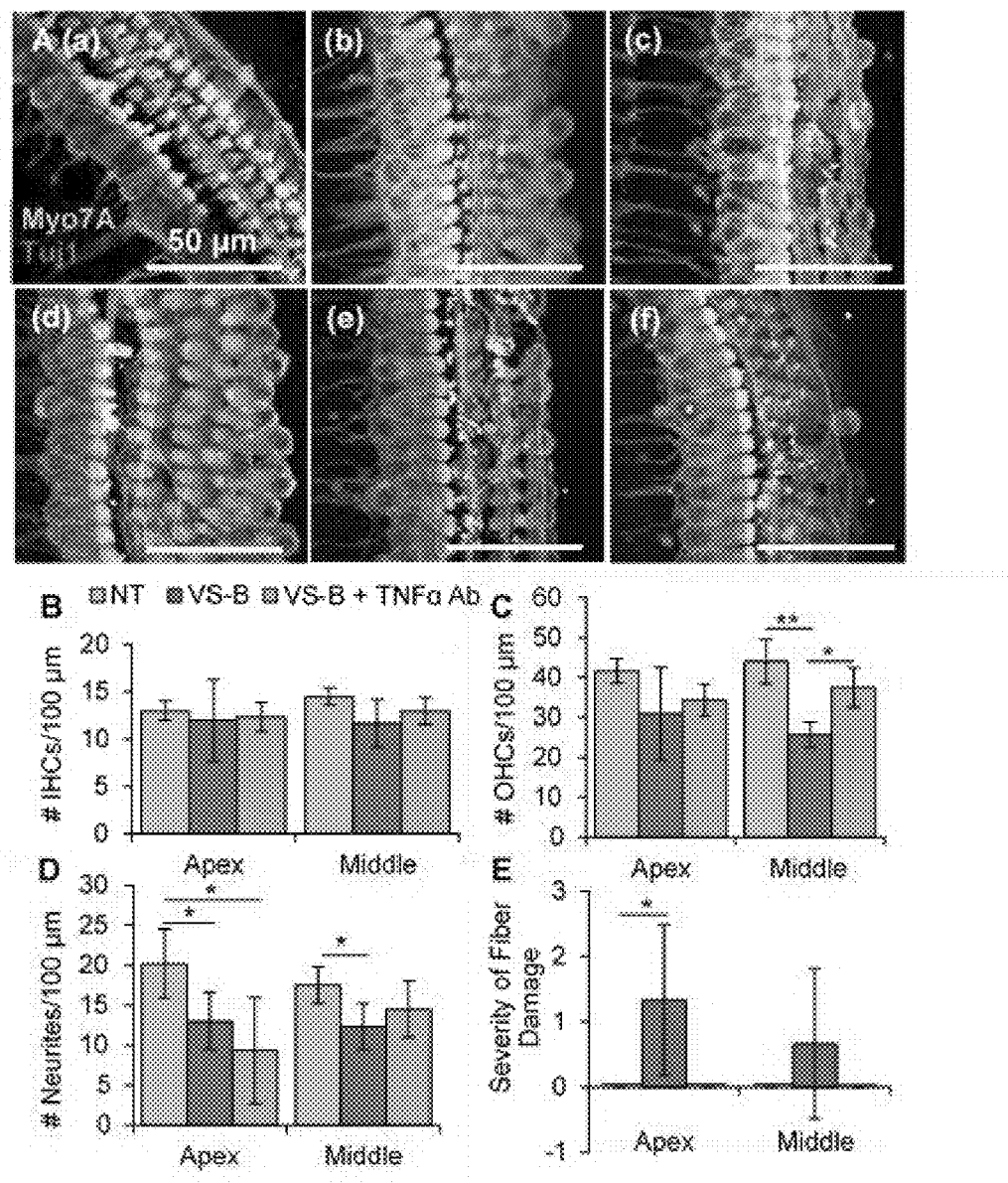
FIG. 22 is illustrating that TNFα neutralization in VS secretions partially rescues cochlear damage due to VS secretions alone. A. Representative images for cochlear explants receiving no treatment (NT, a), incubated with VS-B secretions (n=3 different explants, b) and with VS-B secretions with TNFα neutralization (n=3 different explants, c) are shown for the apical and NT (d) and VS-B secretions (n=3 different explants, e) and with VS-B secretions with TNFα neutralization (n=2 different explants, f) for the basal turn. Myo7A (green) marks hair cells and Tuj1 (red) marks neurites. Scale Bar=50 μm applies to all images. B. Number of IHCs, C. OHCs, D. neurites and E. severity of fiber damage are shown for a 100 μm length within the apex and basal turn explants for NT (grey columns), VS-B secretions alone (red columns), TNFα-neutralized VS-B secretions (green columns). Error bars represent SD. *p<0.05, **p<0.01.

Representative images of the apical turn cultures for NT, VS-B secretions alone and TNFα-neutralized VS-B secretions are shown in FIG. 22A (a-c), respectively. Representative images of the basal turn cultures for NT, VS-B secretions alone and TNFα-neutralized VS-B secretions are shown in FIG. 22A (d-f), respectively. Data are summarized as average±SD for treatment with VS-B secretions alone and TNFα-neutralized VS-B secretions. N represents the number of cochlear explant cultures tested for a given treatment. P-values are given for TNFα-neutralized VS-B secretions in comparison to NT and in comparison to VS secretion alone, respectively. Specifically, the number of IHCs per 100 μm length did not change, going from 12.0±4.4 (n=3 different explants) to 12.3±1.5 in the apical (n=3 different explants, p=0.48 in comparison to NT and 0.91 in comparison to VS secretion alone) and from 11.7±2.5 (n=3 different explants) to 13.0±1.4 in the basal turn (n=2 different explants, p=0.19 in comparison to NT and 0.56 in comparison to VS secretion alone) after TNFα neutralization of VS-B secretions (FIG. 22B). N is the same in the rest of analyses as for IHC counts. The number of OHCs per 100 μm length increased, going from 23.6±12.0 to 34.3±4.0 in the apical turn (p=0.03 in comparison to NT and 0.66 in comparison to VS secretion alone) and from 16.3±6.9 to 37.5±5.0 in the basal turn (p=0.28 in comparison to NT and 0.04 in comparison to VS secretion alone) (FIG. 22C). The number of neurites per 100 μm length changed, going from 13.0±3.6 to being 9.3±6.7 present in the apical (p=0.03 in comparison to NT and 0.45 in comparison to VS secretion alone) and from 12.3±2.9 to 14.5±3.5 present in the basal turn (p=0.30 in comparison to NT and 0.50 in comparison to VS secretion alone) (FIG. 22D). The severity of fiber damage per 100 μm length changed, as assessed qualitatively, reduced substantially, going from 1.3±1.2 to being 0.0±0.0 present in the apical turn and from 0.7±1.2 to 0.0±0.0 present in the basal turn (FIG. 22D). Although the efferent fiber organization returned to being intact with TNFα neutralization, significance testing could not be conducted due to the small sample numbers (FIG. 22E).

Discussion

We found, for the first time, that TNFα may play a role in SNHL due to VS. The robust correlation found between TNFα levels and degree of SNHL, in terms of PTA and WD, provide a strong motivation to understand the role of TNFα in SNHL due to VS, especially as TNFα is known to cause hearing loss in other etiologies. We studied its role through the use of murine cochlear explants. Similar to VS secretions causing more severe damage in the basal turn in comparison to the apical turn (Example 6), TNFα seems to induce damage in IHCs and fibers specifically in the upper basal turn. Applying TNFα onto the cochlear explants did not induce severe damage as has been described previously when applying TNFα at the given concentration (1 μg/mL) to rat cochlear explants (Dinh et al., 2008). This is most likely because we did not culture the lower most basal turn near the hook region, where Dinh et al. noted most of the damage. We also cultured the cochlear explant intact with neuronal connections versus only the organ of Corti, as done by Dinh et al., and the neural connections could provide growth factors and protective molecules for the organ of Corti. Differences in our and Dinh et al. results could also be due to variability in species susceptibility (mouse vs. rat) or due to the fact that we used TNFα from a different species than the derived cochlear explants. Human TNFα was utilized as the VS secretions contain human TNFα, providing us a more so direct comparison between the two experiments. Nonetheless, consistent with Dinh et al., we also saw more severe damage towards the basal turn, i.e. upper basal turn, in comparison to the apical turn.

Application of tumor secretions from a VS patient with moderate hearing loss led to OHC loss in the basal turn and neurites loss and fiber disorganization in the apical and basal turns. Intriguingly, TNFα neutralization in these secretions seemed to completely rescue the loss of OHC damage and partially rescue the loss of neurites and fiber disorganization only in basal turn. This patient did not respond to steroid therapy for her sudden SNHL. In our experiments, we noted rescue of HC loss, suggesting that anti-TNFα therapy may have been beneficial. Although not currently clear, there could be a patient population that does not respond to steroid therapy but does respond to specific anti-TNFα therapy. Interestingly, although we did not note HC loss expected due to TNFα treatment, we did see rescue of OHC loss after TNFα neutralization in VS secretions, more so in concurrence with Dinh et al.'s findings.

Our observations are also in accord with, although less dramatic than, the findings that TNFα neutralization was able to ameliorate meningitis-induced loss of organ of Corti, neurons and spiral ligament in gerbils (Amnipour et al., 2005). In our model, TNFα antibody was able to rescue most of the damage only in the basal turn, whereas Amnipour et al. found that TNFα antibody led to significantly less damage in all regions of the cochlea in all cell types analyzed. This provides insight into the potentially more complex mechanism of SNHL due to VS where several molecules could be involved and have differential roles in different regions of the cochlea. In this particular case, VS-B's induction of OHC and neurite loss in the basal turn could be due to TNFα, which was rescued by its neutralization; another molecule or mechanism could be responsible for the neurite loss in the apical turn. This localization of TNFα's effect is consistent with previous work (Dinh et al., 2008) and our results showing TNFα affecting the basal and basal regions of the cochlea.

Our work suggests that, at least for some tumors, anti-TNFα therapy may be beneficial in reducing hearing loss due to VS. Although we used an anti-human TNFα antibody to neutralize TNFα, it is possible that murine TNFα was also neutralized due to homology between the two proteins. Therefore, it is not clear whether this effect was due to solely neutralization of TNFα present in the secretions or potentially neutralization of TNFα that may be secreted by the cochlear explants in response to VS secretions. In an adult murine cochlea, TNFα seems to be only produced by fibrocytes in the spiral ligament, a portion of the cochlea not present in our cultures, but TNFα expression has not been defined for neonatal cochlear explants. As only one tumor was tested, more experiments are needed for a more conclusive result, and to understand whether TNFα therapy would be beneficial for all VS patients with SNHL or only ones whose tumors secrete high levels of TNFα. Since anti-TNFα therapies have demonstrated some success for other types of SNHL with minimal side effects, our work indicates a new potential use of this class of drugs.

Previously, we have shown that NF-kB inhibition leads to decrease in VS growth and survival (Example 2). It may be that inhibition of TNF, a major inducer of NF-kB, could also be effective against VS growth. In that case, systemic administration of a clinically-tested TNFα antibody such as infliximab would be an effective pharmacotherapy against VS as it would target VS growth and SNHL due to VS, potentially similarly effective as VEGF inhibition by bevacizumab. If TNFα inhibition does not prove to be effective against VS, intratympanic administration of anti-TNFα therapy could be an appealing alternative to avoid systemic effects.

Conclusion

In this example, we establish the potential of TNFα-induced cochlear damage independently and in the context of VS secretions. Recombinant TNFα led to neurite loss and disorganization in the basal turn of cochlear explant cultures. Neutralization of TNFα in VS secretions rescued, at least partially, loss of OHCs and neurites noted with VS secretions alone. Our results are consistent with previous findings demonstrating TNFα as an ototoxic molecule in other pathologies leading to SNHL.

Example 8

Role of Vestibular Schwannoma Secreted Vascular Endothelial Growth Factor in Sensorineural Hearing Loss Along with VS growth, VEGF-A has been implicated in VS-associated SNHL because bevacizumab led to independent radiological decrease in tumor volume and improved hearing in patients with NF2 VSs (Plotkin et al., 2009; 2012). This finding suggests that VEGF-A has a role in VS-associated SNHL independent from its effect on VS growth; the underlying mechanism is unknown. More generally, VEGF-A's role in hearing is largely unknown; it may be ototoxic or otoprotective in different contexts. Here, VEGF-A's role was causatively explored by applying recombinant VEGF-A to cochlear explant cultures. Additionally, to study VEGF-A's role in SNHL in the context of VS secretions, cochlear explant damage was assessed after treatment with VS secretions with or without VEGF-A neutralization. Overall, VEGF-A application or VEGF-A neutralization in VS secretions did not lead to any significant changes. Interestingly, seemingly in contrast to findings in Example 4 demonstrating direct cross-talk between VEGF-A and HGF signaling pathways in SC and VS cells, VEGF application and neutralization led to decreased and increased HGF levels, respectively, in the cochlear explant cultures.

Introduction

Along with VS growth, VEGF-A signaling has been implicated in VS-associated SNHL because modulation of VEGF-A signaling with bevacizumab led to independent radiological reduction in tumor volume and improved hearing in patients with NF2-associated VS (Plotkin et al., 2009; 2012). It may be that VEGF-A secreted from VS could be triggering activation of VEGF-A signaling in the cochlea, leading to degeneration of the inner ear. Anti-VEGF-A therapy could be rescuing this cell damage and restoring function, leading to improved hearing in VS patients. VEGF-A and its receptors are detected in the stria vascularis, organ of Corti, and spiral ganglion neurons (Picciotti et al., 2004). VEGF-A has an unclear role in hearing: it is upregulated in neurons after noise-mediated SNHL (Picciotti et al., 2006) and vibration-induced SNHL (Zou et al., 2005) but is downregulated with aging (Picciotti et al., 2004). We more causatively explored the role of VEGF-A by treating cochlear explant cultures with recombinant VEGF-A or VEGF-A-neutralized VS secretions (using a neutralization antibody against VEGF-A). VEGF-A application did not lead to detectable hair cell or neurite loss. Additionally, VEGF-A neutralization in VS secretions could not rescue the hair cell or neurite loss due to VS secretions alone, although there was a trend of increased neurite counts.

Along with exploring cross-talk between VEGF-A and HGF signaling previously in VS and SC cultures (Example 4), we now attempt to understand the potential cross-talk between VEGF-A and HGF present in cochlear cells, particularly since mutations in HGF lead to an autosomal-recessive, nonsyndromic HL in humans, and both over- and under-expression of HGF result in deafness (Schultz et al., 2009). Interestingly, we found that VEGF-A application onto the cochlear explants led to decreased HGF secretion, and VEGF-A neutralization in VS secretions led to a further increase in HGF secretion. Further, HGF application onto cochlear explants has been shown to rescue HC loss induced by aminoglycosides (Kikkawa et al., 2009). This suggests that VEGF-A and HGF may have an inverse relationship in the cochlea, seemingly opposite of the trend noted in VS and SCs in Example 4.

In this example, we explored the role of VEGF-A, independently, and in the context of VS secretions, in modulating cochlear cell damage. We also investigated VEGF-A's ability to modulate HGF levels.

Methods

VS Secretion Collection

The same methodology as described in Example 5 was utilized.

Cochlear Explants and VS Secretion Application

The same methodology for cochlear explant cultures and VS secretions as described in Example 6 was utilized. Results for VS-C secretion application are from the same experiments as described in Example 6.

Immunofluorescence and Imaging

The same methodology as described in Example 6 was utilized.

VEGF-A Application and Neutralization

Recombinant human VEGF-A (R&D Systems), diluted in culture media to a 5 μg/mL concentration, was applied to cochlear explants for 48 hours. The explants were fixed and the same protocol as outlined previously was followed (Example 6). VEGF-A in VS secretions was neutralized by incubating the secretions in affinity purified polyclonal antibody (R&D Systems) for 2 hours at 37° C. prior to application onto explants. Plain media with neutralization VEGF-A antibody and VS secretions incubated with only goat IgGs (R&D Systems, MN) were prepared simultaneously as controls. Success of VEGF-A neutralization was confirmed using ELISA.

Enzyme-linked Immunosorbent Assay (ELISA)

Human VEGF-A ELISA and mouse HGF ELISA kits were purchased from R&D systems and manufacturer's protocols were followed.

Results

VS-secreted VEGF-A Levels Correlate with the Ipsilateral Ear's WD Score

Figure 23:
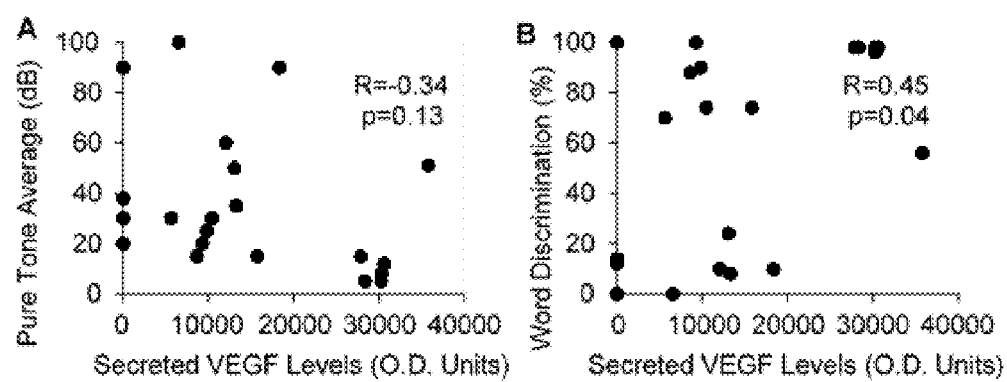
FIG. 23 is the correlation of secreted VEGF-A levels with VS-associated SNHL. A. VEGF-A levels present in VS secretions (O.D. units) versus PTA (dB) are plotted. B. VEGF-A levels present in VS secretions (O.D. units) versus WD score (%) are plotted. n=21 for both panels. R and p values for each correlation are embedded within the panel.

When secreted VEGF-A levels were measured in VS as shown in Example 4, its secretion level was correlated with the hearing status of the patients (n=21). Interestingly, although VEGF-A levels in VS did not correlate with the PTA of patients with VS ($R=0.34$, $p=0.13$, FIG. 23A) or with tumor size ($R=0.03$, $p=0.89$), they did significantly positively correlate with the patient's WD score in the ipsilateral ear ($R=0.45$, $p=0.04$, FIG. 23B). The correlation, albeit meeting our criteria for significance, demonstrates significant spread in data.

Morphological and Molecular Changes in Cochlear Explants with VEGF-A Modulation

To explore VEGF-A's effect on the cochlea, we assessed HC and neurite loss and fiber disorganization in cochlear explant cultures treated with recombinant VEGF-A.

Figure 24:
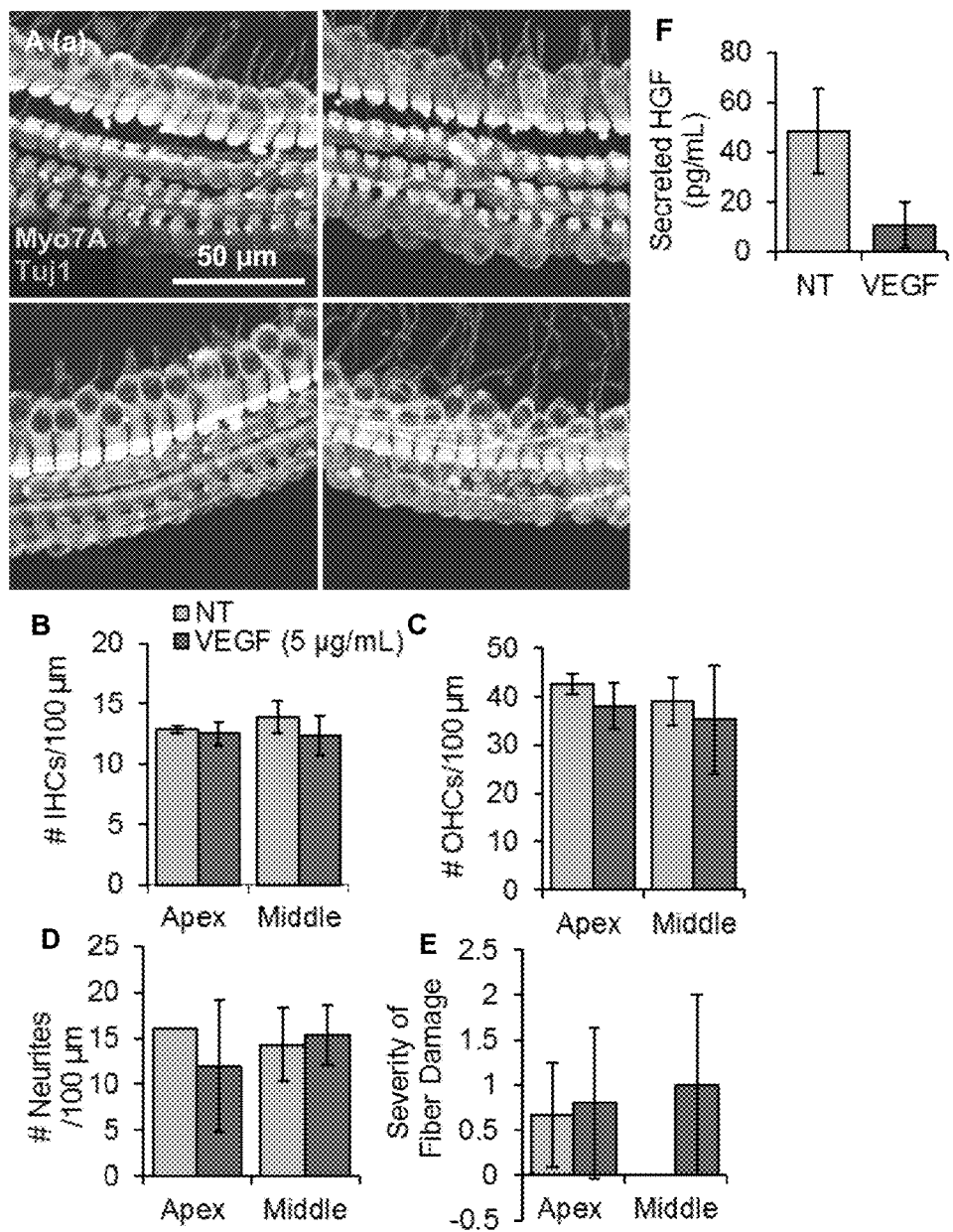
FIG. 24 is demonstrative VEGF-A application onto cochlear explant does not induce significant damage. A. Representative images for cochlear explants receiving no treatment (NT, n=3 different explants, a), incubated with VEGF-A (n=5 different explants, b) are shown for the apical and NT (n=4 different explants, c) and VEGF-A (n=3 different explants, d) for the basal turn. Myo7A (green in original) marks hair cells and Tuj1 (red in original) marks neurites. Scale Bar=50 μm applies to all images. B. Number of IHCs, C. OHCs, D. neurites and, E. severity of fiber damage are shown for a 100 µm length within the apical and basal turn explants for NT and VEGF-A-treated. F. Secreted murine HGF levels in cochlear explants for NT (n=4 different explants) and after VEGF treatment (n=4 different explants). Error bars represent SD. *p<0.05.

No significant HC or neurite loss was noted, although there was a trend of decreased number of OHCs in the apical and basal turns. Representative projection images of untreated apical and basal turns and VEGF-A-treated apical and basal turns are shown in FIG. 24A (a-d), respectively. Data are summarized as average±SD for NT and VEGF-A-treated cochlear explants. N represents the number of cochlear explant cultures tested for a given treatment. The number of IHCs per 100 μm length along the cochlea did not change, going from 12.8±0.3 for non-treated (n=3 different explants) to 12.5±1.0 for VEGF-treated (n=5 different explants) in the apical (p=0.60) and 13.9±1.3 for non-treated (n=4 different explants) to 12.3±1.6 for VEGF-treated (n=3 different explants) in the basal turn (p=0.22) (FIG. 24B). N for each group is same as for IHCs for all further analyses. The number of OHCs reduced from 42.7±2.0 to 38.1±4.8 in the apical (p=0.17), and 39.0±4.8 to 35.3±11.2 in the basal turn (p=0.29) (FIG. 24C). The number of neurites generally decreased in the apical turn from 16.0±0.0 to 12.0±7.2, although not meeting significance (p=0.38), and did not change in the basal turn, going from 14.3±4.0 to 15.3±3.2 (p=0.75) (FIG. 24D). The severity of fiber damage, assessed qualitatively with 0 being essentially intact and 2 being most severe, did not change significantly, going from 0.7±0.6 to 0.8±0.8 in the apical (p=0.82) and 0.0±0.0 to 1.0±1.0 in the basal turn (p=0.16) (FIG. 24E).

To understand VEGF-A and HGF's relationship in cochlear cells, HGF levels were measured after VEGF-A treatment. Basal secreted HGF levels were 48.1±17.0 pg/mL in control cochlear explants (n=4 different explants, FIG. 24F). Interestingly, treating cochlear explants with 5 μg/mL recombinant human VEGF-A for 48 hours led to significantly lower levels of HGF, being 10.5±9.4 pg/mL (n=4 different explants, p=0.01, FIG. 24F). This change was specific to VEGF-A as incubating the cochlear explants with the same concentration of TNFα did not lead to changes in the secreted HGF levels (n=3 different explants, p=0.40). Osmolality did not deviate from control media, being 330 mOSm/kg for both control media and media with recombinant VEGF-A.

Damage to Cochlear Explants Due to VS Secretions could not be Rescued by VEGF-A Neutralization Treating cochlear explants with secretions collected from VS from a patient with severe SNHL (VS-C) led to significant cochlear degeneration, with greater loss in the basal turn. Results for VS-C secretion application are from the same experiments as described in Example 6. The effect of VEGF-A in these secretions was assessed by neutralizing VEGF-A in the secretions before applying them to the cochlear explants. Neutralization was verified through ELISA. VEGF-A levels, originally 3332.8±305.6 pg/mL in VS secretions, decreased to an undetectable level after incubating the secretions with the neutralization antibody for 2 hours. VEGF-A neutralization in the secretions had a trend, albeit not significant, to rescue the neurite loss at the apical turn but did not change the level of other cell loss or damage.

Figure 25:
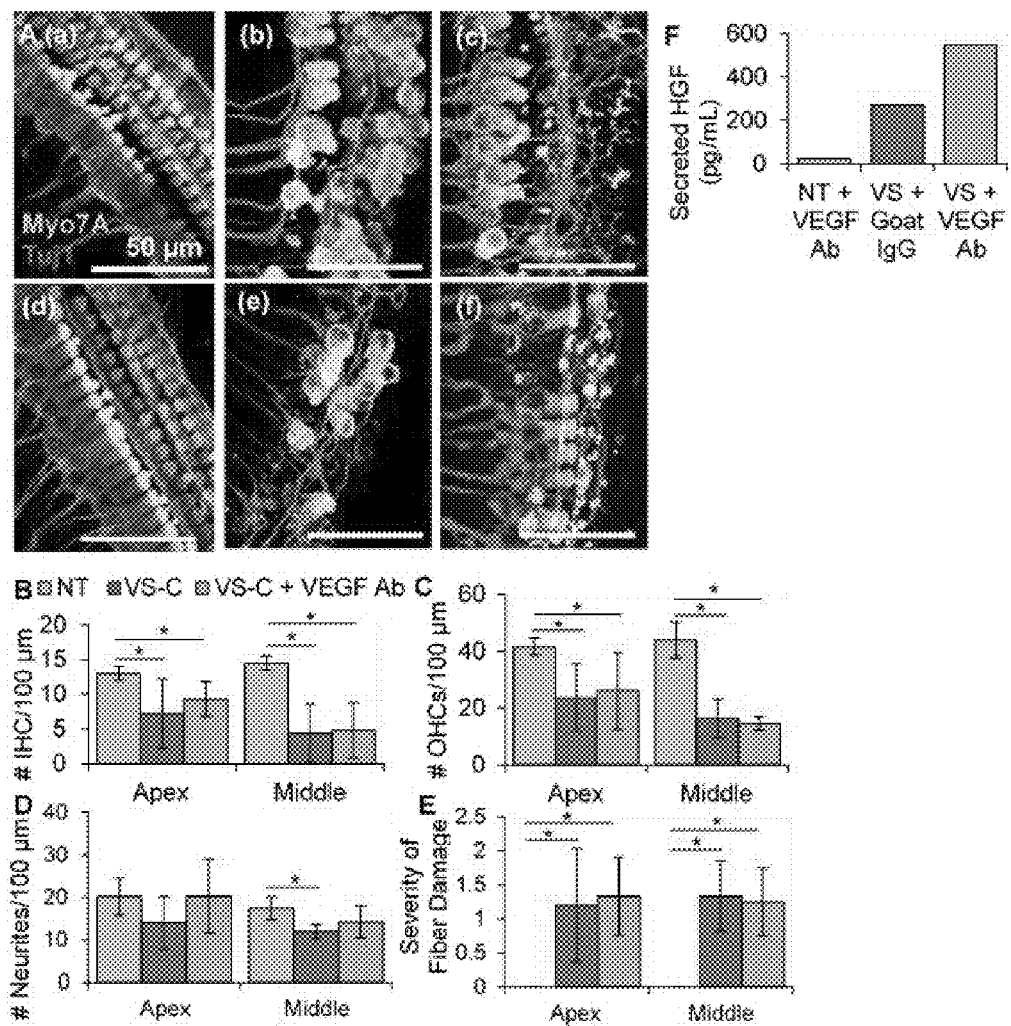
FIG. 25 is illustrative that VEGF-A neutralization in VS secretions partially rescues cochlear damage due to VS secretions alone. A. Representative images for cochlear explants receiving no treatment (NT, a), incubated with VS-C secretions (n=5 different explants, b) and with VS-C secretions with VEGF-A neutralization (n=3 different explants, c) are shown for the apical and NT (d) and VS-C secretions (n=6 different explants, e) and with VS-C secretions with VEGF-A neutralization (n=4, f) for the basal turn. Myo7A (green in original) marks hair cells and Tuj1 (red) marks neurites. Scale Bar=50 µm applies to all images. B. Number of IHCs, C. OHCs, D. neurites and, E. severity of fiber damage are shown for a 100 µm length within the apex and basal turn explants for NT (grey column), VS-C secretions alone (red columns), VEGF-A-neutralized VS-C secretions (green columns). F. Secreted murine HGF levels in cochlear explants receiving NT, VS-C alone or VS-C secretions with VEGF-A neutralization.*p<0.05, **p<0.01.

Representative projection images are given of untreated, VS-C secretion treated and VEGF-A-neutralized VS-C secretion treated apical turn in FIG. 25A (a-c), respectively, and untreated, VS-C secretion treated and VEGF-A-neutralized VS-C secretion treated basal turn in FIG. 25A (d-f), respectively. Data are summarized as average±SD for VS-C secretion treated and VEGF-A-neutralized VS-C secretion treated cochlear cultures. N represents the number of cochlear explant cultures tested for a given treatment. Specifically, the number of IHCs per 100 μm length did not change, going from 7.2±5.1 for VS secretions alone (n=5 different explants) to 9.3±2.5 for VEGF-A-neutralized VS secretions in the apical (n=3 different explants, p=0.02 in comparison to NT and 0.53 in comparison to VS secretion alone) and from 4.3±4.2 for VS secretions alone (n=6 different explants) to 4.7±4.0 for VEGF-neutralized VS secretions in the basal turn (n=4 different explants, p<0.01 in comparison to NT and 0.88 in comparison to VS secretion alone) (FIG. 25B). N is the same as rest of the analyses as for IHC counts. The number of OHCs did not change, going from 23.6±12.0 to 26.0±13.5 in the apical (p=0.04 in comparison to NT and 0.80 in comparison to VS secretion alone) and from 16.3±6.9 to 14.5±2.4 in the basal turn (p<0.01 in comparison to NT and 0.62 in comparison to VS secretion alone) (FIG. 25C). The neurite loss demonstrated a trend towards partial rescue with VEGF-A neutralization, going from 14.0±6.2 to 20.3±8.7 present in the apical (p=0.97 in comparison to NT and 0.27 in comparison to VS secretion alone) and 12.0±1.7 to 14.3±3.8 present in the basal turn (p=0.28 in comparison to NT and 0.27 in comparison to VS secretion alone); this trend did not meet significance (FIG. 25D).

The average neurites for the apical and basal turns with NT were 20.2±4.3 and 17.5±2.7, suggesting that VEGF neutralization was able to restore the average in the apical turn, although the difference with and without VEGF-A neutralization did not reach significance. The severity of fiber damage, assessed qualitatively, remained high, going from 1.2±0.8 to 1.3±0.6 in the apical (p<0.01 in comparison to NT and 0.81 in comparison to VS secretion alone) and from 1.3±0.5 to 1.3±0.5 in the basal turn (p<0.01 in comparison to NT and 0.81 in comparison to VS secretion alone) (FIG. 25E).

Additionally, treatment with VS secretions increased secreted HGF levels to 270.6 pg/mL in the cochlear explants (FIG. 25F). Interestingly, VEGF-A neutralization further increased secreted HGF levels to 548.3 pg/mL in the cochlear explants (FIG. 25F). This is consistent with the pattern that incubation with cochlear explants with VEGF-A leads to decreased HGF levels.

Discussion

In this work, VEGF-A does not seem to play a major role in cochlear damage, aside from potential neurite loss in the apical turn. Previous studies show VEGF-A expression changes are induced by cochlear insults (Zou et al., 2005; Picciotti et al., 2006). For example, increased cochlear VEGF-A expression was observed in noise-exposed guinea pigs throughout many different cell types, including the stria vascularis and spiral ganglion neurons (Picciotti et al., 2006). Increased VEGF-A expression in cochlea after vibration induced SNHL has also been noted in guinea pigs (Zou et al., 2005). Additionally, Picciotti et al. found decreased VEGF-A expression in mice with presbycusis (Picciotti et al., 2004). Due to only correlative studies for cochlear insults other than in NF2 VS patients with anti-VEGF-A therapy, it is not clear whether VEGF-A is serving an otoprotective or ototoxic role in these settings (London and Gurgel, 2013). In our study, we could not confidently decipher whether our results are due to the fact that VEGF-A does not cause any damage in the cochlea or because of inadequacies of the model. Further, it is possible that VEGF-A could have a pathologic or beneficial role depending upon the context. It was interesting to note that sporadic VS secreted VEGF-A levels positively correlated with the ipsilateral ear's WD score, opposite of what would be expected given the clinical data showing that anti-VEGF-A therapy improves WD. Our findings may be in line with previous findings that have shown VEGF-A as a neuroprotective molecule (Sondell, Lundborg, and Kanje, 1999) but not otoprotective since VEGF-A was not found to rescue gentamicin-induced HC death (Monge, Gasmann & Bodmer, 2009). In VS patients whose hearing improved with bevacizumab treatment, the authors only detected changes in WD, suggesting that the improvement may be due to changes in neuronal function. Intriguingly, the only trend of decrement with VEGF-A treatment and improvement after VEGF neutralization in VS secretions is neurite loss, most drastic in the apical turn. It could be that VEGF inhibition is minimizing neurite degeneration and rescuing neurite function in these patients, leading to the noted improvements in WD scores, as WD scores correlate with neuronal and neurite innervation density (Pauler, Schuknecht & Thornton, 1986). The finding that VEGF-A seems to be acting more so in the apical turn reinforces this hypothesis as frequencies needed for speech processing (0.2-5 KHz) would be present within and near the apical region in humans. It will be important to have larger sample sizes of cochlear explants in future work to counter the large inherent variability present among the cochlear explants. As we did not assess neuronal loss, it is not clear whether spiral ganglion neuron health was affected by these treatments, another aspect that would be important to explore in the future.

Nonetheless, the lack of an effect of VEGF-A in our work could be for several reasons. First, it could be that sporadic VS, as tested in our current study and NF2 VS have different mechanisms of HL and roles for VEGF-A in HL. This is exemplified by the literature, in that although no studies seem to find a correlation between sporadic VS size and HL (Nadol et al., 1996, Cayé-Thomasen et al., 2007), there are studies that find an association between NF2 VS size and HL (Asthragi et al., 2012). Second, since we did not use any markers for cell death such as cleaved caspase 3 or TUNEL staining, we were only able to assess cell health using morphological changes and cell loss, an assessment that may not be sensitive enough in this model. The reason we used this way of assessment is because we could detect changes post VS-C secretion treatment in Example 5, 6, and 7. Third, our model may not be representative of a human adult cochlea as we are using a postnatal murine cochlear explant. There could be a difference in species (mouse versus human) susceptibility, in which the murine cochlea does not respond to VEGF-A as a human cochlea or that human VEGF-A may not have a strong affinity to murine VEGF-A receptors, failing to induce a strong response. Further, differences in age (neonatal versus adult) could lead to a neonatal cochlea being differentially and potentially less susceptible than an adult cochlea, as a neonatal cochlea has very different gene expression than in adult (Tadros et al., 2014). Unfortunately, it is not possible to culture an adult cochlea using current methods. Fourth, rescue by VEGF-A inhibition could require a longer time period than 48 hours. We could only incubate the cochlear explants with VEGF-A or VS secretions for 2 days as longer time periods led to disorganization and migration of the HCs in cultures. In contrast, VS-induced SNHL in humans can range from sudden SNHL to gradual SNHL spanning several decades (Thakur et al., 2012). Further, bevacizumab therapy's effect on HL was noted in most patients after 8 weeks (Plotkin et al., 2012).

Fifth, it is also possible that anti-VEGF-A treatment associated hearing improvement is independent of VEGF-A's direct role in the cell health but potentially through an indirect role such as relieving edema in the cerebellopontine angle and internal auditory canal. Plotkin et al. (2009, 2012) suggest a normalization of vasculature or decompressing of the auditory nerve as a potential explanation for hearing improvement. Sixth, it may be that the mechanism is more complex as suggested by past work (Stankovic et al., 2009; Lysaght et al., 2011; Dilwali et al., 2013). It could be that along with these factors contributing to HL, there are other molecules, such as FGF2, that are otoprotective (Example 5, Dilwali et al., 2013). It will be important to test VEGF-A's role in inducing HL in a larger set of tumors and potentially use different methods such as more sensitive measures of cellular damage.

Intriguingly, VEGF-A seems to alter HGF levels in the opposite direction in the murine cochlear explants as would be expected based on our findings in human SC and VS cultures (Example 3). Specifically, in human SC and VS cultures, VEGF-A knockdown leads to decreased expression of cMET, HGF's receptor, whereas in the cochlear explants, increasing VEGF-A leads to decreased HGF, and decreasing VEGF-A leads to increased HGF. This difference could be because we are focusing on the ligand here, i.e. HGF, rather than its receptor cMET. It could also be that we are altering autocrine signaling (siRNA-mediated) in the human SC and VS cultures whereas in the murine cochlear explants, we are exogenously altering VEGF-A levels. The inverse relationship of HGF and VEGF-A would suggest VEGF-A to be ototoxic based on previous work. It has been shown that application of recombinant HGF to cochlear explant cultures significantly reduced the HC loss induced by aminoglycosides, and that local application of HGF to the round window membrane of guinea pigs attenuates noise-induced HL (Kikkawa et al., 2009). Therefore, increasing HGF levels by VEGF-A inhibition could be otoprotective, potentially the mechanism of hearing improvement with bevacizumab in NF2 VS patients. Nonetheless, based on Schultz et al. showing a therapeutic range for HGF (since under- or over-expression leads to SNHL), HGF levels would have to be modulated carefully for a therapeutic benefit.

Conclusion

Although VEGF-A may have a role in SNHL due to VS, possibly through its modulation of HGF, no major effect of VEGF-A could be identified in our preliminary data using the cochlear explant model and parameters assessed. Interestingly, seemingly in contrast to VEGF and HGF pathway co-regulation noted in human SC and VS cells, VEGF-A application and neutralization led to decreased and increased HGF levels, respectively, in murine cochlear explants.

REFERENCES

Adams J. Clinical implications of inflammatory cytokines in the cochlea: A technical note. Otol Neurotol. 2002; 23(3): 316-22.

Ahmad Z, Brown C M, Patel A K, Ryan A F, Ongkeko R, Doherty J K. Merlin knockdown in human schwann cells: Clues to vestibular schwannoma tumorigenesis. Otology & Neurotology. 2010; 31(3):460-6.

Ahmad Z K, Brown C M, Cueva R A, Ryan A F, Doherty J K. ErbB expression, activation, and inhibition with lapatinib and tyrphostin (AG825) in human vestibular schwannomas. Otol Neurotol. 2011 July; 32(5):841-7.

Aminpour S, Tinling S P, Brodie H A. Role of tumor necrosis factor-alpha in sensorineural hearing loss after bacterial meningitis. Otol Neurotol. 2005 July; 26(4):602-9.

Ammoun S, Cunliffe C H, Allen J C, Chiriboga L, Giancotti F G, Zagzag D, Hanemann C O, Karajannis M A. ErbB/HER receptor activation and preclinical efficacy of lapatinib in vestibular schwannoma. Neuro Oncol. 2010 August; 12(8):834-43.

Ammoun S, Provenzano L, Zhou L, Barczyk M, Evans K, Hilton D A, Hafizi S, Hanemann C O. Axl/Gas6/NFkB signalling in schwannoma pathological proliferation, adhesion and survival. Oncogene. 2014 Jan. 16; 33(3): 336-46.

Angelo L S, Maxwell D S, Wu J Y, Sun D, Hawke D H, McCutcheon I E, Slopis J M, Peng Z, Bornmann W G, Kurzrock R. Binding partners for curcumin in human schwannoma cells: biologic implications. Bioorg Med Chem. 2013 Feb. 15; 21(4):932-9.

Angelo L S, Wu J Y, Meng F, Sun M, Kopetz S, McCutcheon I E, Slopis J M, Kurzrock R. Combining curcumin (diferuloylmethane) and heat shock protein inhibition for neurofibromatosis 2 treatment: analysis of response and resistance pathways. Mol Cancer Ther. 2011 November; 10(11):2094-103.

Armati P J, Constable A L, Llewellyn, F. A new medium for in vitro peripheral nervous tissue myelination without the use of antimitotics. J Neuro Meth. 1990; 33(2), 149-155.

Arriaga M A, Long S, Nelson R. Clinical correlates of acoustic neuroma volume. Otol Neurotol. 1993; 14(5): 465-8.

Artz J C, Timmer F C, Mulder J J, Cremers C W, Graamans K. Predictors of future growth of sporadic vestibular schwannomas obtained by history and radiologic assessment of the tumor. Eur Arch Otorhinolaryngol. 2009 May; 266(5):641-6.

Asthagiri A R, Vasquez R A, Butman J A, Wu T, Morgan K, Brewer C C, King K, Zalewski C, Kim H J, Lonser R R. Mechanisms of hearing loss in neurofibromatosis type 2. PLoS One. 2012; 7 (9):e46132.

Au P Y, Martin N, Chau H, Moemeni B, Chia M, Liu F F, Minden M, Yeh W C. The oncogene PDGF-B provides a key switch from cell death to survival induced by TNF. Oncogene. 2005 Apr. 28; 24(19):3196-205.

Bai D, Ueno L, Vogt P K. Akt-mediated regulation of NFkappaB and the essentialness of NFkappaB for the oncogenicity of PI3K and Akt. Int J Cancer. 2009 Dec. 15; 125(12):2863-70.

Balkwill F. Tumour necrosis factor and cancer. Nat Rev Cancer. 2009 May; 9(5):361-71.

Bannwarth B, Netter P, Pourel J, Royer R J, Gaucher A. Clinical pharmacokinetics of nonsteroidal anti-inflammatory drugs in the cerebrospinal fluid. Biomed Pharmacother. 1989; 43(2):121-6.

Barnes P J, Adcock I. Anti-inflammatory actions of steroids: molecular mechanisms. Trends Pharmacol Sci. 1993; 14(12):436-41.

Beg A A, Finco T S, Nantermet P V, Baldwin A S Jr. Tumor necrosis factor and interleukin-1 lead to phosphorylation and loss of I kappa B alpha: a mechanism for NF-kappa B activation. Mol Cell Biol. 1993 June; 13(6):3301-10.

Black P H. Shedding from normal and cancer-cell surfaces. N Engl J Med. 1980; 303(24):1415-6

Blasko I, Lederer W, Oberbauer H, et al. Measurement of thirteen biological markers in CSF of patients with Alzheimer's disease and other dementias. Dement Geriatr Cogn Disord. 2006; 21(1):9-15.

Bradbury D, Clarke D, Seedhouse C, Corbett L, Stocks J, Knox A. Vascular endothelial growth factor induction by prostaglandin E2 in human airway smooth muscle cells is mediated by E prostanoid EP2/EP4 receptors and SP-1 transcription factor binding sites. J Biol Chem. 2005 Aug. 26; 280 (34):29993-30000.

Bunting K, Rao S, Hardy K, Woltring D, Denyer G S, Wang J, Gerondakis S, Shannon M F. Genome-wide analysis of gene expression in T cells to identify targets of the NF-kappa B transcription factor c-Rel. J Immunol. 2007 Jun. 1; 178(11):7097-109.

Burgos-Moron E, Calderón-Montaño J M, Salvador J, Robles A, Lopez-Lazaro M. The dark side of curcumin. Int J Cancer. 2010 Apr. 1; 126(7):1771-5.

Bush M L, Burns S S, Oblinger J, Davletova S, Chang L S, Welling D B, Jacob A. Treatment of vestibular schwannoma cells with ErbB inhibitors. Otol Neurotol. 2012 February; 33(2):244-57.

Calderón-Martínez D, Garavito Z, Spinel C, Hurtado H. Schwann cell-enriched cultures from adult human peripheral nerve: a technique combining short enzymatic dissociation and treatment with cytosine arabinoside (Ara-C). J Neurosci Methods. 2002 Feb. 15; 114(1):1-8.

Casella G T, Bunge R P, Wood P M Improved method for harvesting human Schwann cells from mature peripheral nerve and expansion in vitro. Glia. 1996 August; 17(4): 327-38.

Catz S D, Johnson J L. Transcriptional regulation of bcl-2 by nuclear factor kappa B and its significance in prostate cancer. Oncogene. 2001 Nov. 1; 20(50):7342-51.

Cayé-Thomasen P, Dethloff T, Hansen S, Stangerup S-, Thomsen J. Hearing in patients with intracanalicular vestibular schwannomas. Audiol Neurotol. 2007; 12(1): 1-12.

Cayé-Thomasen P, Werther K, Nalla A, Bog-Hansen T C, Nielsen H J, Stangerup S E, Thomsen J. VEGF and VEGF receptor-1 concentration in vestibular schwannomas homogenates correlates to tumor growth rate. Otol Neurotol. 2005 January; 26(1):98-101.

Chan T A, Morin P J, Vogelstein B, Kinzler K W. Mechanisms underlying nonsteroidal antiinflammatory drug-mediated apoptosis. Proc Natl Acad Sci USA. 1998 Jan. 20; 95(2):681-6.

Charabi S, Klinken L, Tos M, Thomsen J. Histopathology and growth pattern of cystic acoustic neuromas. Laryngoscope. 1994 November; 104 (11 Pt 1):1348-52.

Charabi S, Tos M, Thomsen J, Rygaard J, Fundova P, Charabi B. Cystic vestibular schwannoma—clinical and experimental studies. Acta Otolaryngol Suppl. 2000; 543: 11-3.

Chen C, Halpin C, Rauch S D. Oral steroid treatment of sudden sensorineural hearing loss: A ten year retrospective analysis. Otol Neurotol. 2003; 24(5): 728-33.

Choueiri T K, Mayer E L, Je Y, Rosenberg J E, Nguyen P L, Azzi G R, Bellmunt J, Burstein H J, Schutz F A. Congestive heart failure risk in patients with breast cancer treated with bevacizumab. J Clin Oncol. 2011 Feb. 20; 29(6):632-8.

Cioffi J A, Yue W Y, Mendolia-Loffredo S, Hansen K R, Wackym P A, Hansen M R. MicroRNA-21 overexpression contributes to vestibular schwannoma cell proliferation and survival. Otol Neurotol. 2010 December; 31(9): 1455-62.

Clark J J, Provenzano M, Diggelmann H R, Xu N, Hansen S S, Hansen M R. The ErbB inhibitors trastuzumab and erlotinib inhibit growth of vestibular schwannomas xenografts in nude mice: a preliminary study. Otol Neurotol. 2008 September; 29(6):846-53.

Collen C, Ampe B, Gevaert T, Moens M, Linthout N, De Ridder M, Verellen D, D'Haens J, Storme G. Single fraction versus fractionated linac-based stereotactic radiotherapy for vestibular schwannoma: a single-institution experience. Int J Radiat Oncol Biol Phys. 2011 Nov. 15; 81 (4):e503-9.

Colomer R, Montero S, Lluch A, et al. Circulating HER2 extracellular domain and resistance to chemotherapy in advanced breast cancer. Clin Cancer Res. 2000; 6(6): 2356-62.

Curto M, Cole B K, Lallemand D, Liu C H, McClatchey A I. Contact-dependent inhibition of EGFR signaling by Nf2/Merlin. J Cell Biol. 2007 Jun. 4; 177(5):893-903.

de Vries M, Briaire-de Bruijn I, Malessy M J, de Bruíne S F, van der Mey A G, Hogendoorn P C. Tumor-associated macrophages are related to volumetric growth of vestibular schwannomas. Otol Neurotol. 2013 February; 34(2): 347-52.

Demetriades A K, Saunders N, Rose P, Fisher C, Rowe J, Tranter R, Hardwidge C. Malignant transformation of acoustic neuroma/vestibular schwannoma 10 years after gamma knife stereotactic radiosurgery. Skull Base. 2010 September; 20(5):381-7.

Dewan M Z, Terashima K, Taruishi M, Hasegawa H, Ito M, Tanaka Y, Mori N, Sata T, Koyanagi Y, Maeda M, Kubuki Y, Okayama A, Fujii M, Yamamoto N. Rapid tumor formation of human T-cell leukemia virus type 1-infected cell lines in novel NOD-SCID/gammac(null) mice: suppression by an inhibitor against NF-kappaB. J Virol. 2003 May; 77(9):5286-94.

Dilwali S, Lysaght A, Roberts D, Barker F G 2nd, McKenna M J, Stankovic K M. Sporadic vestibular schwannomas associated with good hearing secrete higher levels of fibroblast growth factor 2 than those associated with poor hearing irrespective of tumor size. Otol Neurotol. 2013 June; 34(4):748-54.

Dinh C T, Haake S, Chen S, Hoang K, Nong E, Eshraghi A A, Balkany T J, Van De Water T R. Dexamethasone protects organ of corti explants against tumor necrosis factor-alpha-induced loss of auditory hair cells and alters the expression levels of apoptosis-related genes. Neuroscience. 2008 Nov. 19; 157(2):405-13.

Doherty J K, Ongkeko W, Crawley B, Andalibi A, Ryan A F. ErbB and Nrg: potential molecular targets for vestibular schwannoma pharmacotherapy. Otol Neurotol. 2008 January; 29(1):50-7.

Evans D G, Howard E, Giblin C, Clancy T, Spencer H, Huson S M, Lalloo F. Birth incidence and prevalence of tumor-prone syndromes: estimates from a UK family genetic register service. Am J Med Genet A. 2010 February; 152 A (2):327-32.

Evans D G. Neurofibromatosis type 2 (NF2): a clinical and molecular review. Orphanet J Rare Dis. 2009 Jun. 19; 4:16.

Evans G R, Lloyd S K, Ramsden R T. Neurofibromatosis type 2. Adv Otorhinolaryngol. 2011; 70:91-8.

Gherardi E, Birchmeier W, Birchmeier C, Vande Woude G. Targeting MET in cancer: rationale and progress. Nat Rev Cancer. 2012 Jan. 24; 12(2):89-103.

Gilmore T. "NF-kB Transcription Factors". Boston University. website: www.nf-kb.org, 2014 May 22

Gilmore T D, Kalaitzidis D, Liang M C, Starczynowski D T. The c-Rel transcription factor and B-cell proliferation: a deal with the devil. Oncogene. 2004 Mar. 25; 23(13): 2275-86.

Goldbach-Mansky R, Dailey N J, Canna S W, et al. Neonatal-onset multisystem inflammatory disease responsive to interleukin-1B inhibition. N Engl J Med. 2006; 355(6): 581-92

Gorsuch R A, Hyde D R. Regulation of Müller glial dependent neuronal regeneration in the damaged adult zebrafish retina. Exp Eye Res. 2013 Jul. 20. pii: 50014-4835 (13)00210-8.

Gouveris H T, Victor A, Mann W J. Cochlear origin of early hearing loss in vestibular schwannoma. Laryngoscope. 2007 April; 117(4):680-3.

Gutmann D H, Giordano M J, Fishback A S, Guha A. Loss of merlin expression in sporadic meningiomas, ependymomas and schwannomas. Neurology. 1997; 49(1):267-270.

Haake S M, Dinh C T, Chen S, Eshraghi A A, Van De Water T R. Dexamethasone protects auditory hair cells against TNFalpha-initiated apoptosis via activation of PI3K/Akt and NFkappaB signaling. Hear Res. 2009 September; 255 (1-2):22-32.

Hanemann C O, Bartelt-Kirbach B, Diebold R, Kampchen K, Langmesser S, Utermark T. Differential gene expression between human schwannoma and control schwann cells. Neuropathol Appl Neurobiol. 2006; 32(6):605-14.

Hansen M R, Roehm P C, Chatterjee P, Green S H. Constitutive neuregulin-1/ErbB signaling contributes to human vestibular schwannoma proliferation. Glia. 2006; 53 (6):593-600.

Hardman J, Limbird L, Gilman A, Goodman L. Goodman & Gilman's the Pharmacological Basis of Therapeutics. 9th ed. New York: McGraw-Hill, Health Professions Division; 1996.

Hardy D G, Macfarlane R, Baguley D, Moffat D A. Surgery for acoustic neurinoma. An analysis of 100 translabyrinthine operations. J Neurosurg. 1989 December; 71 (6): 799-804.

Hatcher H, Planalp R, Cho J, Torti F M, Torti S V. Curcumin: from ancient medicine to current clinical trials. Cell Mol Life Sci. 2008 June; 65 (11):1631-52.

Herwadker A, Vokurka E A, Evans D G, Ramsden R T, Jackson A. Size and growth rate of sporadic vestibular schwannoma: predictive value of information available at presentation. Otol Neurotol. 2005 January; 26(1):86-92.

Hoesel B, Schmid J A. The complexity of NF-κB signaling in inflammation and cancer. Mol Cancer. 2013 Aug. 2; 12:86.

Hong B, Krusche C A, Schwabe K, Friedrich S, Klein R, Krauss J, Nakamura M. Cyclooxygenase-2 Supports Tumor Proliferation in Vestibular Schwannomas. Neurosurgery. 68:1112-1117

Hood B, Levene H B, Levi A D. Transplantation of autologous Schwann cells for the repair of segmental peripheral nerve defects. Neurosurg Focus. 2009 February; 26 (2): E4.

Hung G, Colton J, Fisher L, Oppenheimer M, Faudoa R, Slattery W, Linthicum F. Immunohistochemistry study of human vestibular nerve schwannoma differentiation. Glia. 2002 June; 38(4):363-70.

Hung G, Li X, Faudoa R, Xeu Z, Kluwe L, Rhim J S, Slattery W, Lim D. Establishment and characterization of a schwannoma cell line from a patient with neurofibromatosis 2. Int J Oncol. 2002 March; 20(3):475-82.

Jacob A, Lee T X, Neff B A, Miller S, Welling B, Chang L S. Phosphatidylinositol 3-kinase/AKT pathway activation in human vestibular schwannoma. Otol Neurotol. 2008 January; 29(1):58-68.

Jacoby L B, MacCollin M, Barone R, Ramesh V, Gusella J F. Frequency and distribution of NF2 mutations in schwannomas. Genes Chromosom Cancer. 1996; 17(1): 45-55.

Jin Y Q, Liu W, Hong T H, Cao Y. Efficient Schwann cell purification by differential cell detachment using multiplex collagenase treatment. J Neurosci Methods. 2008 May 15; 170(1):140-8.

Juhn S K, Prado S, Rybak L. Effect of urea on osmolality of perilymph. Arch Otolaryngol. 1979 September; 105(9): 538-41.

Kaiser G C, Yan F, Polk D B. Mesalamine blocks tumor necrosis factor growth inhibition and nuclear factor kappaB activation in mouse colonocytes. Gastroenterology. 1999.116:602-609.

Kandathil C K, Dilwali S, Wu C C, Ibrahimov M, McKenna M J, Lee H, Stankovic K M. Aspirin intake correlates with halted growth of sporadic vestibular schwannoma in vivo. Otol Neurotol. 2014 February; 35(2):353-7.

Karajannis M A, Legault G, Hagiwara M, Ballas M S, Brown K, Nusbaum A O, Hochman T, Goldberg J D, Koch K M, Golfinos J G, Roland J T, Allen J C. Phase II trial of lapatinib in adult and pediatric patients with neurofibromatosis type 2 and progressive vestibular schwannomas. Neuro Oncol. 2012 September; 14 (9): 1163-70.

Karin M. How NF-kappaB is activated: the role of the IkappaB kinase (IKK) complex. Oncogene. 1999 Nov. 22; 18(49):6867-74.

Kaye A, Briggs R, Morokoff A. Part 3—Nerve sheath tumors 28—acoustic neurinoma (vestibular schwannoma). In: Brain tumors: An encyclopedic approach. 2001:518.

Kikkawa Y S, Nakagawa T, Tsubouchi H, Ido A, Inaoka T, Ono K, Ito J. Hepatocyte growth factor protects auditory hair cells from aminoglycosides. Laryngoscope. 2009 October; 119(10):2027-31

Kim J Y, Kim H, Jeun S S, Rha S J, Kim Y H, Ko Y J, Won J, Lee K H, Rha H K, Wang Y P. Inhibition of NF-kappaB activation by merlin. Biochem Biophys Res Commun 2002. 296:1295-302.

Kopp E, Ghosh S. Inhibition of NF-kB by Sodium Salicylate and Aspirin. Science 1994. 265: 956-959.

Koutsimpelas D, Stripf T, Heinrich U R, Mann W J, Brieger J. Expression of vascular endothelial growth factor and basic fibroblast growth factor in sporadic vestibular schwannomas correlates to growth characteristics. Otol Neurotol. 2007 December; 28(8):1094-9.

Lallemand D, Manent J, Couvelard A, Watilliaux A, Siena M, Chareyre F, Lampin A, Niwa-Kawakita M, Kalamarides M, Giovannini M. Merlin regulates transmembrane receptor accumulation and signaling at the plasma membrane in primary mouse Schwann cells and in human schwannomas. Oncogene. 2009 Feb. 12; 28(6):854-65.

Larsson A, Skoldenberg E, Ericson H. Serum and plasma levels of FGF-2 and VEGF in healthy blood donors. Angiogenesis. 2002; 5(1):107-110.

Lassaletta L, Martinez-Glez V, Torres-Martin M, Rey J A, Gavilan J. cDNA microarray expression profile in vestibular schwannoma: correlation with clinical and radiological features. Cancer Genet Cytogenet 2009; 194:125-7.

Lebel M H, Freij B J, Syrogiannopoulos G A, et al. Dexamethasone therapy for bacterial meningitis. N Engl J Med. 1988; 319(15):964-71.

Lee J, Rhee M H, Kim E, Cho J Y. BAY 11-7082 is a broad-spectrum inhibitor with anti-inflammatory activity against multiple targets. Mediators Inflamm. 2012: 416036.

Lee J D, Kwon T J, Kim U K, Lee W S. Genetic and epigenetic alterations of the NF2 gene in sporadic vestibular schwannomas. PLoS One. 2012; 7 (1):e30418.

Lee S T, Li Z, Wu Z, Aau M, Guan P, Karuturi R K, Liou Y C, Yu Q. Context-specific regulation of NF-kB target gene expression by EZH2 in breast cancers. Mol Cell. 2011 Sep. 2; 43(5):798-810.

Leychenko A, Konorev E, Jijiwa M, Matter M L. Stretch-induced hypertrophy activates NFkB-mediated VEGF secretion in adult cardiomyocytes. PLoS One. 2011; 6 (12):e29055.

Liberman M C, Gao J, He D Z, Wu X, Jia S, Zuo J. Prestin is required for electromotility of the outer hair cell and for the cochlear amplifier. Nature. 2002 Sep. 19; 419(6904): 300-4.

Lieu C H, Tran H, Jiang Z Q, Mao M, Overman M J, Lin E, Eng C, Morris J, Ellis L, Heymach J V, Kopetz S. The association of alternate VEGF ligands with resistance to anti-VEGF therapy in metastatic colorectal cancer. PLoS One. 2013 Oct. 15; 8 (10):e77117.

Lobo D, Garcia-Berrocal J R, Trinidad A, Verdaguer J M, Ramirez-Camacho R. Review of the biologic agents used for immune-mediated inner ear disease. Acta Otorrinolaringol Esp. 2013 May-June; 64(3):223-9.

London N R, Gurgel R K. The role of vascular endothelial growth factor and vascular stability in diseases of the ear. Laryngoscope. 2013 Dec. 17. [Epub ahead of print]

Lou Z. Healing large traumatic eardrum perforations in humans using fibroblast growth factor applied directly or via gelfoam. Otol Neurotol. 2012 December; 33(9):1553-7.

Low W, Dazert S, Baird A, Ryan A F. Basic fibroblast growth factor (FGF-2) protects rat cochlear hair cells in organotypical culture from aminoglycoside injury. J Cell Physiol. 1996; 167(3):443-450.

Lysaght A C, Kao S, Paulo J A, Merchant S N, Steen H, Stankovic K M. Proteome of human perilymph. J Proteome Res. 2011; 10(9):3845-51.

Mahaley M S J, Mettlin C, Natarajan N, Laws E R J, Peace B B. Analysis of patterns of care of brain tumor patients in the united states: A study of the brain tumor section of the AANS and the CNS and the commission on cancer of the ACS. Clin Neurosurg. 1990; 36:347-5

Mahboubi H, Ahmed O H, Yau A Y, Ahmed Y C, Djalilian H R. Complications of surgery for sporadic vestibular schwannoma. Otolaryngol Head Neck Surg. 2014 February; 150(2):275-81.

Mahmud M R, Khan A M, Nadol J B Jr. Histopathology of the inner ear in unoperated acoustic neuroma. Ann Otol Rhinol Laryngol. 2003 November; 112(11):979-86.

Marin Y E, Wall B A, Wang S, Namkoong J, Martino J J, Suh J, Lee H J, Rabson A B, Yang C S, Chen S, Ryu J H. Curcumin downregulates the constitutive activity of NF-kappaB and induces apoptosis in novel mouse melanoma cells. Melanoma Res. 2007 October; 17(5):274-83.

Marumo T, Schini-Kerth V B, Busse R. Vascular endothelial growth factoractivates nuclear factor-kappaB and induces monocyte chemoattractant protein-1 in bovine retinal endothelial cells. Diabetes. 1999 May; 48(5):1131-7.

Matsumura A, Kubota T, Taiyoh H, Fujiwara H, Okamoto K, Ichikawa D, Shiozaki A, Komatsu S, Nakanishi M, Kuriu Y, Murayama Y, Ikoma H, Ochiai T, Kokuba Y, Nakamura T, Matsumoto K, Otsuji E. HGF regulates VEGF-A expression via the c-Met receptor downstream pathways, PI3K/Akt, MAPK and STAT3, in CT26 murine cells. Int J Oncol. 2013 February; 42(2):535-42.

Matthies C, Samii M. Management of 1000 vestibular schwannomas (acoustic neuromas): clinical presentation. Neurosurgery. 1997 January; 40(1):1-9; discussion 9-10.

McCarty J H. Glioblastoma resistance to anti-VEGF therapy: has the challenge been MET? Clin Cancer Res. 2013 Apr. 1; 19(7):1631-3.

Meyer T A, Canty P A, Wilkinson E P, Hansen M R, Rubinstein J T, Gantz B J. Small acoustic neuromas: surgical outcomes versus observation or radiation. Otol Neurotol. 2006 April; 27(3):380-92.

Meyer zum Gottesberge A M, Massing T, Hansen S. Missing mitochondrial Mpv17gene function induces tissue-specific cell-death pathway in the degeneratinginner ear. Cell Tissue Res. 2012 February; 347(2):343-56.

Miller C, Igarashi S, Jacob A. Molecular pathogenesis of vestibular schwannomas: Insights for the development of novel medical therapies. Otolaryngologia Polska. 2012; 66(2):84-95.

Miller M E, Mafee M F, Bykowski J, Alexander T H, Burchette R J, Mastrodimos B, Cueva R A. Hearing preservation and vestibular schwannoma: intracochlear FLAIR signal relates to hearing level. Otol Neurotol. 2014 February; 35(2):348-52.

Møller M N, Werther K, Nalla A, Stangerup S E, Thomsen J, Bog-Hansen T C, Nielsen H J, Cayé-Thomasen P. Angiogenesis in vestibular schwannomas: expression of extracellular matrix factors MMP-2, MMP-9, and TIMP-1. Laryngoscope. 2010 April; 120(4):657-62.

Monge Naldi A, Gassmann M, Bodmer D. Erythropoietin but not VEGF has a protective effect on auditory hair cells in the inner ear. Cell Mol Life Sci. 2009 November; 66(22):3595-9.

Moriyama T, Kataoka H, Hamasuna R, Yokogami K, Uehara H, Kawano H, Goya T, Tsubouchi H, Koono M, Wakisaka S. Up-regulation of vascular endothelial growth factor induced by hepatocyte growth factor/scatter factor stimulation in human glioma cells. Biochem Biophys Res Commun. 1998 Aug. 10; 249(1):73-7. (b)

Moriyama T, Kataoka H, Kawano H, Yokogami K, Nakano S, Goya T, Uchino H, Koono M, Wakisaka S. Comparative analysis of expression of hepatocyte growth factor and its receptor, c-met, in gliomas, meningiomas and schwannomas in humans. Cancer Lett. 1998 Feb. 27; 124(2):149-55. (a)

Nadol J B Jr, Diamond P F, Thornton A R. Correlation of hearing loss and radiologic dimensions of vestibular schwannomas (acoustic Neuromas). Am J Otol. 1996 March; 17(2):312-6.

Nadol J B Jr. Application of electron microscopy to human otopathology. Ultrastructural findings in neural presbycusis, Meniere's disease and Usher's syndrome. Acta Otolaryngol. 1988 May-June; 105 (5-6):411-9

Neff B A, Welling D B, Akhmametyeva E, Chang L S. The molecular biology of vestibular schwannomas: dissecting the pathogenic process at the molecular level. Otol Neurotol. 2006 February; 27(2):197-208.

Nickols J C, Valentine W, Kanwal S, Carter B D. Activation of the transcription factor NF-kappaB in Schwann cells is required for peripheral myelin formation. Nat Neurosci. 2003 February; 6(2):161-7.

O'Dea E L, Kearns J D, Hoffmann A. U V as an amplifier rather than inducer of NF-kappaB activity. Mol Cell. 2008 Jun. 6; 30(5):632-41.

Olsaysky K M, Page J L, Johnson M C, Zarbl H, Strom S C, Omiecinski C J. Gene expression profiling and differentiation assessment in primary human hepatocyte cultures, established hepatoma cell lines, and human liver tissues. Toxicol Appl Pharmacol. 2007 Jul. 1; 222(1):42-56.

Olson C M, Hedrick M N, Izadi H, Bates T C, Olivera E R, Anguita J. p38 mitogen-activated protein kinase controls NF-kappaB transcriptional activation and tumor necrosis factor alpha production through RelA phosphorylation mediated by mitogen- and stress-activated protein kinase 1 in response to Borrelia burgdorferi antigens. Infect Immun. 2007 January; 75(1):270-7.

Ousman S S, Tomooka B H, van Noort J M, et al. Protective and therapeutic role for [agr]B-crystallin in autoimmune demyelination. Nature. 2007; 448(7152):474-9.

Pannunzio M E, Jou I M, Long A, Wind T C, Beck G, Balian G. A new method of selecting Schwann cells from adult mouse sciatic nerve. J Neurosci Methods. 2005 Nov. 30; 149(1):74-81.

Pauler M, Schuknecht H F, Thornton A R. Correlative studies of cochlear neuronal loss with speech discrimination and pure-tone thresholds. Arch Otorhinolaryngol. 1986; 243(3):200-6.

Pettersson D, Mathiesen T, Prochazka M, Bergenheim T, Florentzson R, Harder H, Nyberg G, Siesjo P, Feychting M. Long-term mobile phone use and acoustic neuroma risk. Epidemiology. 2014 March; 25(2):233-41.

Picciotti P, Torsello A, Wolf F I, Paludetti G, Gaetani E, Pola R. Age-dependent modifications of expression level of VEGF and its receptors in the inner ear. Exp Gerontol. 2004 August; 39(8):1253-8.

Picciotti P M, Fetoni A R, Paludetti G, Wolf F I, Torsello A, Troiani D, Ferraresi A, Pola R, Sergi B. Vascular endothelial growth factor (VEGF-A) expression in noise-induced hearing loss. Hear Res. 2006 April; 214 (1-2):76-83.

Picciotti P M, Torsello A, Cantore I, Stigliano E, Paludetti G, Wolf F I. Expression of vascular endothelial growth factor and its receptors in the cochlea of various experimental animals. Acta Otolaryngol. 2005 November; 125(11): 1152-7.

Pierce J W, Schoenleber R, Jesmok G, Best J, Moore S A, Collins T, Gerritsen M E. Novel inhibitors of cytokine-induced IkappaBalpha phosphorylation and endothelial cell adhesion molecule expression show anti-inflammatory effects in vivo. J Biol Chem. 1997 Aug. 22; 272(34): 21096-103.

Plotkin S R, Merker V L, Halpin C, Jennings D, McKenna M J, Harris G J, Barker F G 2nd. Bevacizumab for progressive vestibular schwannoma in neurofibromatosis type 2: a retrospective review of 31 patients. Otol Neurotol. 2012 August; 33(6):1046-52.

Plotkin S R, Stemmer-Rachamimov A O, Barker F G 2nd, Halpin C, Padera T P, Tyrrell A, Sorensen A G, Jain R K, di Tomaso E. Hearing improvement after bevacizumab in patients with neurofibromatosis type 2. N Engl J Med. 2009 Jul. 23; 361(4):358-67.

Propp J M, McCarthy B J, Davis F G, Preston-Martin S. Descriptive epidemiology of vestibular schwannomas. Neuro Oncol. 2006 January; 8(1):1-11.

Romashkova J A, Makarov S S. NF-kappaB is a target of AKT in anti-apoptotic PDGF signalling. Nature. 1999 Sep. 2; 401(6748):86-90.

Rossi M L, Jones N R, Esiri M M, Havas L, Nakamura N, Coakham H B. Mononuclear cell infiltrate, HLA-Dr expression and proliferation in 37 acoustic schwannomas. Histol Histopathol. 1990 October; 5(4):427-32.

Rynne M, Maclean C, Bybee A, McDermott M F, Emery P. Hearing improvement in a patient with variant muckle-wells syndrome in response to interleukin 1 receptor antagonism. Ann Rheum Dis. 2006; 65(4):533-4.

Sainz J, Huynh D P, Figueroa K, Ragge N K, Baser M E, Pulst S. Mutations of the neurofibromatosis type 2 gene and lack of the gene product in vestibular schwannomas. Hum Mol Genet. 1994; 3(6):885-91.

Salehi P, Akinpelu O V, Waissbluth S, Peleva E, Meehan B, Rak J, Daniel S J. Attenuation of Cisplatin Ototoxicity by Otoprotective Effects of Nanoencapsulated Curcumin and Dexamethasone in a Guinea Pig Model. Otol Neurotol. 2014 May 16. Salven P, Orpana A, Teerenhovi L, Joensuu H. Simultaneous elevation in the serum concentrations of the angiogenic growth factors VEGF and bFGF is an independent predictor of poor prognosis in non-hodgkin lymphoma: A single-institution study of 200 patients. Blood. 2000; 96(12):3712-3718.

Satoh H, Firestein G S, Billings P B, Harris J P, Keithley E M. Proinflammatory cytokine expression in the endolymphatic sac during inner ear inflammation. J Assoc Res Otolaryngol. 2003; 4(2):139-47.

Schrattenholz A, Groebe K, Soskic V. Systems biology approaches and tools for analysis of interactomes and multi-target drugs. Methods Mol Biol. 2010; 662:29-58.

Schultz J M, Khan S N, Ahmed Z M, Riazuddin S, Waryah A M, Chhatre D, Starost M F, Ploplis B, Buckley S, Velasquez D, Kabra M, Lee K, Hassan M J, Ali G, Ansar M, Ghosh M, Wilcox E R, Ahmad W, Merlino G, Leal S M, Riazuddin S, Friedman T B, Morell R J. Noncoding mutations of HGF are associated with nonsyndromic hearing loss, DFNB39. Am J Hum Genet. 2009 July; 85(1):25-39.

Silverstein, H. A rapid protein test for acoustic neurinoma. Arch. Otolaryngol 1972, 95, 202-204.

Silverstein, H. Labyrinthine tap as a diagnostic test for acoustic neurinoma. Otolaryngol. Clin. North Am. 1973, 6, 229-244.

Smouha E E, Yoo M, Mohr K, Davis R P. Conservative management of acoustic neuroma: a meta-analysis and proposed treatment algorithm. Laryngoscope. 2005 March; 115(3):450-4.

Sobolewski C, Cerella C, Dicato M, Ghibelli L, Diederich M. The role of cyclooxygenase-2 in cell proliferation and cell death in human malignancies. Int J Cell Biol. 2010; 2010:215158.

Sondell M, Lundborg G, Kanje M. Vascular endothelial growth factor has neurotrophic activity and stimulates axonal outgrowth, enhancing cell survival and Schwann cell proliferation in the peripheral nervous system. J Neurosci. 1999. Jul. 15; 19(14):5731-40.

Sørensen V, Nilsen T, Wiedlocha A. Functional diversity of FGF-2 isoforms by intracellular sorting. Bioessays. 2006; 28(5):504-14.

Spiegel I, Peles E. A novel method for isolating Schwann cells using the extracellular domain of Necl1. J Neurosci Res. 2009 Nov. 15; 87(15):3288-96.

Spreca, A., Rambotti, M. G., Rende, M., Saccardi, C., Aisa, M. C., Giambanco, I., & Donato, R. (1989) Immunocytochemical localization of 5-100b protein in degenerating and regenerating rat sciatic nerves. Journal of Histochemistry & Cytochemistry, 37(4), 441-446.

Stangerup S E, Cayé-Thomasen P. Epidemiology and natural history of vestibular schwannomas. Otolaryngol Clin North Am. 2012 April; 45(2):257-68

Stankovic K M, Mrugala M M, Martuza R L, Silver M, Betensky R A, Nadol J B, Stemmer-Rachamimov A. Genetic determinants of hearing loss associated with vestibular schwannomas. Otol Neurotol 2009. 30: 661-667.

Steffensen K D, Waldstrom M, Jeppesen U, Knudsen H J, Brandslund I, Jakobsen A. Preoperative serum levels of epidermal growth factor receptor, HER2, and vascular endothelial growth factor in malignant and benign ovarian tumors. Clin Ovarian Cancer. 2008; 1(2):127-34

Sughrue M E, Yang I, Aranda D, et al. The natural history of untreated sporadic vestibular schwannomas: A comprehensive review of hearing outcomes. J Neurosurg. 2010; 112(1):163-167.

Sughrue M E, Yang I, Aranda D, Rutkowski M J, Fang S, Cheung S W, Parsa A T. Beyond audiofacial morbidity after vestibular schwannoma surgery. J Neurosurg. 2011 February; 114(2):367-74. (a)

Sughrue M E, Yeung A H, Rutkowski M J, Cheung S W, Parsa A T. Molecular biology of familial and sporadic vestibular schwannomas: implications for novel therapeutics. J Neurosurg. 2011 February; 114(2):359-66. (b)

Sulpice E, Ding S, Muscatelli-Groux B, Berge M, Han Z C, Plouet J, Tobelem G, Merkulova-Rainon T. Cross-talk between the VEGF-A-A and HGF signalling pathways in endothelial cells. Biol Cell. 2009 September; 101(9):525-39.

Tadros S F, D'Souza M, Zhu X, Frisina R D. Gene expression changes for antioxidants pathways in the mouse cochlea: relations to age-related hearing deficits. PLoS One. 2014 Feb. 28; 9 (2):e90279.

Taylor D, Black P. Shedding of plasma membrane fragments. neoplastic and developmental importance. Dev Biol (N Y). 1986; 3:33-57

Tew J, McMahon N. Acoustic neuroma. Mayfield Clinic for Brain and Spine Web site. http://www.mayfieldclinic.com/PE-Acoustic.htm#.U4SmaHJdXXU. Updated 2013. Accessed May 20, 2014.

Thakur J D, Banerjee A D, Khan I S, Sonig A, Shorter C D, Gardner G L, Nanda A, Guthikonda B. An update on unilateral sporadic small vestibular schwannoma. Neurosurg Focus. 2012 September; 33 (3):E1.

Thomsen J, Zilstorff K, Tos M. Acoustic neuromas (diagnostic value of testing the function of the trigeminal nerve, the cerebellum and optokinetic nystagmus). J Laryngol Otol. 1983 September; 97(9):801-12.

Tokuda H, Takai S, Hanai Y, Harada A, Matsushima-Nishiwaki R, Kato H, Ogura S, Kozawa O. Potentiation by platelet-derived growth factor-BB of FGF-2-stimulated VEGF-A release in osteoblasts. J Bone Miner Metab. 2008; 26(4):335-41.

Toualbi-Abed K, Daniel F, Güller M C, Legrand A, Mauriz J L, Mauviel A, Bernuau D. Jun D cooperates with p65 to activate the proximal kappaB site of the cyclin D1 promoter: role of PI3K/PDK-1. Carcinogenesis. 2008 March; 29(3):536-43.

Turner D J, Alaish S M, Zou T, Rao J N, Wang J Y, Strauch E D. Bile salts induce resistance to apoptosis through NF-kappaB-mediated XIAP expression. Ann Surg. 2007 March; 245(3):415-25.

Utermark T, Kaempchen K, Antoniadis G, Hanemann C O. Reduced apoptosis rates in human schwannomas. Brain Pathol. 2005 January; 15(1):17-22.

van de Langenberg R, de Bondt B J, Nelemans P J, Dohmen A J, Baumert B G, Stokroos R J. Predictors of volumetric growth and auditory deterioration in vestibular schwannomas followed in a wait and scan policy. Otol Neurotol. 2011 February; 32(2):338-44.

Vernooij M W, Ikram M A, Tanghe H L, Vincent A J, Hofman A, Krestin G P, Niessen W J, Breteler M M, van der Lugt A. Incidental findings on brain MRI in the general population. N Engl J Med. 2007 Nov. 1; 357(18): 1821-8.

Wang J, Coltrera M D, Gown A M. Cell proliferation in human soft tissue tumors correlates with platelet-derived growth factor B chain expression: An immunohistochemical and in situ hybridization study. Cancer Res. 1994; 54(2):560-4

Weerda H G. Effects of transforming growth factor-ÃŸ1 and basic fibroblast growth factor on proliferation of cell cultures derived from human vestibular nerve schwannoma. Acta Otolaryngol. 1998; 118(3):337-43

Welling D B, Guida M, Goll F, et al. Mutational spectrum in the neurofibromatosis type 2 gene in sporadic and familial schwannomas. Hum Genet. 1996; 98(2):189-93.

Wilson W R, Byl F M, Laird N. The efficacy of steroids in the treatment of idiopathic sudden hearing loss. A double-blind clinical study. Arch Otolaryngol. 1980 December; 106(12):772-6.

Wong H K, Landenranta J, Kamoun W S, Chan A W, McClatchey A I, Plotkin S R, Jain R K, di Tomaso E. Anti-vascular endothelial growth factor therapies as a novel therapeutic approach to treating neurofibromatosis-related tumors. Cancer Res. 2010 May 1; 70(9):3483-93.

Yin J F, Zhai S F, Guo W F, Hu Y F, Shi L. Protective and rescue effects of transgenic bFGF/GFP expression mediated by cationic liposome on gentamicin-induced guinea pig cochlear toxicity. Zhonghua yi xue za zhi. 2002; 82(17):1192-4

Yin, M J, Yamamoto, Y, Gaynor, R B. The anti-inflammatory agents aspirin and salicylate inhibit the activity of I(kappa)B kinase-beta. Nature. 1998. 396:77-80.

Yoshimoto Y. Systematic review of the natural history of vestibular schwannoma. J Neurosurg. 2005 July; 103(1): 59-63.

Zhai S, Cheng J, Wang J, Yang W, Gu R, Jiang S. Protective effect of basic fibroblast growth factor on auditory hair cells after noise exposure. Acta Otolaryngol. 2002; 122 (4):370-3

Zhai S, Wang D, Wang J, Han D, Yang W. Basic fibroblast growth factor protects auditory neurons and hair cells from glutamate neurotoxicity and noise exposure. Acta Otolaryngol. 2004; 124(2):124-9.

Zheng J L, Gao W Q. Differential damage to auditory neurons and hair cells by ototoxins and neuroprotection by specific neurotrophins in rat cochlear organotypic cultures. Eur J Neurosci. 1996 September; 8(9):1897-905.

Zou J, Pyykko I, Sutinen P, Toppila E. Vibration induced hearing loss in guinea pig cochlea: expression of TNF-alpha and VEGF. Hear Res. 2005 April; 202 (1-2):13-20.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject having vestibular schwannoma, the method comprising identifying a subject having a vestibular schwannoma and administering to the ear of the subject a therapeutically effective amount of a TNFα inhibitor by direct delivery into the inner ear.

2. A method of reducing the rate of vestibular schwannoma tumor growth in a subject, the method comprising identifying a subject having a vestibular schwannoma and administering to the ear of the subject a therapeutically effective amount of a TNFα inhibitor by direct delivery into the inner ear.

3. The method of claim 1, wherein the TNFα inhibitor is selected from the group consisting of: adalimumab, infliximab, golimumab, etanercept, and certolizumab.

4. The method of claim 1, wherein the local administration is injection through the ear drum.

5. The method of claim 2, wherein the local administration is direct delivery into the inner ear.

* * * * *

UNITED STATES PATENT AND TRADEMARK OFFICE
CERTIFICATE OF CORRECTION

PATENT NO. : 10,010,585 B2
APPLICATION NO. : 14/741332
DATED : July 3, 2018
INVENTOR(S) : Konstantina Stankovic and Sonam Dilwali Page 1 of 1

It is certified that error appears in the above-identified patent and that said Letters Patent is hereby corrected as shown below:

In the Claims

Column 108, Line 37, Claim 4 after "the" delete "local".

Column 108, Line 39, Claim 5 after "the" delete "local".

Signed and Sealed this
Second Day of July, 2019

Andrei Iancu
*Director of the United States Patent and Trademark Office*